(12) United States Patent
Tholkes et al.

(10) Patent No.: US 9,616,282 B2
(45) Date of Patent: Apr. 11, 2017

(54) MULTI-MODAL GAIT-BASED NON-INVASIVE THERAPY PLATFORM

(71) Applicant: ALT Innovations LLC, Prior Lake, MN (US)

(72) Inventors: Alan Tholkes, Prior Lake, MN (US); DuWayne Dandurand, Jordan, MN (US)

(73) Assignee: ALT Innovations LLC, Prior Lake, MN (US)

( * ) Notice: Subject to any disclaimer, the term of this patent is extended or adjusted under 35 U.S.C. 154(b) by 48 days.

(21) Appl. No.: 14/529,568

(22) Filed: Oct. 31, 2014

(65) Prior Publication Data

US 2015/0165265 A1    Jun. 18, 2015

Related U.S. Application Data

(60) Provisional application No. 61/915,834, filed on Dec. 13, 2013.

(51) Int. Cl.
*A61H 1/00* (2006.01)
*A61H 1/02* (2006.01)
(Continued)

(52) U.S. Cl.
CPC ...... *A63B 22/0664* (2013.01); *A63B 22/0002* (2013.01); *A63B 22/02* (2013.01);
(Continued)

(58) Field of Classification Search
CPC . A63B 22/0002; A63B 22/02; A63B 22/0292; A63B 22/0664; A63B 23/03566; A63B 71/0009; A63B 2022/0647; A63B 2022/0676; A63B 2208/0204; A63B 2208/0233; A63B 2225/093; A61H 2003/005; A61H 3/00; A61H 3/008;
(Continued)

(56) References Cited

U.S. PATENT DOCUMENTS 6,770,040 B2 * 8/2004 Perner .................. A61F 5/0102
                                                              482/124
6,821,233 B1 * 11/2004 Colombo ............. A61F 5/0102
                                                              482/54
(Continued)

*Primary Examiner* — Joshua Lee
(74) *Attorney, Agent, or Firm* — Craige Thompson; Thompson Patent Law

(57) ABSTRACT

Apparatus and associated methods relate to a knee-position control system having a knee engagement pad, a lower-leg control member and an upper-leg control member, the knee engagement pad configured to naturally position a user's knee in response to movement of a foot-rest of a natural-gait therapy system. In an illustrative embodiment, the upper-leg control member may pivot about a point substantially axially coincident with a user's hip. In some embodiments, the upper-leg control member may be pivotally coupled to the lower-leg control member at a pivot point substantially axially coincident with a user's knee. The lower-leg control member may be pivotally coupled to the foot rest at a pivot point substantially axially coincident with a user's ankle. The knee-position control system may advantageously position a user's knee in a natural position relative to both the user's ankle and the user's hip, in response to movement of the user's foot.

15 Claims, 56 Drawing Sheets

(51) Int. Cl.
*A63B 24/00* (2006.01)
*A63B 26/00* (2006.01)
*A63B 22/06* (2006.01)
*A63B 22/02* (2006.01)
*A63B 71/00* (2006.01)
*A63B 22/00* (2006.01)
*A63B 22/20* (2006.01)
*A63B 23/035* (2006.01)
*A61H 3/00* (2006.01)

(52) U.S. Cl.
CPC ........ *A63B 22/0292* (2015.10); *A63B 22/203* (2013.01); *A63B 23/03566* (2013.01); *A63B 71/0009* (2013.01); *A61H 1/005* (2013.01); *A61H 1/024* (2013.01); *A61H 1/0237* (2013.01); *A61H 1/0262* (2013.01); *A61H 1/0266* (2013.01); *A61H 3/00* (2013.01); *A61H 3/008* (2013.01); *A61H 2003/005* (2013.01); *A63B 2022/0676* (2013.01); *A63B 2208/0204* (2013.01); *A63B 2208/0233* (2013.01); *A63B 2225/093* (2013.01)

(58) Field of Classification Search
CPC .... A61H 1/005; A61H 1/0237; A61H 1/0262; A61H 1/0266; A61H 2001/027
USPC ........................................ 601/5, 35
See application file for complete search history.

(56) References Cited

U.S. PATENT DOCUMENTS

| | | | | |
|---|---|---|---|---|
| 7,163,492 B1* | 1/2007 | Sotiriades | ............ | A61H 1/0237 482/51 |
| 7,601,104 B2* | 10/2009 | Agrawal | ................. | A61G 5/14 482/69 |
| 7,938,756 B2* | 5/2011 | Rodetsky | ............. | A61H 1/0262 135/67 |
| 8,177,688 B2* | 5/2012 | Burnfield | ............. | A61H 1/0214 482/1 |
| 8,771,208 B2* | 7/2014 | Agrawal | ................ | A61H 1/024 601/33 |
| 2002/0026130 A1* | 2/2002 | West | ..................... | A61F 5/0102 601/23 |
| 2004/0097330 A1* | 5/2004 | Edgerton | ............. | A61H 1/0237 482/1 |
| 2004/0116839 A1* | 6/2004 | Sarkodie-Gyan | ...... | A61H 3/008 601/35 |
| 2005/0101448 A1* | 5/2005 | He | ........................ | A61H 1/0237 482/54 |
| 2006/0097557 A1* | 5/2006 | Tholkes | ................. | A47C 9/002 297/330 |
| 2007/0179561 A1* | 8/2007 | Embrey | ............. | A61N 1/36003 607/49 |
| 2008/0051258 A1* | 2/2008 | Schmehl | ............ | A63B 22/0015 482/52 |
| 2008/0255488 A1* | 10/2008 | Agrawal | .......... | A63B 21/00181 602/23 |
| 2010/0121232 A1* | 5/2010 | Sankai | ................... | A61H 3/008 601/23 |
| 2010/0222716 A1* | 9/2010 | Olsen | .................... | A61H 3/008 601/26 |
| 2010/0248903 A1* | 9/2010 | Cardile | ................ | A61H 1/0262 482/51 |
| 2010/0270771 A1* | 10/2010 | Kobayashi | ............. | A61H 3/008 280/210 |
| 2010/0285929 A1* | 11/2010 | Bayerlein | ............ | A61H 1/0237 482/54 |
| 2010/0298102 A1* | 11/2010 | Bosecker | ............... | A61H 1/005 482/54 |
| 2011/0071442 A1* | 3/2011 | Park | ..................... | A61H 1/0262 601/35 |
| 2011/0086742 A1* | 4/2011 | Burnfield | ............. | A61H 1/0214 482/7 |
| 2011/0201978 A1* | 8/2011 | Jeon | ..................... | A61G 5/045 601/35 |
| 2011/0205067 A1* | 8/2011 | Konishi | ................. | A61H 3/008 340/573.1 |
| 2012/0004581 A1* | 1/2012 | Dinon | ................. | A61H 1/0237 601/23 |
| 2012/0253242 A1* | 10/2012 | Lee | ...................... | A61G 7/1015 601/35 |
| 2013/0226048 A1* | 8/2013 | Unluhisarcikli | ......... | A61H 3/00 601/34 |
| 2013/0274640 A1* | 10/2013 | Butters | ................... | A61H 3/008 601/35 |

* cited by examiner

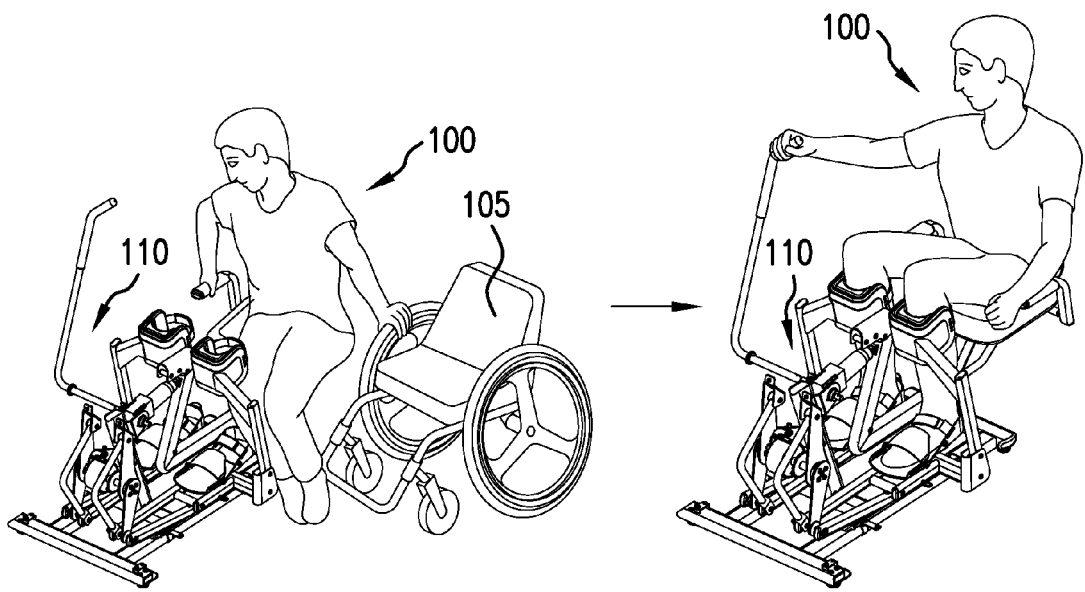
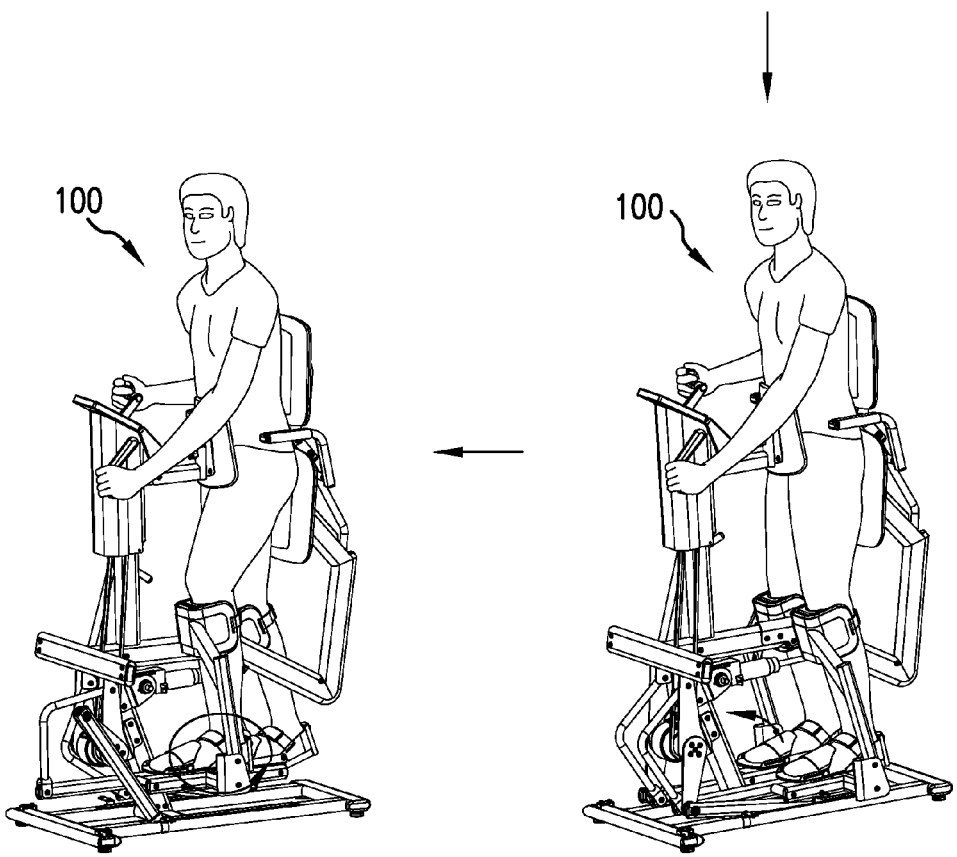
FIG.1A   FIG.1B
FIG.1D   FIG.1C

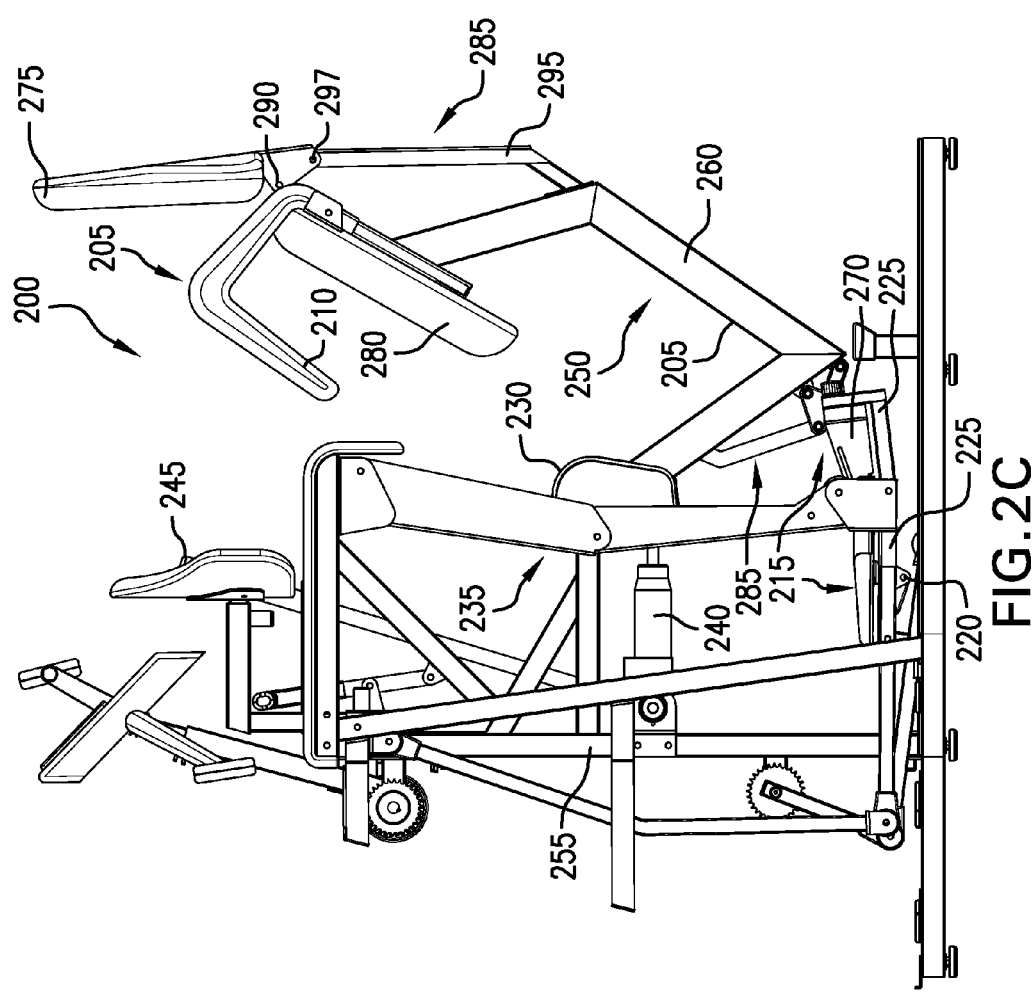

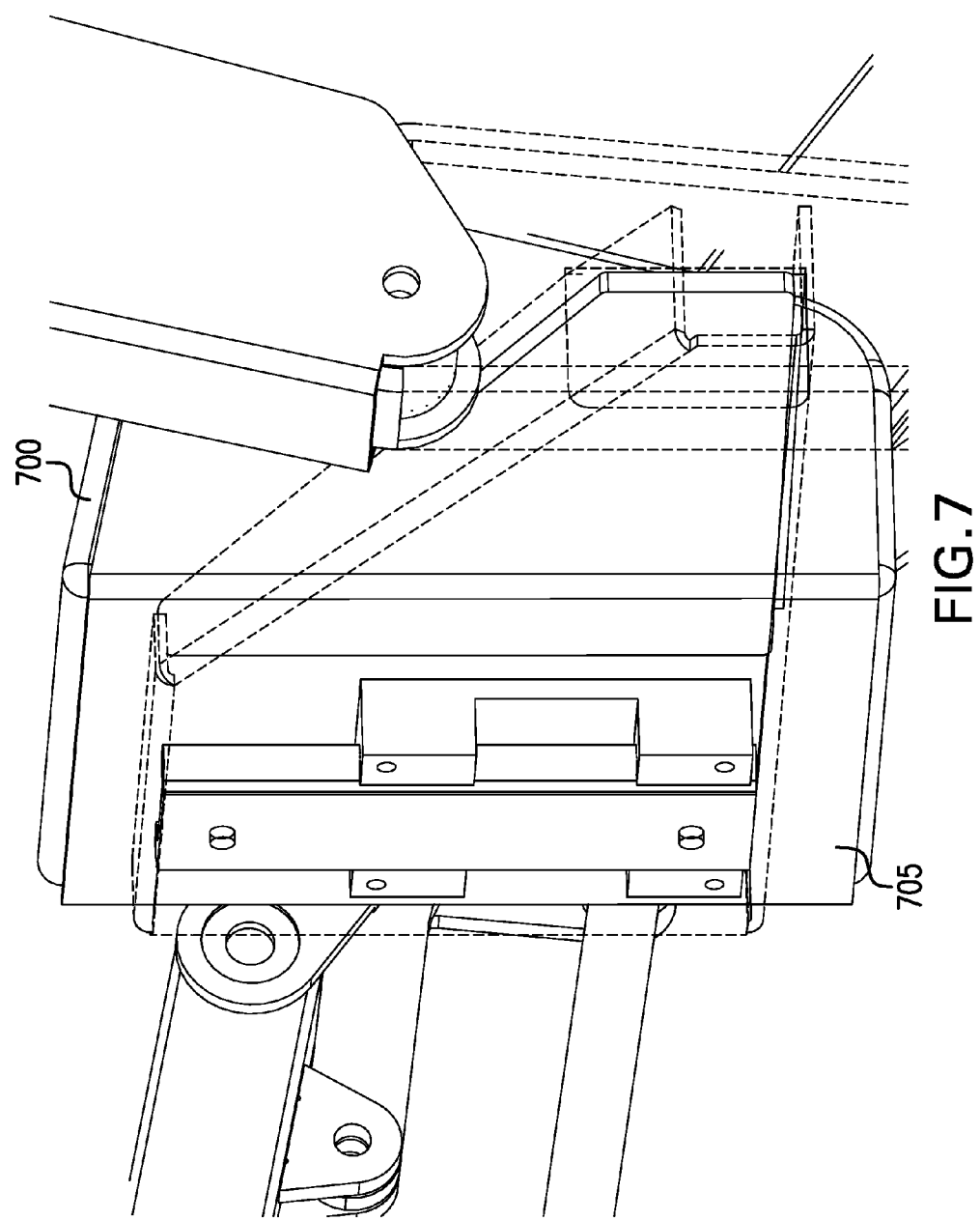

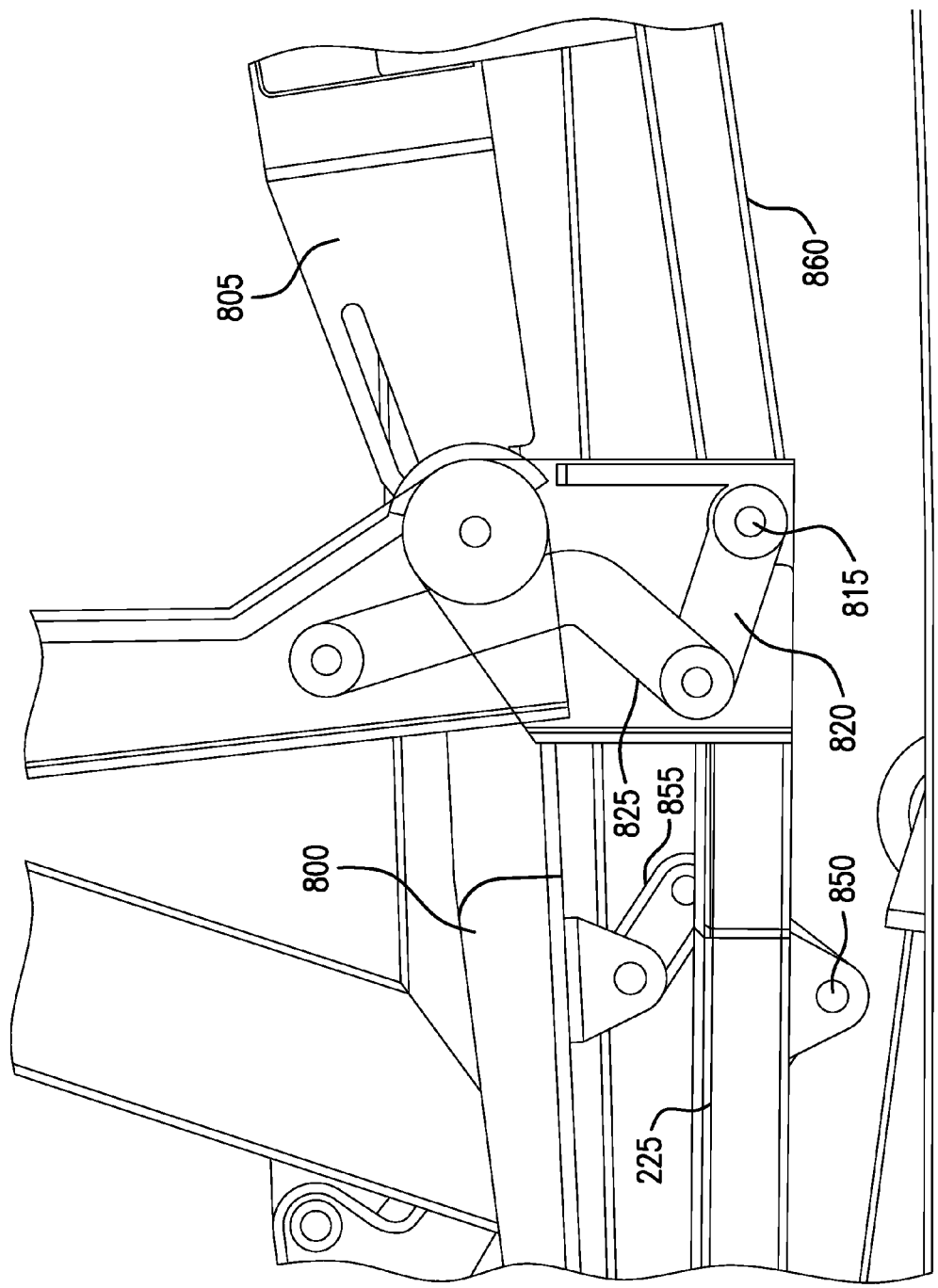

MULTI-MODAL GAIT-BASED NON-INVASIVE THERAPY PLATFORM

CROSS-REFERENCE TO RELATED APPLICATIONS

This application claims the benefit of U.S. Provisional Application Ser. No. 61/915,834, titled "Natural-Gait Therapy Device," filed by Alan Tholkes et al., on Dec. 13, 2013. The entirety of the foregoing application is hereby incorporated by reference.

TECHNICAL FIELD

Various embodiments relate generally to therapy devices, and more specifically to therapy devices for people with spinal cord injuries.

BACKGROUND

There are approximately twelve thousand spinal cord injuries (SCI) per year in the United States alone. The average age of an injured person is twenty-eight years old. There are approximately three-hundred thousand people with SCIs in wheelchairs in the United States. In addition to SCIs, there are also many thousands of cases of strokes as well as thousands of cases of MS diagnoses each year in the United States. Furthermore, many other neurological problems afflict people and confine them to wheelchairs. The numbers of such cases world-wide is commensurately larger yet.

Providing such physically afflicted individuals an ability to stand may help maintain and improve their health. Walking therapy may restore function in SCI individuals and in those who have suffered paralyzing strokes. The beneficial results from walking therapy may be enhanced if the paralyzed individual can consistently and regularly perform the therapy. Mental health benefits may accrue as well to SCI individuals who may independently exercise or practice therapy.

SUMMARY

Apparatus and associated methods relate to a knee-position control system having a knee engagement pad, a lower-leg control member and an upper-leg control member, the knee engagement pad configured to naturally position a user's knee in response to movement of a foot-rest of a natural-gait therapy system. In an illustrative embodiment, the upper-leg control member may pivot about a point substantially axially coincident with a user's hip. In some embodiments, the upper-leg control member may be pivotally coupled to the lower-leg control member at a pivot point substantially axially coincident with a user's knee. The lower-leg control member may be pivotably coupled to the foot rest at a pivot point substantially axially coincident with a user's ankle. The knee-position control system may advantageously position a user's knee in a natural position relative to both the user's ankle and the user's hip, in response to movement of the user's foot.

Apparatus and associated methods may relate to a sit-to-stand therapy device having a pivotable seat assembly coupled to a stationary frame via a U-shaped step-over beam, the pivotable seat assembly configured to pivot between a sitting position and a standing position. In an illustrative embodiment, when a user is sitting on the seat pivoted to the sitting position, the U-shaped step-over beam may travel from a pivotable frame connection substantially collinear with the user's knee down to a ground proximal elevation where it longitudinally traverses toward the seat, and then up to a seat connection. In some embodiments the sit-to-stand therapy device may have knee pads and foot rests configured to engage a user's knees and feet, respectively, when seated. In an exemplary embodiment, a dynamically adjustable seat back may maintain vertical engagement with a user's back throughout a transition from the sitting position to the standing position.

Apparatus and associated methods may relate to a knee-position control system having a knee engagement pad, a lower-leg control member and an upper-leg control member, the knee engagement pad configured to naturally position a user's knee in response to movement of a foot-rest of a natural-gait therapy. In an illustrative embodiment, the upper-leg control member may be pivotally connected to a pivot point substantially axially coincident with a user's hip. In some embodiments, the upper-leg control member may be pivotally coupled to the lower-leg control member at a pivot point substantially axially coincident with a user's knee. The lower-leg control member may be coupled to the foot rest at a pivot point substantially axially coincident with a user's ankle, for example. The knee-position control system may advantageously position a user's knee in a natural position relative to both the user's ankle and the user's hip, in response to movement of the user's foot.

Apparatus and associated methods may relate to a natural-gait therapy device for enabling a user with a Spinal Cord Injury (SCI) to independently transfer to the device, lift a user's body to a standing position and hand-power a natural-gait motion of the user, the device having a transfer mode, a standing mode, and a natural-gait mode, wherein, when in the transfer mode, a seat and foot rests are configured in substantially similar positions as a standard wheelchair's corresponding seat and foot rests to facilitate a lateral transfer of the user from an adjacent wheelchair to the device, wherein, when the user actuates a lifting module, the seat lifts and rotates to a standing position, and when the user actuates a gait module, the user's body is locomoted in a natural-gait. In an exemplary embodiment, the natural-gait therapy device may advantageously provide positive health benefits to individuals with SCIs.

Apparatus and associated methods may relate to a natural-gait therapy device for enabling a user with a Spinal Cord Injury (SCI) to independently transfer to and from the device by providing one or more base support members within a footprint of the seat, wherein the base support members are configured to receive the front wheels of a wheelchair that is positioned adjacent to a seat of the therapy system, the wheelchair being rotated an acute angle with respect to a seat of the therapy system so that the front wheels project in front of a portion of the seat of the therapy system. In some embodiments, a seat support member may be within the footprint of the seat as well. In an exemplary embodiment, the natural-gait therapy device may advantageously facilitate transfers to and from the device for individuals with SCIs.

Apparatus and associated methods may relate to a natural-gait therapy device for enabling a user with a Spinal Cord Injury (SCI) to independently power a lifting of the user's body from a transfer position to a secure standing position, the natural-gait therapy device having a seat support member having a transfer position and a standing position wherein, when in the transfer position, the seat support member extends from a cage in front of the user to the seat via a step-over extension member, wherein the step-over extension member is disposed between an elevation below a top of the footrests to avoid encumbering the translation of the user's feet between footrests and the user's foot position prior to entry or upon exit of the system. In some embodiments, the seat support member may pivot a seat about a pivot point substantially collinear with the pivot points of a user's knees.

Apparatus and associated methods may relate to a natural-gait therapy device for enabling a user with a Spinal Cord Injury (SCI) to independently power a lifting of the user's body from a transfer position to a standing position, the natural-gait therapy device having a seat-back attitude control mechanism that maintains the seat-back in a substantially vertical attitude throughout a travel from a transfer position to a standing position. In some examples, a back-support may be pivotably coupled to a seat, wherein a seat-back attitude control mechanism maintains the seat-back in a substantially vertical orientation as the seat is raised and rotated during the lifting operation. In some examples, a torso stabilization member may provide front stabilization of a user's torso. The seat, seat-back and torso stabilization member may advantageously provide multiple-point standing support for a user who may have limited control of a lower body.

Apparatus and associated methods may relate to a natural-gait therapy device for enabling a user with a Spinal Cord Injury (SCI) to independently transition between a locked standing position and a user controlled coordinated natural-gait movement, the method including an unlocking of a left and a right foot movement members, rotating one of the unlocked left and right movement members to a half-period gait position that is 180 degrees out of phase with the un-rotated one of the left and right movement members, coupling the left and right movement members in the 180 degree phase differential orientation, and rotating both left and right leg movement members in a natural-gait motion. In some embodiments, the left and right movement members may be uncoupled to permit a gravity assisted return to a standing position. The transition between the standing and the natural-gait motion may facilitate a user to stand before or sit after performing natural-gait therapy.

Various embodiments may achieve one or more advantages. For example, some embodiments may provide a natural-gait therapy device having seat into which a user may easily transfer to and from. Some embodiments may enable a user to stand independently using a hand powered operation. Some embodiments may facilitate a user to independently locomote the user's body in a natural-gait. In an exemplary embodiment, a bio stimulation of locomotion muscles may be cyclically coordinated with the natural-gait motion, for example, as a function of the angular position within a gait-cycle. The bio-stimulation may include periodic electrical stimulation signals that are generated and applied to the user.

In an exemplary embodiment, a user may independently perform natural-gait therapy, without requiring assistance of another person. Such independence may promote a higher frequency of therapy for the user. In some embodiments, the cost of therapy may be reduced. Reducing therapy costs may again promote the frequency of therapy. Independent use and/or reduced costs may result in better health of the user. In some embodiments, natural-gait therapy may provide for a recovery of some body function for the user. Users may also enjoy satisfaction of natural-gait movements. Such satisfaction may promote the psychological well-being of users. In various examples, some embodiments may have a footprint and form factor that readily permits installation in a typical residential home.

The details of various embodiments are set forth in the accompanying drawings and the description below. Other features and advantages will be apparent from the description and drawings, and from the claims.

BRIEF DESCRIPTION OF THE DRAWINGS

FIGS. 1A-1D depicts a sequence of vignettes depicting different stages of use of an exemplary natural-gait therapy device.

FIGS. 2A-2E depict an exemplary natural-gait-therapy device at various stages of lifting a user from a transfer position to a standing position.

FIG. 7 depicts a close-up view of an exemplary knee engagement member.

FIGS. 8A-8B depict a close-up view of a heel lift system.

FIGS. 17A-18B depict an exemplary zero-degree safety system.

FIGS. 18A-18B depict an exemplary zero-degree safety system.

DETAILED DESCRIPTION OF ILLUSTRATIVE EMBODIMENTS

To aid understanding, this document is organized as follows. First, an exemplary natural-gait therapy device is briefly introduced with reference to FIGS. 1A-1D. These figures will aid a discussion about the various steps of use through which a user may sequence. Second, with reference to FIGS. 2A-3 the discussion turns to exemplary embodiments that illustrate some of the features of an exemplary natural-gait therapy device associated with a transfer operation. This discussion will highlight novel aspects an exemplary implementation that facilitates a transfer to and from a wheelchair. This discussion will also describe some of features that provide a body to be secure in the standing position. Then, with reference to FIGS. 4A-4D, a foot transition from a side-by-side standing position to an oppositional foot position used in a natural-gait will be described. This will be followed by a discussion of locomotion of a natural-gait therapy, with reference to FIGS. 5A-8. Then, with reference to FIGS. 9A-9B, an exemplary transmission module will be described. The exemplary transmission module may provide the modality of a locked transfer/standing leg position, an oppositional synchronization of feet during a natural-gait mode, as well as a transition between modes.

Figure 12A:
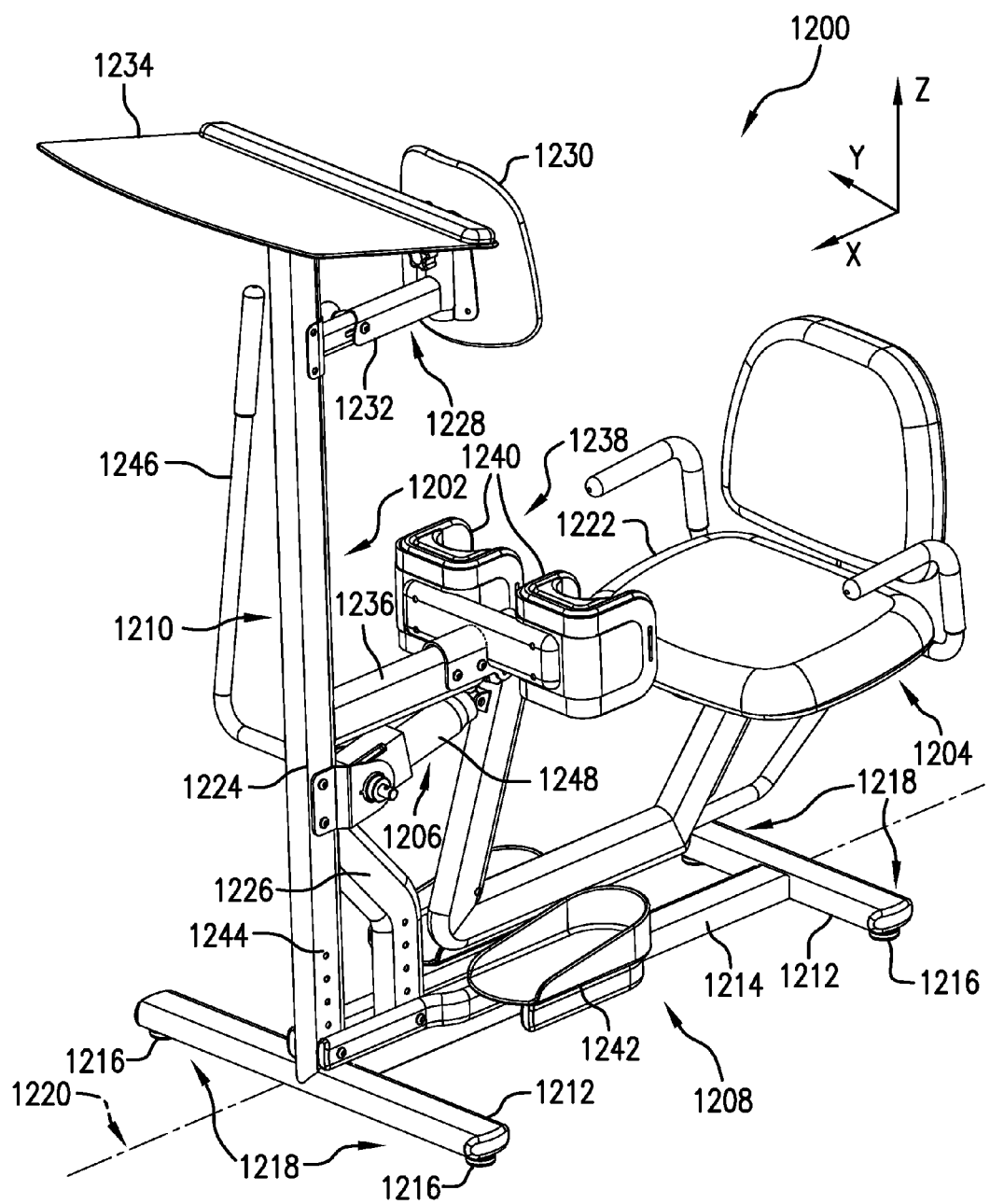
FIGS. 12A-12D depict an exemplary sit-to-lift therapy device.
Figure 12B:
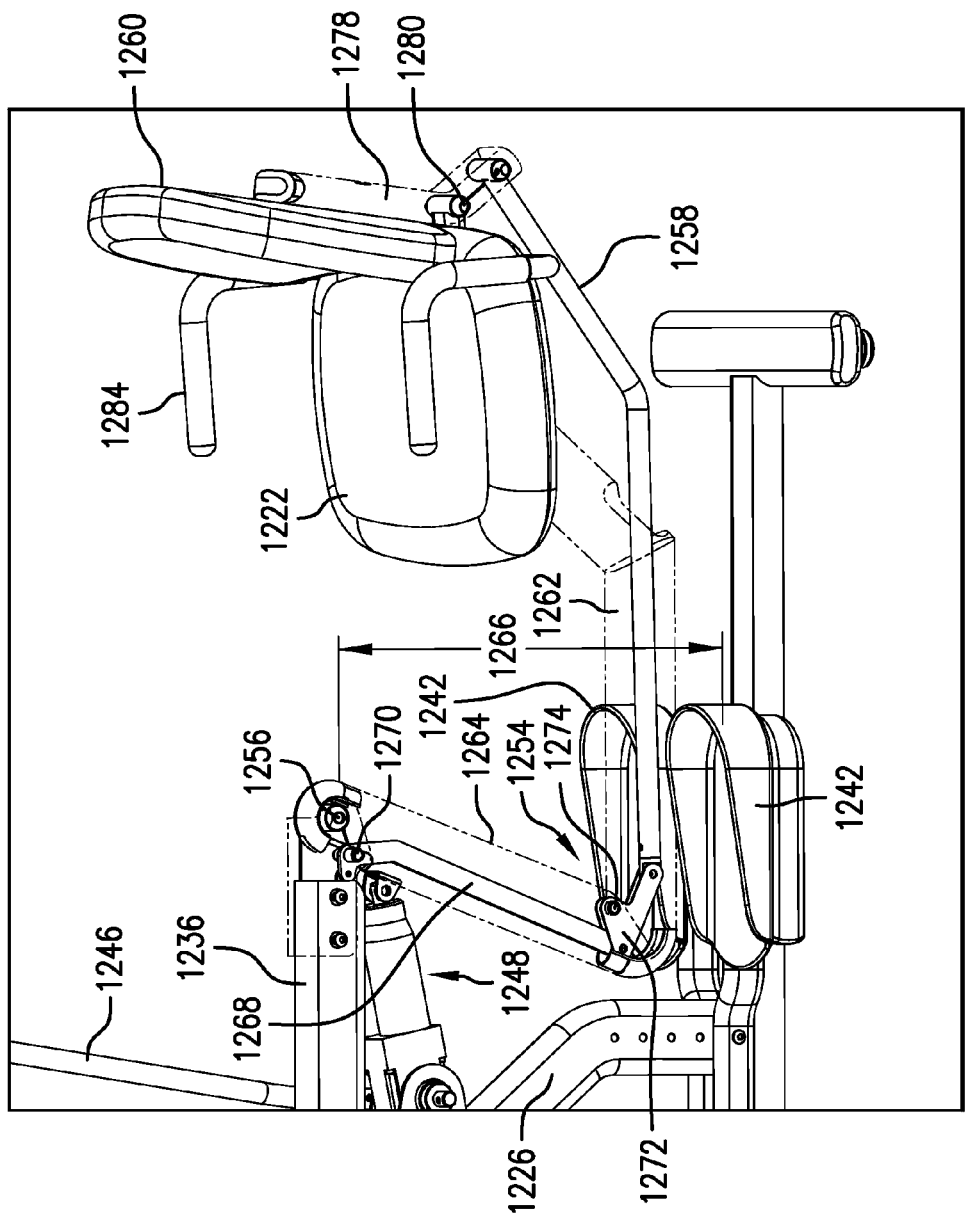
Figure 13A:
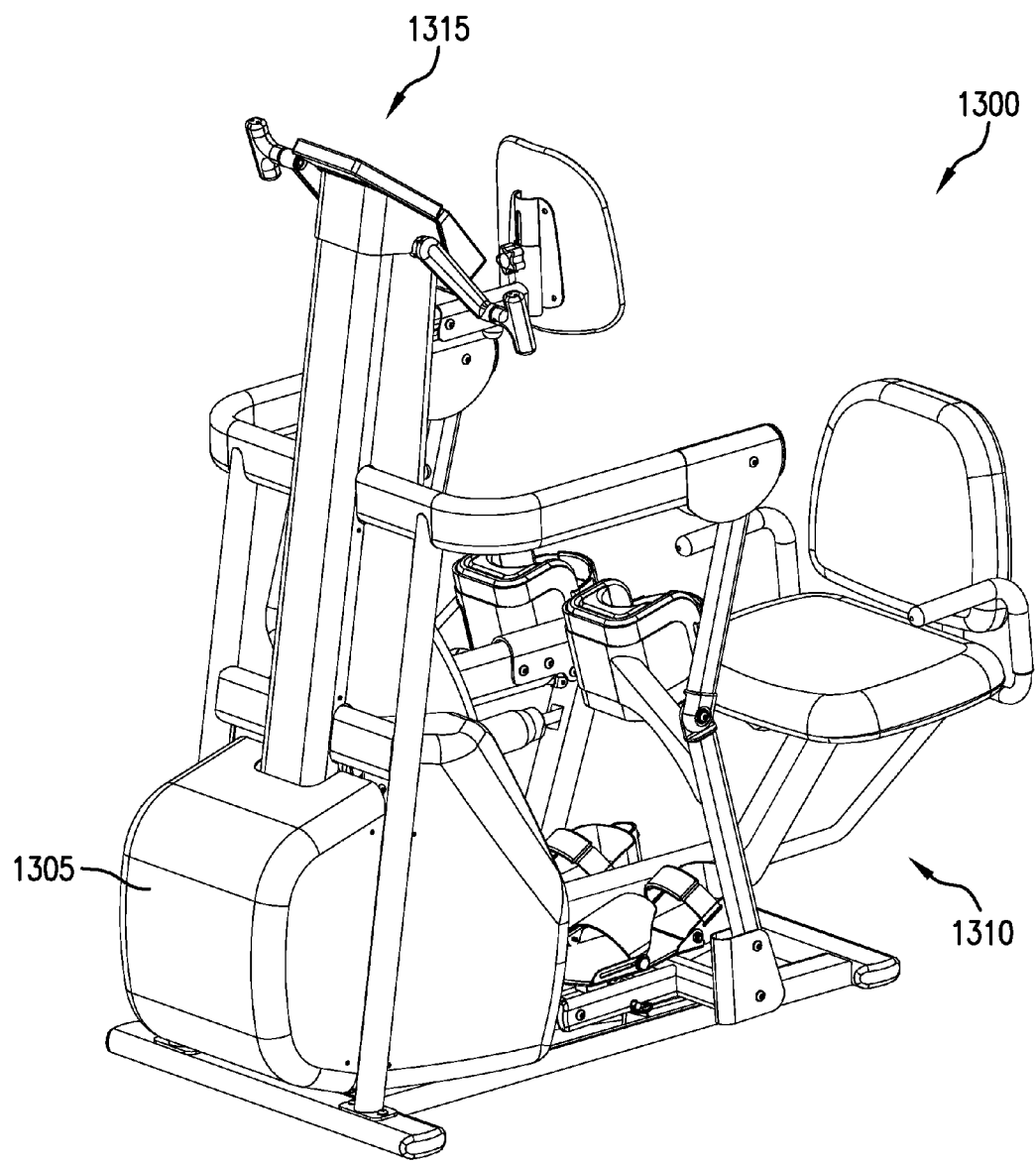
FIGS. 13A-13B depicts a perspective view of an exemplary natural-gait therapy system.
Figure 13B:
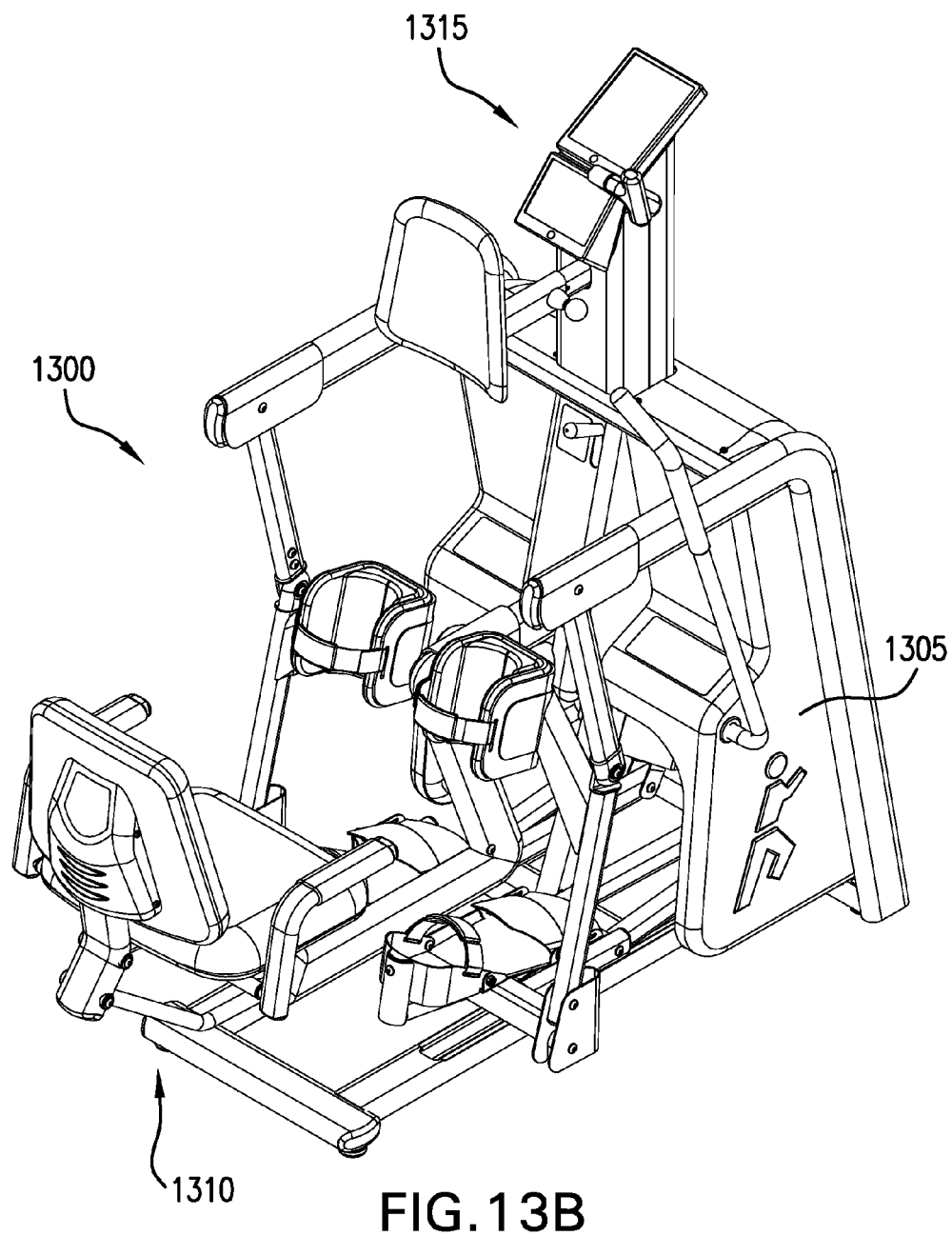

The sit-to-stand operation will be then revisited and described, with reference to FIGS. 12A-12B. To protect user's from moving parts, exemplary natural-gait therapy devices may have protective coverings. With reference to FIGS. 13A-13B, two exemplary natural gait therapy devices are depicted, each with a different style of protective covering. Then with reference to FIGS. 14A-14D, an exemplary natural-gait locomotion system is described. Each of four subsystems that coordinate a natural-gait locomotion will be discussed: a toe-position control system, a forefoot-angle control system, knee-position control system, and a heel-lift control system. Then discussion will focus on the exemplary knee-position control system and its hyperextension protection subsystem, with reference to FIG. 15. Before a user performs natural-gait therapy, the user's feet may be transitioned from a side-by-side position to an out-of-phase walking position. An exemplary stand-to-walk transition module will be described, with reference to FIGS. 16A-16B. After performing natural-gait therapy and before returning to a sitting position, the user's feet should be returned to a side-by-side position.

A safe-sitting interlock system will be described, with reference to FIGS. 17A-18B, in which a user's the therapy device returns the foot rests to a side-by-side position before lowering a seat bottom to a sitting position. Then, with reference to FIGS. 19-23 and 25-26, exemplary multi-modal functions (e.g. coordinated muscle stimulation, nerve therapy, etc.) will be described. Finally, Discussion will follow with a description of an exemplary foot rest with coordinated operation with a treadmill, with reference to FIGS. 24A-B.

An exemplary natural-gait therapy device may assist a user to independently perform natural-gait therapy by facilitating one or more of the following seven steps. A first step often may include transferring from a wheelchair to the seat of a natural-gait therapy device. A second step may include lifting the user from a transfer position to a standing position. A third step may include transitioning from a side-by-side foot standing position to an opposition-oriented foot natural-gait position. A fourth step may include locomoting the body to perform a natural-gait motion. A fifth step may include transitioning from the opposition-oriented foot natural-gait position to the side-by-side foot standing position. A sixth step may include descending from a standing position to a transfer position. A seventh step may include transferring from the natural-gait therapy device back into the wheelchair.

FIGS. 1A-1D depicts a sequence of vignettes depicting different stages of use of an exemplary natural-gait therapy device. In FIG. 1A, a user 100 is transferring from a wheelchair 105 to an exemplary natural-gait therapy device 110. In FIG. 1B, the user 100 is lifting the body from a transfer position to a standing position. In FIG. 1C, the user 100 is transitioning the leg position from a side-by-side standing feet position to an opposition-located natural-gait feet position. And in FIG. 1D, the user 100 is using the user's arms to power the user's body through repeating natural-gait cycles. The user 100 may "unwind" this process when finished with a therapy session, by going through the above steps in a reverse order to return to the wheelchair 105.

Figure 2A:
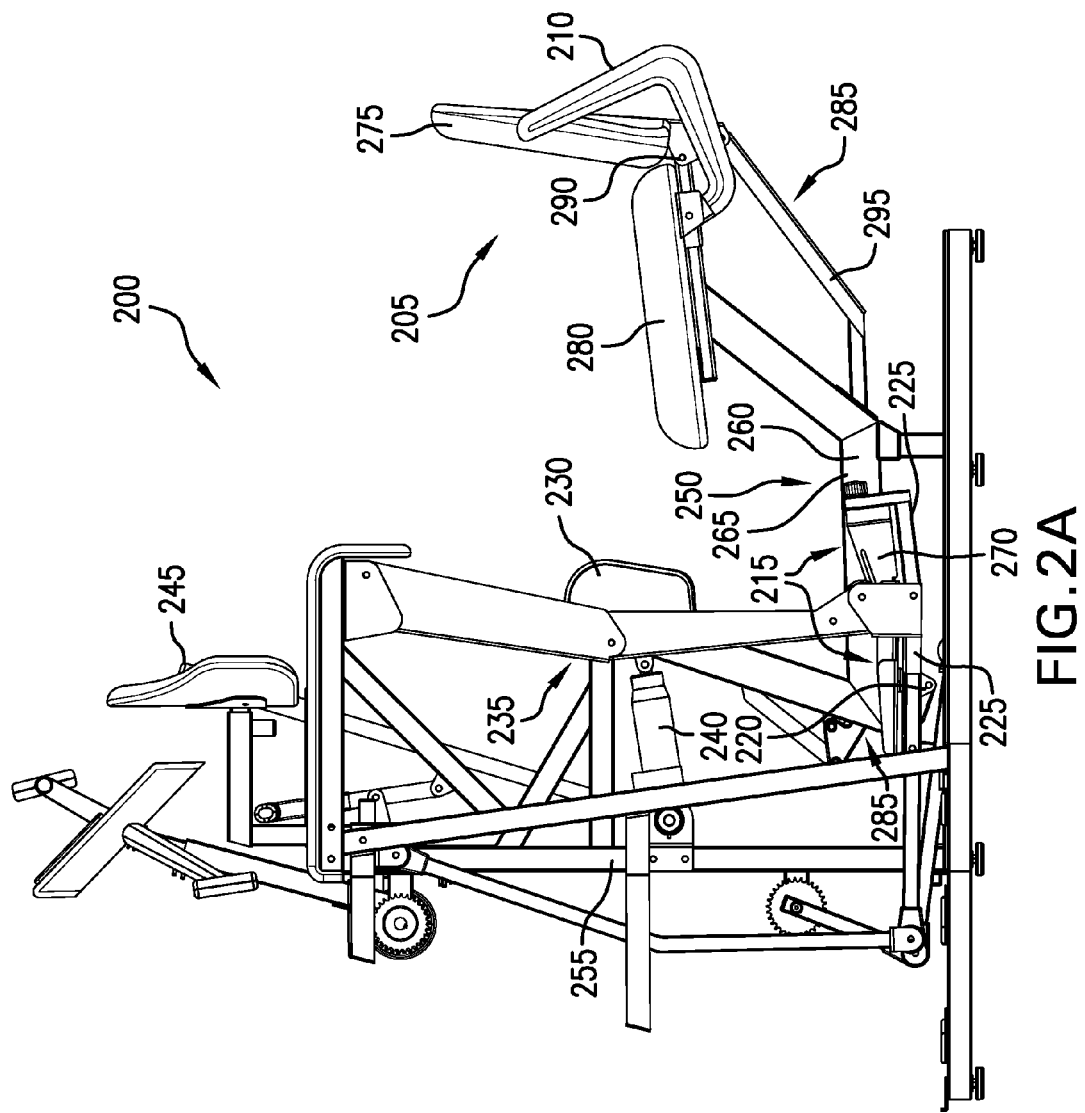

A therapy session may begin by transferring from the wheelchair 105 to a natural-gait therapy device 110. Transferring methods may vary depending on many factors such as: the size and/or design of the wheelchair; the level of function that the transferring person has (for example, strength in upper limbs); whether the transfer is independent or assisted; and personal preferences. In FIG. 2A, an exemplary natural-gait therapy device 200 is depicted in a transfer mode. In the transfer mode, a seat 205 of the natural-gait therapy device 200 may is depicted in a transfer position. In the transfer position, an armrest 210 may be pivoted back so that the armrest 210 is not interposed between the wheelchair 105 and the seat 205 of the natural-gait therapy device 200. In the transfer mode, footrests 215 may be locked into a side-by-side foot position. The wheelchair 105 may be positioned adjacent to the seat 205 of the natural-gait therapy device 200. The wheelchair 105 may be maneuvered until it is approximately parallel with the adjacent seat 205, with the front of the wheelchair's seat aligned with the front of the seat 205 of the natural-gait therapy device 200. Alternatively, the transfer may be angled, with the wheelchair at an acute angle with respect to the adjacent seat. The transferee may push footrests of the wheelchair 105 out of the way during a transfer operation.

If the user should have enough upper body strength, the user may support the user's body using the user's arms. In some instances, the user may support the body using one or more of the following supports: i) the seat of the natural-gait therapy device; ii) the seat of the wheelchair; iii) an arm support of the natural-gait therapy device; iv) an arm support of the wheelchair; v) an auxiliary support member; and/or vi) assistance from another person or persons. The user may support the user's upper body sufficiently to at least permit the body to slide over any intervening obstacles between the wheelchair's seat and the seat 205 of the natural-gait therapy device 200. One such intervening object may be a side-rail of the wheelchair and/or the wheelchair's wheel.

In some embodiments, the user may use a rope or handle suspended from above to assist in the transfer process. In various embodiments, various transfer auxiliary support members may be used. In some embodiments, such transfer assist members may be movable from an assisting position to a stowing position. For example, a suspended assisting handle may be movable so as to provide suspended support above the seat 205 of the natural-gait therapy device 200.

The suspended assisting handle may then be moved so that it may no longer remain above the seat 205 after the user transfers to the natural-gait therapy device 200. In some embodiments, a folding mechanism may facilitate movement from transferring position to a stowing position. In an exemplary embodiment a pivot may be used to facilitate movement between a transfer mode to a stowage mode.

A difference between a seat height of the seat 205 of the natural-gait therapy device 200 and the seat of a wheelchair may be small. A large difference in seat height may make transfer to or from the natural-gait therapy device 200 difficult. Many adult sized-wheelchairs may have a seat height of approximately twenty inches above ground level. In some embodiments, a difference between a seat height of the seat 205 of the natural-gait therapy device 200 and a wheelchair's seat may be less than three inches. In some embodiments, the difference may be less than two inches. In some embodiments, the difference may be less than one and a half inches inch. In some embodiments, the seat height of the seat 205 of the natural-gait therapy device 200 may be substantially equal to the seat height of a standard wheelchair's seat. In various embodiments, the seat 205 of the natural-gait therapy device 200 may have a height adjustment member for adjusting the seat's height. For example, in some embodiments, a seat support member may have a series of adjustment holes, and a seat post may be inserted into the seat support member and secured using one of the adjustment holes. In some embodiments, a pneumatic piston may provide height adjustment. In some embodiments, a screw member may provide height adjustment.

After transferring the user's body from the wheelchair 105 to the seat 205 of the natural-gait therapy device 200, the user may transfer the user's legs to the foot rests 215 of the natural-gait therapy device 200. To facilitate the transfer of the user's legs to the leg rests 215, a height of the foot rests may be near to the ground when in the transfer position. In some embodiments, the foot rests may be within six inches of ground level when in the transfer position. In various embodiments, the foot rests may be within 5 inches, 4 inches, 3.5 inches, 2 inches, or even closer to ground level when in the transfer position. In the depicted embodiment, the foot rests 215 are depicted having a height adjustment member 220. The height adjustment member 220 may provide series of apertures, through which a pin may secure the foot rest 215 to a foot motion platform 225.

Various body securement devices may secure the body, now transferred, to the natural-gait therapy device 200. For example, foot straps may secure the transferred feet into the foot rests 215. Such foot straps may use hook and loop fasteners, for example. In some examples, buckles may be used for securing the user's foot to the foot rest 215. In some embodiments, laces may be used to secure feet to the foot rests 215. The foot rests 215 may have a coating for promoting friction between the user's feet and the foot rests. In one exemplary embodiment, the foot rest 215 may include a boot for securing the feet of a user. A seat belt may secure a user to the seat 205 of the natural-gait therapy device 200, for example. The arm rests 210 may provide lateral security to the body of a user when the armrests 210 are pivoted to a closed position on either side of the user. A user's knees may be secured in a knee rests 230 by a knee strap. In some embodiments, the knee strap may cross the back of the user's knee and secure the knee to the knee pad 230. Various methods of securing a user's knees to the knee pads may be used. In some embodiments, a hook and loop type of system may be used to secure the knee. In some embodiments, a strap and buckle may be used. Securing the knee to the knee pad 230 may couple the knee movement to the movement of a knee joint 235 of the natural-gait therapy device 200. This coupling may ensure that knee flexion of the user is performed in an anatomic fashion. Even if a user has no control of the leg, the knee may be prevented from movements in dangerous non-anatomic ways.

Figure 2B:
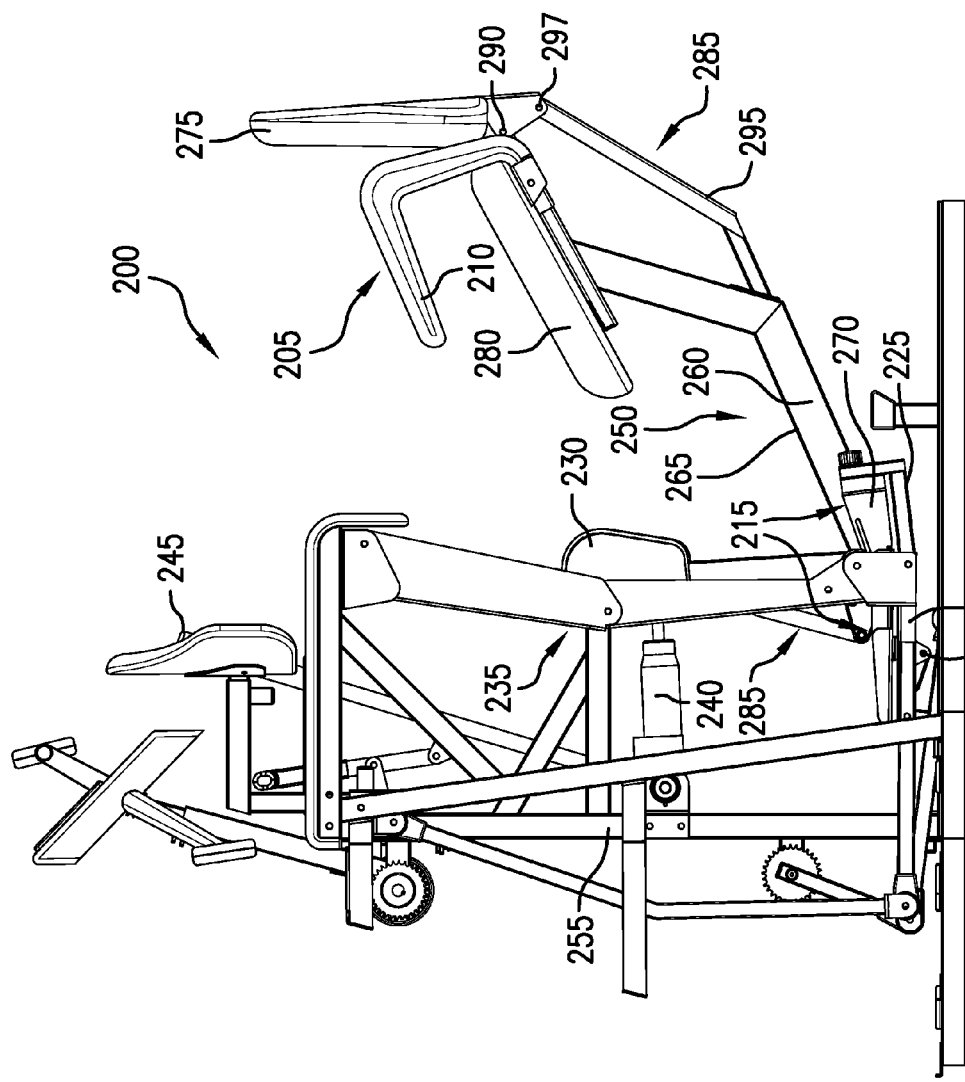
Figure 2D:
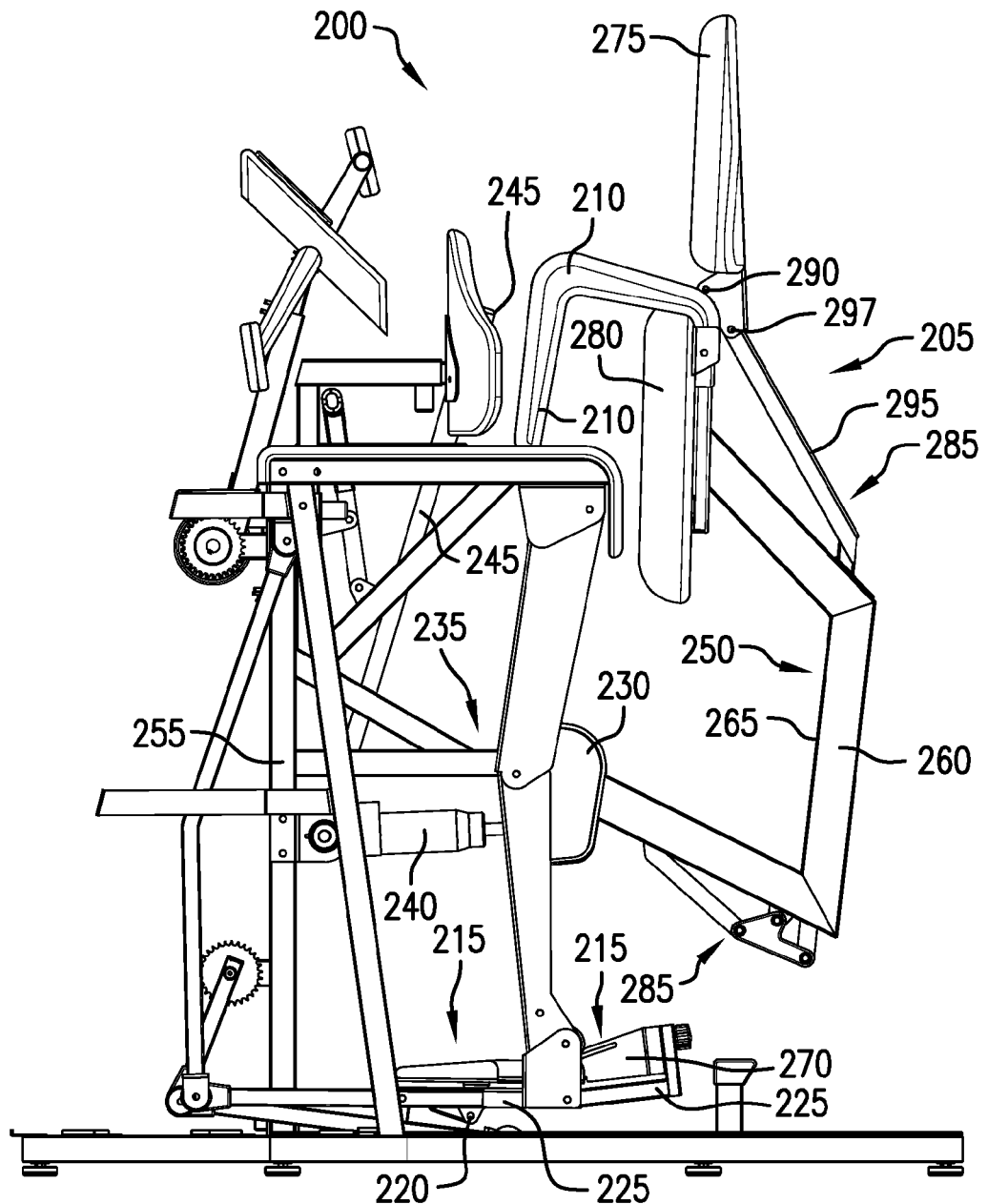
Figure 2E:
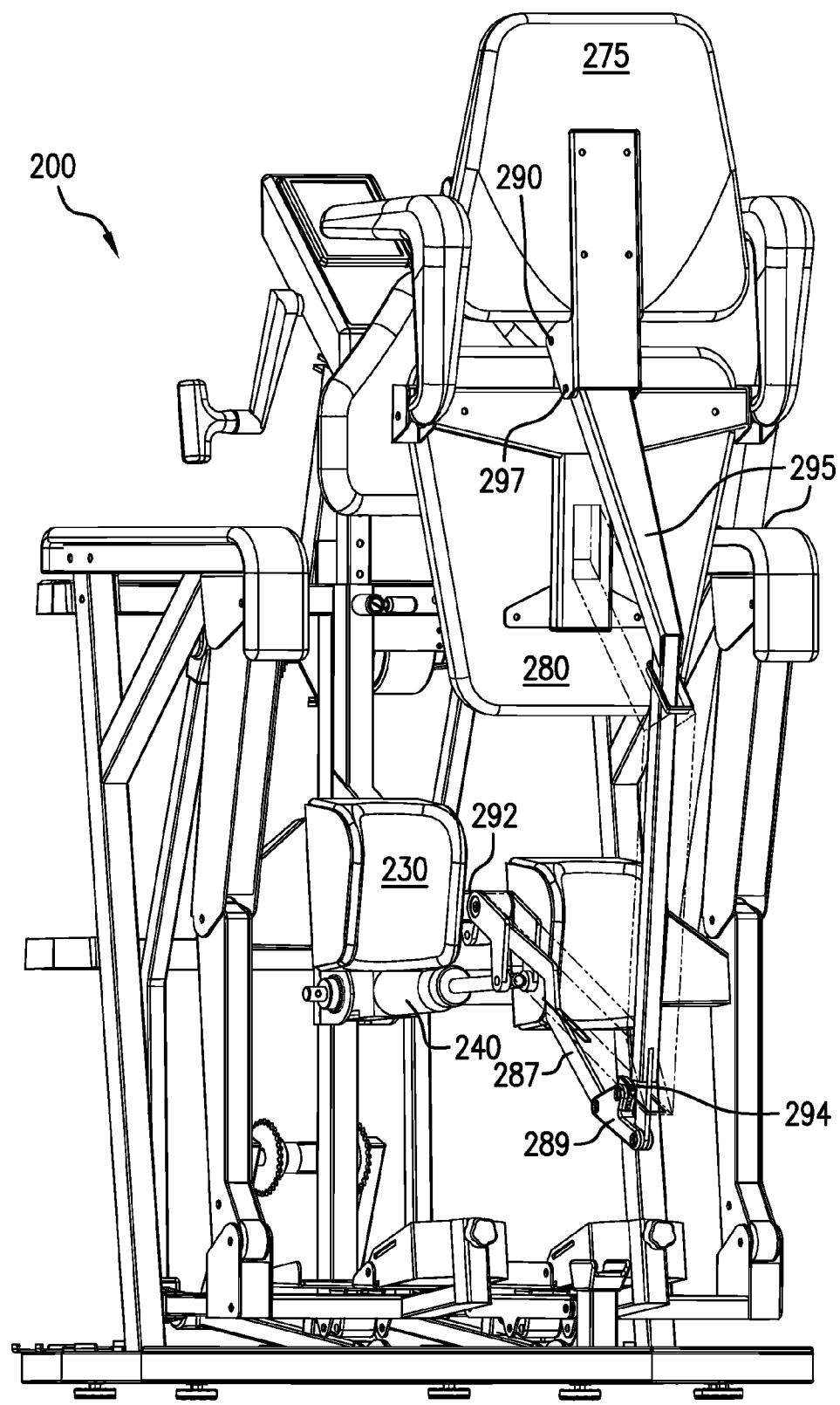

FIGS. 2A-2E depict an exemplary natural-gait-therapy device at various stages of lifting a user from a transfer position to a standing position. In FIG. 2A, the exemplary natural-gait therapy device 200 is depicted in a transfer position. In FIG. 2B, the exemplary natural-gait-therapy device 200 is depicted after the user may have lifted the seat 205 to a partially raised position, perhaps on the way to a full standing position. In FIG. 2C, the exemplary natural-gait therapy device 200 is depicted after the user may have lifted the seat 205 further toward the full standing position. In FIG. 2D, the exemplary natural-gait therapy device 200 is depicted after the user may have lifted the seat 205 to a full standing position. And in FIG. 2E, the natural-gait therapy device 200 is shown with selective members made transparent so as to better depict an exemplary seat-back attitude system 285.

In an exemplary embodiment, the lifting of the seat 205 and the user's body seated in the seat may be performed using various lifting mechanisms. In the FIGS. 2A-2E depictions, a hydraulic pump 240 may be used to lift the seat 205 and the user's body. In the depicted embodiment, a lifting handle 245 is coupled to the hydraulic pump 240. The lifting handle 245 may be positioned within the reach of the user throughout the lifting process, so that a user who has hand strength may independently lift the user's body from the transfer position to the standing position. In some embodiments, the lifting handle 245 may be long so as to provide mechanical leverage to facilitate the ease of lifting the seat 205 and user's body. Various means for lifting a seat 205 from a sitting position to a standing position may be employed. For example, an electric motor may be used to lift the seat 205 and the user's body. In an exemplary embodiment, a mechanical screw thread may be used to lift the user to a standing position. Some examples may use an electric hydraulic pump as a lifting means. In one example, and gas spring may be used as a means for lifting the seat 205 and user's body from a transfer position to a standing position.

In the depicted embodiment, a U-support member 250 couples the seat to a cage 255 of the natural-gait therapy device. The U-support member 250 may be pivotably coupled to the cage 255. The U-support member 250 may have a substantially linear foot-crossing section 260 that, when in the transfer position, is substantially parallel to the ground and at a low elevation above the ground. When in the transfer position, as depicted in FIG. 2A, the foot-crossing section may have a top surface 265 that has an elevation less than four inches above a foot-bearing surface of the foot rests 215. This low elevation may advantageously facilitate a user's transfer of the user's foot across the foot-crossing section 260 during the transfer operation. In some embodiments, the elevation of the top surface 265 of the foot-crossing section 260 may be less than 2.5 inches above the foot-bearing surface of the foot rests 215. In an exemplary embodiment, the elevation of the top-surface 265 of the foot-crossing member 260 may be substantially equal to the elevation of the foot-bearing surface. In some embodiments, the elevation of the top surface 265 of the foot-crossing section 260 may be less than or equal to a top of a side-wall 270 of the foot rests 215.

In some embodiments, a pivot location of a pivotable coupling of the U-support member 250 to the cage 255 may be substantially in-line with knee pivot joints 235 of leg members of the natural-gait therapy device 200. The locations of these pivot locations being substantially in-line with each other may advantageously provide for pivoting of the body from the transfer position to the standing position in a manner that is consistent with the anatomical motion of the body pivoting about the knees. Pivoting about the knees may minimize the sheer force on the seat bottom of the user as the user pivots from a transfer position to a standing position. The adjustable foot-rest height may further promote these advantages by providing a means for coordinating the pivot location of a user's knees with the pivot location of the knee pivot joints 235 of a natural-gait therapy device 200.

In some embodiments, the seat 205 may be laterally adjustable. For example, a lateral adjustment mechanism may provide an adjustable forward/backward seat position. To accommodate a shorter user, for example, the foot rests 215 may be adjusted to a high position to ensure that the user's knees may be substantially coordinated with the knee pivot joints 235 of the natural-gait therapy device 200. The lateral seat position may be adjusted forward so that the arc traced by the forward portion of the seat during the lifting operation is smaller for a shorter person than for a taller person. Such lateral adjustability may provide better correlation between the anatomical movement of the user and that of the seat 205 of the natural-gait therapy device 200 during the lifting operation.

During the lifting operation as depicted in FIGS. 2A-2E, a seat-back 275 of the natural-gait therapy device 200 rotates relative to the seat-bottom 280 during the lifting operation. A seat-back attitude system 285 may provide this function. The depicted seat-back attitude system 285 includes a mechanical linkage system that provides for continuous attitude adjustment throughout the entire lifting operation. The seat-back 275 is pivotably coupled to the seat-bottom 280 at a pivot joint 290. An upper attitude control member 295 is pivotably coupled to the seat-back 275 at a pivot joint 297. The upper attitude control member 295 may rotate the seat-back 275 about the pivot joint 297. The seat-back 275 may be rigidly maintained in a substantially vertical attitude throughout the lifting operation.

When the upper attitude control member 295 is raised, the seat-back 275 may rotate forward about the pivot point 297. And when the upper attitude control member 295 is lowered, the seat-back 275 may rotate backward about the pivot point 297. The upper attitude control member 295 may be raised and lowered in response to the lifting of the U-support member 250. A lower attitude control arm 287 and an attitude control lever 289 may assist this operation. When the U-support member 250 is rotated from a transfer position toward a standing position, a distance between two pivot points 292, 294 increases. In response to that increase separation between the pivot points 292, 294, the attitude control lever 289 may rotate clockwise and lower the upper attitude control member 295 with respect to the U-support member 250. This lowering of the upper attitude control member 295 rotates the seat-back 275 open with respect to the seat-bottom 280. Both the upper attitude control member 295 and the lower attitude control member 287 are pivotably coupled to the attitude control lever 289 so as to perform the attitude control operation.

Various means of providing for a proper seat-back attitude during the lifting operation may be used. In some embodiments, a cable mechanism may provide for proper seat-back attitude during the lifting operation. In some embodiments, a cable distance may change in response to a rotation of a transfer/standing support member movement. In the depicted embodiment, the mechanical linkage is located substantially within the U-support member 250. Locating the mechanical linkage for the seat-back attitude system 285 within the U-support member 250 may minimize the interrupted space between a user's legs when the U-support member 250 is in the standing position.

Figure 3:
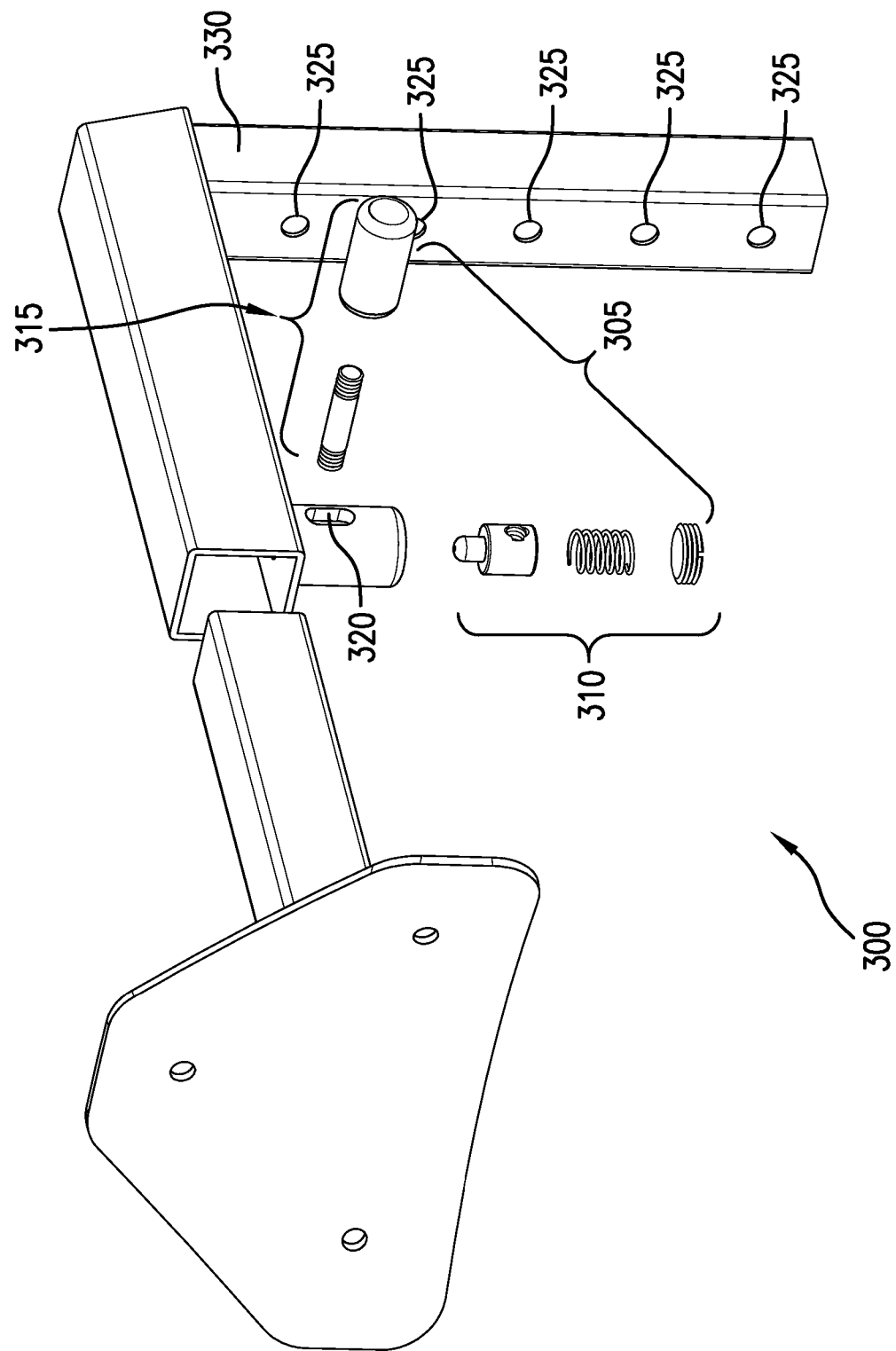
FIG. 3 depicts an exploded view of a torso stabilization member.

The user may be safely secured in the standing position using one or more securing means. The user's feet may be secured into the foot rests 215 using a foot securing means. The user's knees may be secured into the knee pads 230 using a knee securing means. The user may be secured into the seat 205 using a seat securing means. FIG. 3 depicts an exploded view of a torso stabilization member. In the FIG. 3 embodiment, a torso stabilization member 300 may include a forward/backward adjustment member 305. The torso stabilization member 300 may be adjustable to provide frontal support for individual users of different sizes. The depicted forward/backward adjustment member 305 may include a spring-loaded securing pin 310 and a pin-release lever 315. The spring-loaded securing pin 310 may project into one of a plurality of locating holes in a bottom side of the torso stabilization member 300. The pin-release lever 315 may be pulled in a downward direction by a user to release the spring-loaded securing pin 310. The pin-release lever 315 may travel in a slot 320 to provide the throw needed to bring the spring-loaded securing pin 310 free of the one of the plurality of locating hole in which it may reside.

In some embodiments, a vertical adjustment member may be used to facilitate a vertical position of the torso stabilization member 300. In the depicted embodiment, a plurality of locating holes 325 is shown on a vertical support torso support member 330. Each of the plurality of locating holes 325 may be captured by a securing pin similar to the spring-loaded securing pin 310 of the forward/backward adjustment member 305. Various means for adjusting a torso stabilization member 300 may be implemented. For example, a removable pin may be inserted into an adjustment aperture to capture one of a plurality of selectable position apertures in a complementary member. In some embodiments, a screw thread controlled adjustment means may be used.

In some embodiments, the torso stabilization member 300 may be concave as depicted in the FIG. 3 embodiment. This concave shape of the torso stabilization member 300 may provide some lateral stability to the user. In some embodiments, one or more lateral torso members may extend from the torso stabilization member 300 toward the seat-back 275. In some embodiments, securing straps may connect the torso stabilization member 300 to the seat-bottom 280 and/or seat-back 275 to provide lateral security for the user. Such securing straps may be fixed to the seat-back 275, for example. A free end of the securing strap may be releasably attached to the torso stabilization member 300, or to a strap connected to the torso stabilization member 300, for example. In an exemplary embodiment, a securing strap may releasably couple the torso stabilization member 300 to the armrests 210 of the seat 205. Lateral torso members may provide secure stability to users who have little control for maintaining a vertical body position.

Figure 4A:
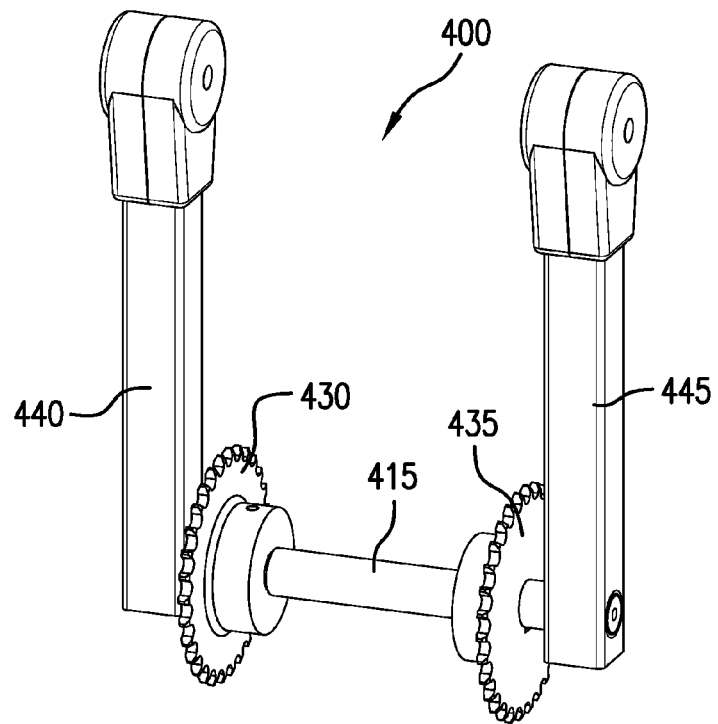
FIGS. 4A-4D depict an exemplary leg crank for a natural-gait therapy device.
Figure 4B:
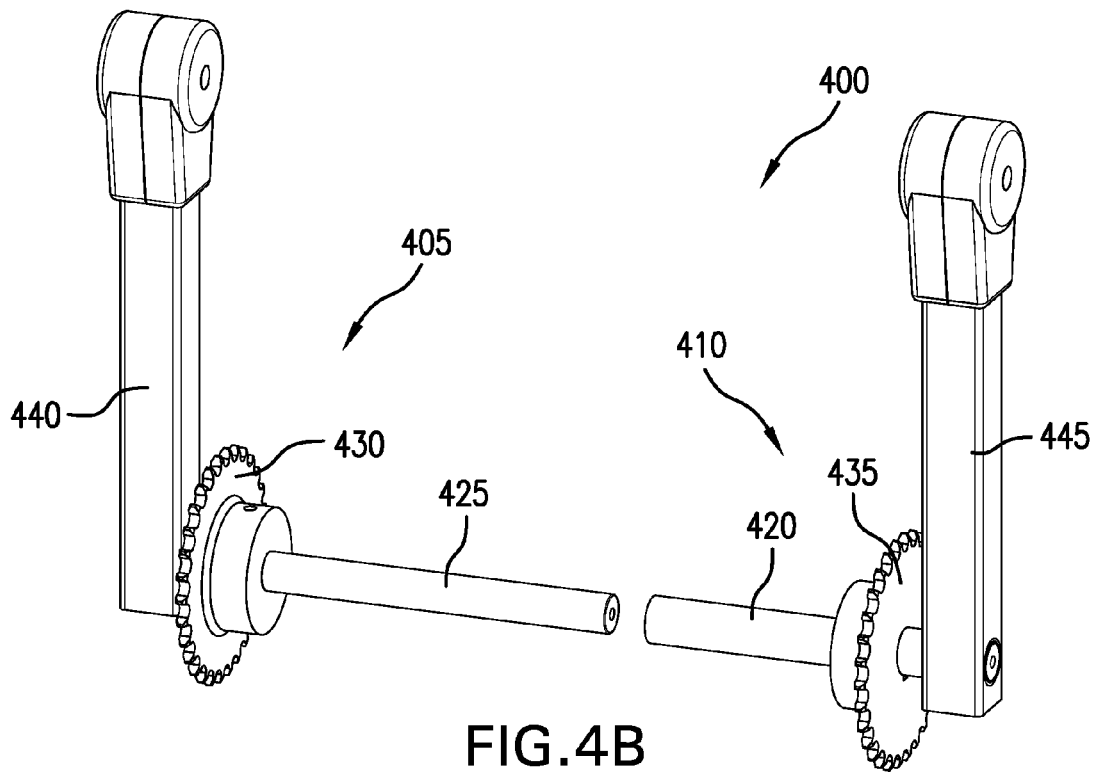
Figure 4C:
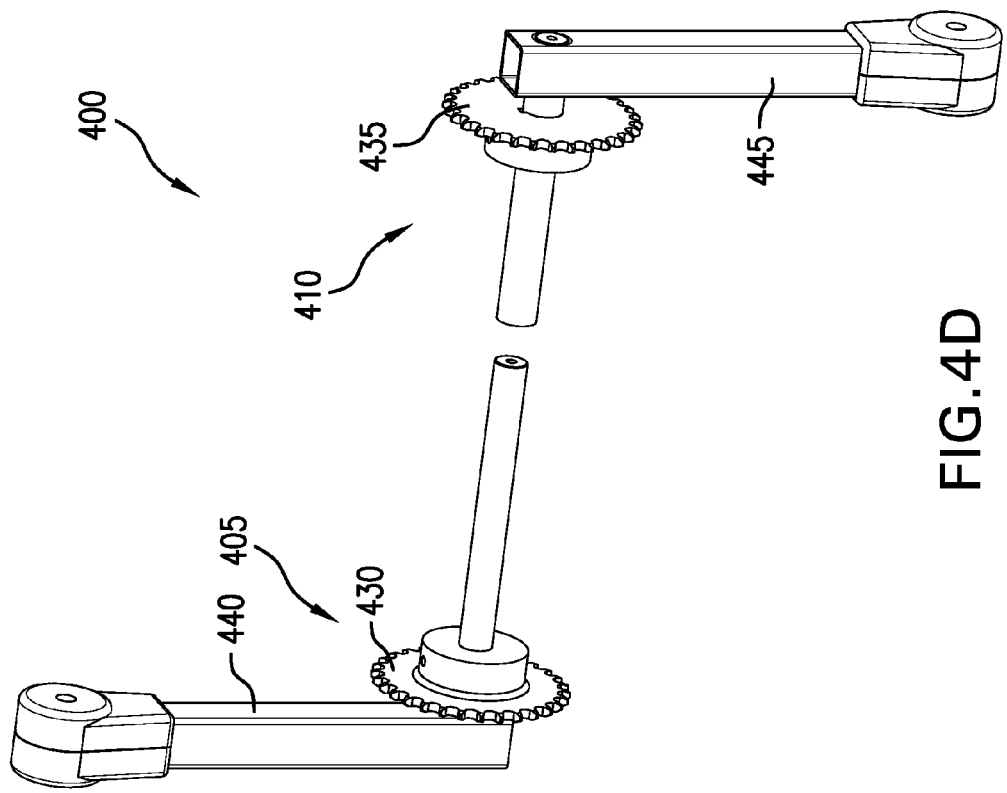
Figure 4D:
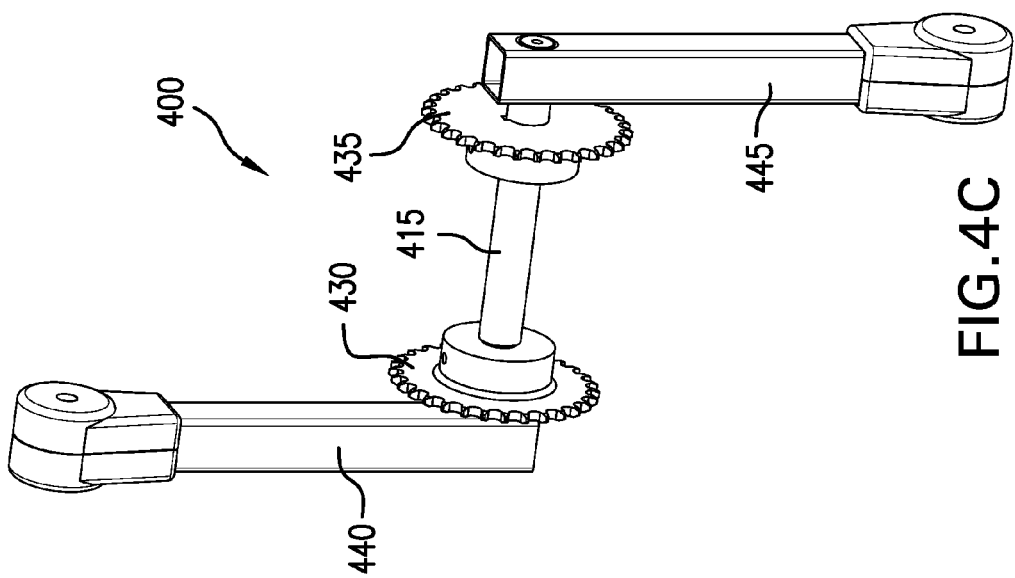

FIGS. 4A-4D depict an exemplary leg crank for a natural-gait therapy device. In the FIGS. 4A-4B depiction, an exemplary leg crank 400 is depicted in a side-by-side/standing mode. In the FIGS. 4C-4D depictions, and exemplary leg crank 400 is depicted in an opposition/natural-gait mode. The leg crank 400 is actually two independent leg cranks, a right leg crank 405 and a left leg crank 410. When in the transfer mode, and when in a standing position, the right and left leg cranks 405, 410 are aligned as depicted in the transfer/standing mode figures (FIGS. 4A-4B). In FIG. 4A, the right and left leg cranks 405, 410 appear to share a single axel 415, but in FIG. 4B, the exploded view reveals that in this embodiment the left leg crank 410 has a left axel 420 having and open center with an inner diameter. The figure depicts the right leg crank 405 having a right axel 425 with an outer diameter. In the depicted embodiment, the outer diameter of the right axel 425 is smaller than the inner diameter of the left axel 420. Independent right and left axels 420, 425 may permit the crank positions to be transitioned from the side-by-side/standing mode to the opposition/natural-gait mode. In the depicted embodiment, the rotational orientation of each of the leg cranks 405, 410 is determined by a right and a left chain each corresponding to a right and a left chain gear 430, 435. Each of the right and the left chain gears 430, 435 is rigidly coupled to the corresponding right or left axel 425, 420. Each of the right or left axels 425, 420 is rigidly coupled to a right or left drive arm 440, 445.

The independent control of the leg cranks 405, 410 may advantageously permit the transition from a side-by-side/standing position of the foot rests 215 to an opposition/natural-gait position of the foot rests 215. When a body is performing a natural-gait motion, each of the user's feet may be in opposition and may travel in an elliptical path. Over a cycle of a natural-gait, the two feet may be in opposition and/or may have a 180 degree phase differential. Thus, during a natural-gait cycle, the two feet may not be side-by-side as they typically are in the standing position. Even when the two feet have approximately the same position as measured in the forward/backward direction, one of the two feet may have a higher elevation than the other. Transitioning from the side-by-side/standing position to the opposition/natural-gait position may be done before the natural-gait cycling of the legs may begin.

To accomplish this transition from the side-by-side/standing position to the opposition/natural-gait position, only one of the leg cranks 405, 410 may be rotated, and the other leg crank 410, 405 may remain in a fixed position. The rotated leg crank 405, 410 may be rotated half a cycle, until the rotated leg crank 405, 410 is approximately 180 degrees out of phase with the fixed leg crank 410, 405. Then the right and left leg cranks 405, 410 may be coupled together in the above described 180 degree phase differential or opposition. When the two leg cranks 405, 410 are coupled in opposition, the leg cranks 405, 410 may rotate together with the same frequency, but always remaining 180 degrees out of phase with respect to each other.

Figure 5A:
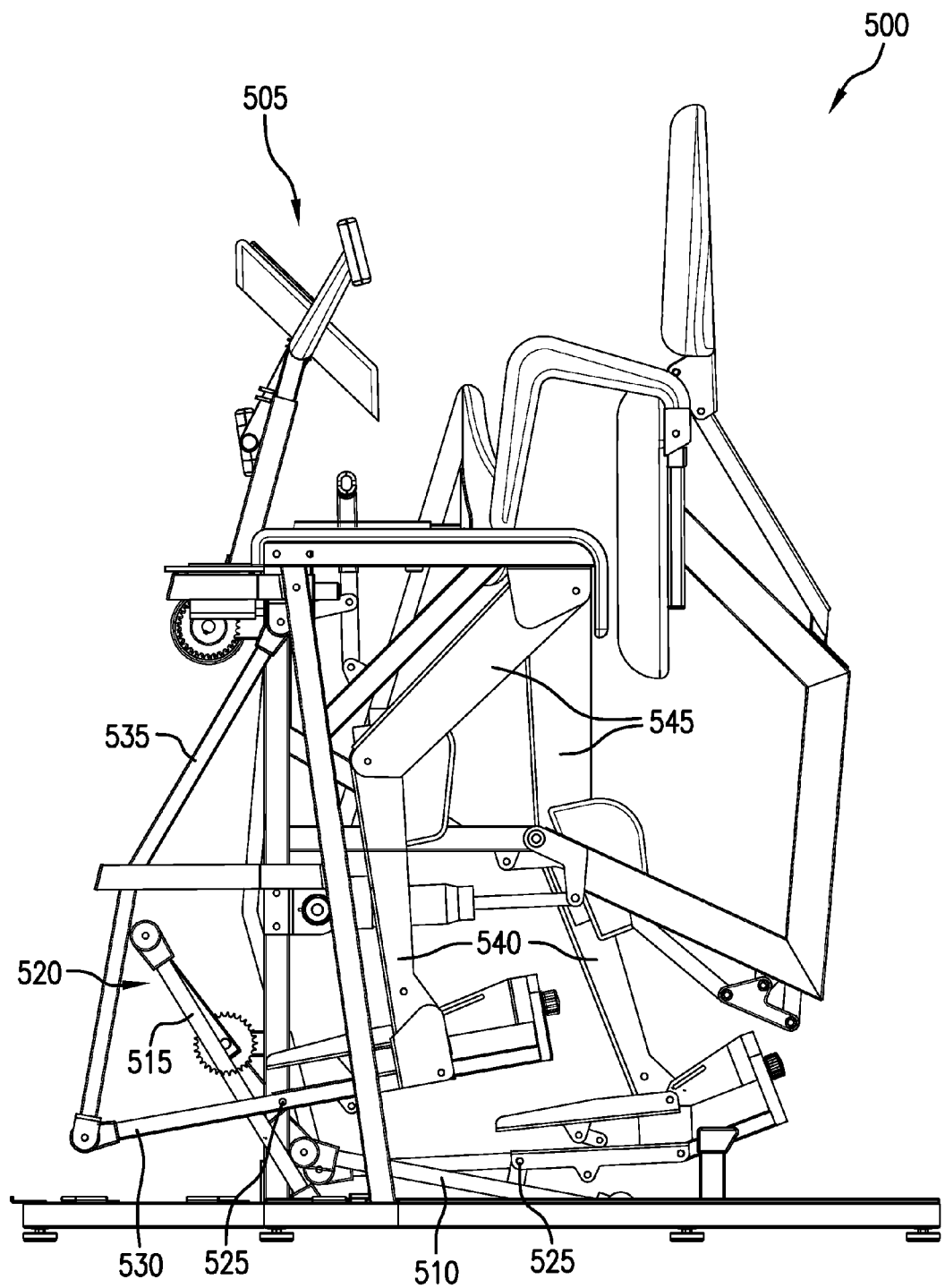
FIGS. 5A-5H depict an exemplary natural-gait therapy device depicting a sequence of phases of the natural-gait locomotion.
Figure 5B:
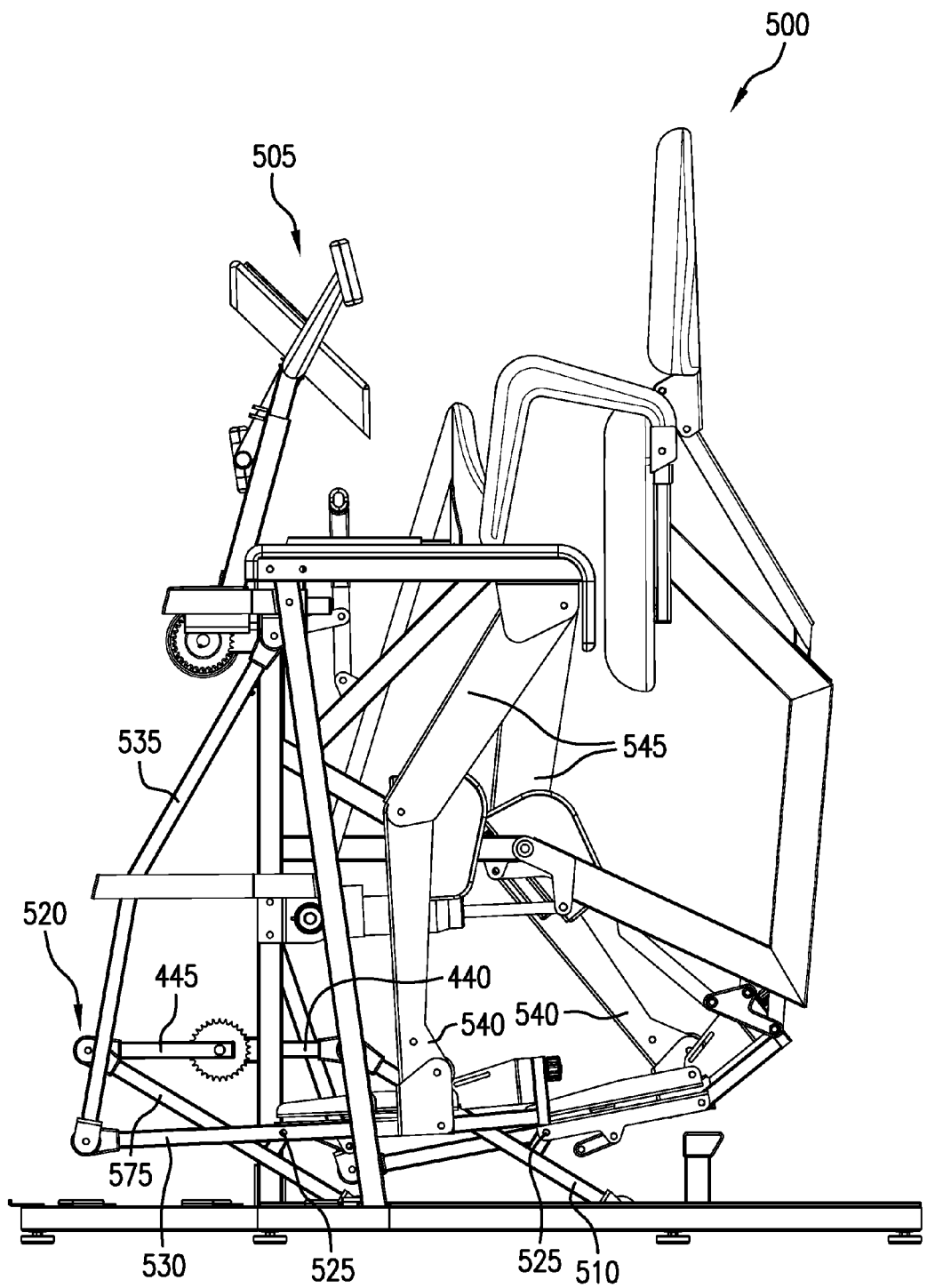
Figure 5C:
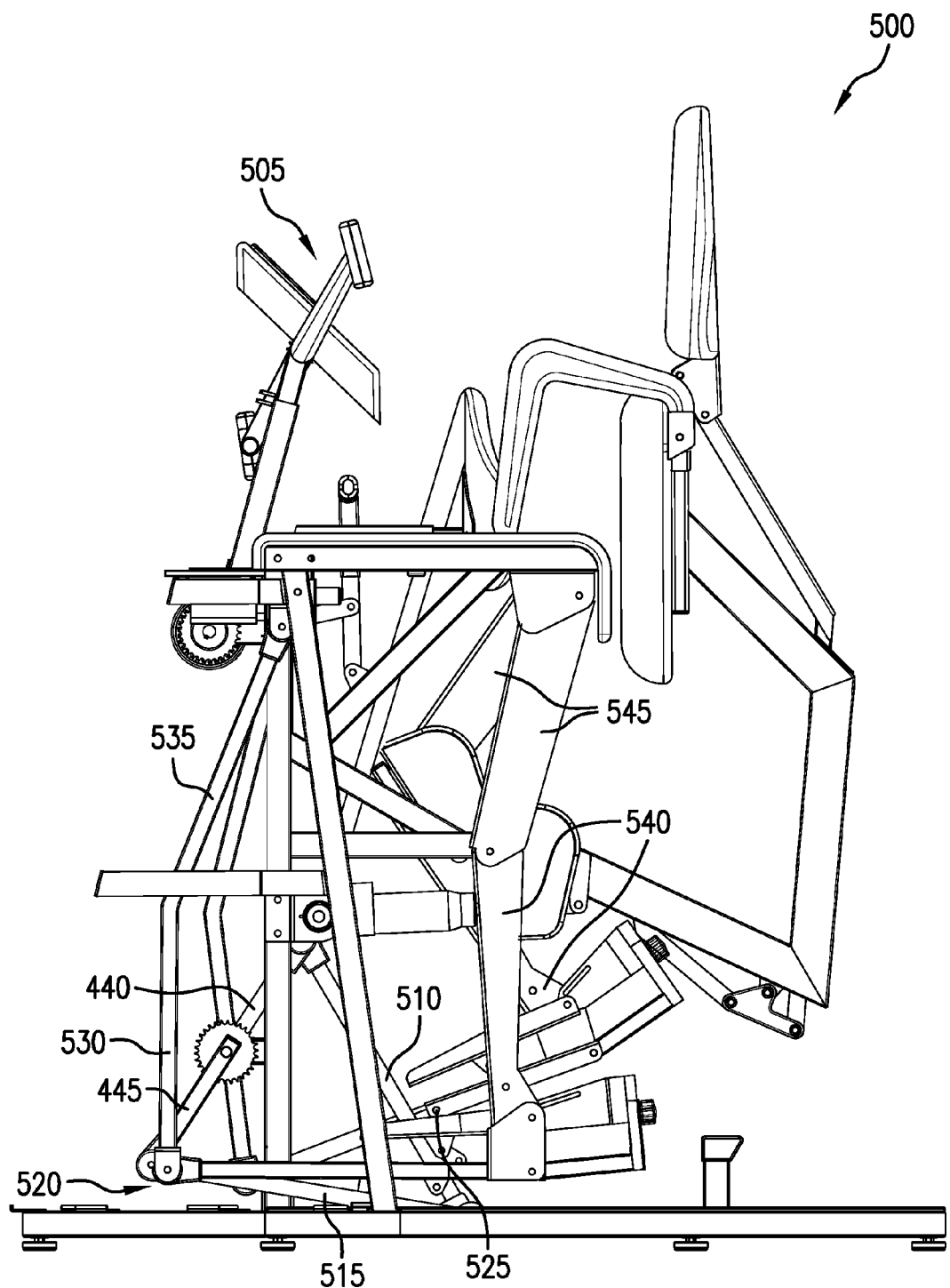
Figure 5D:
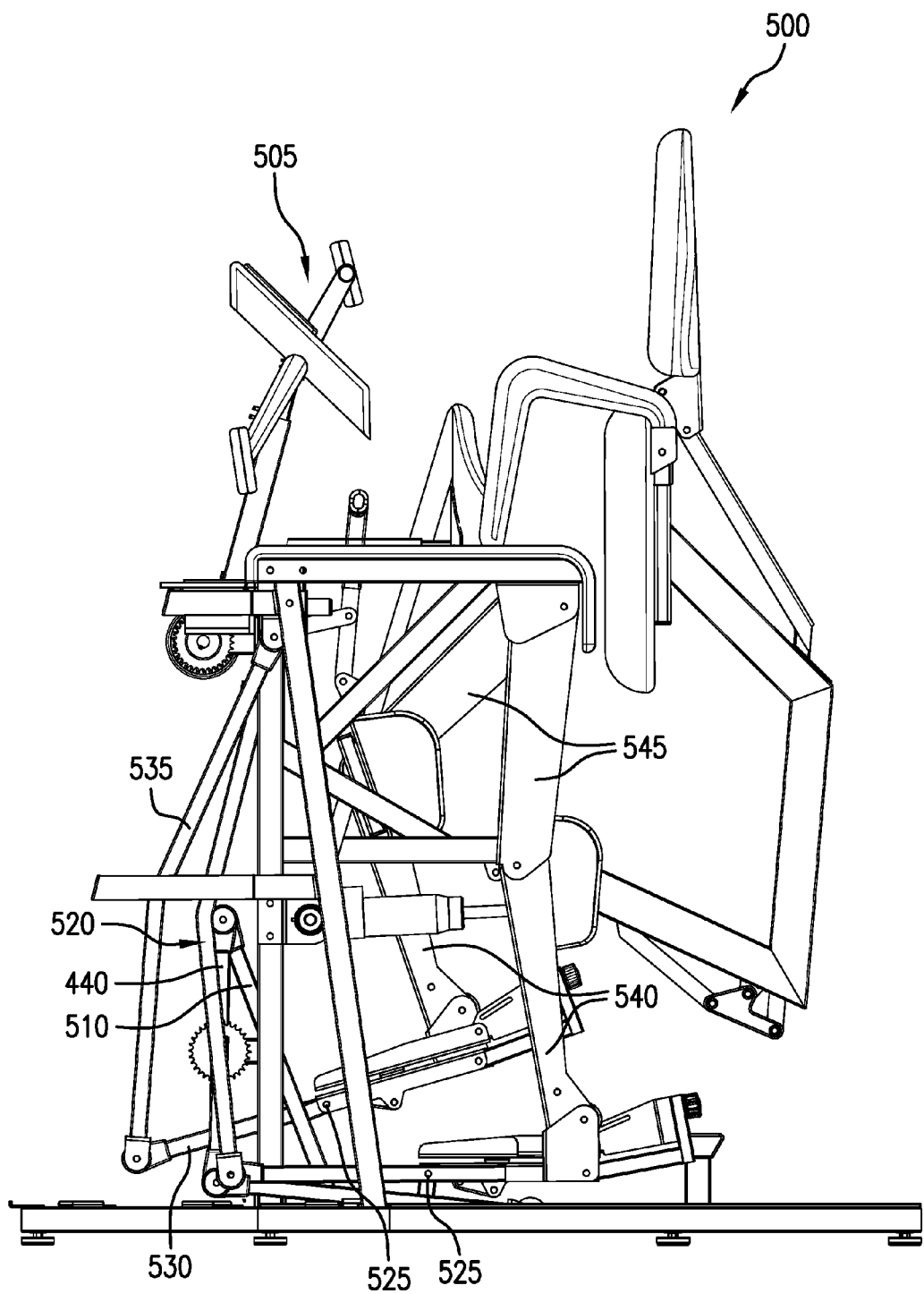
Figure 5E:
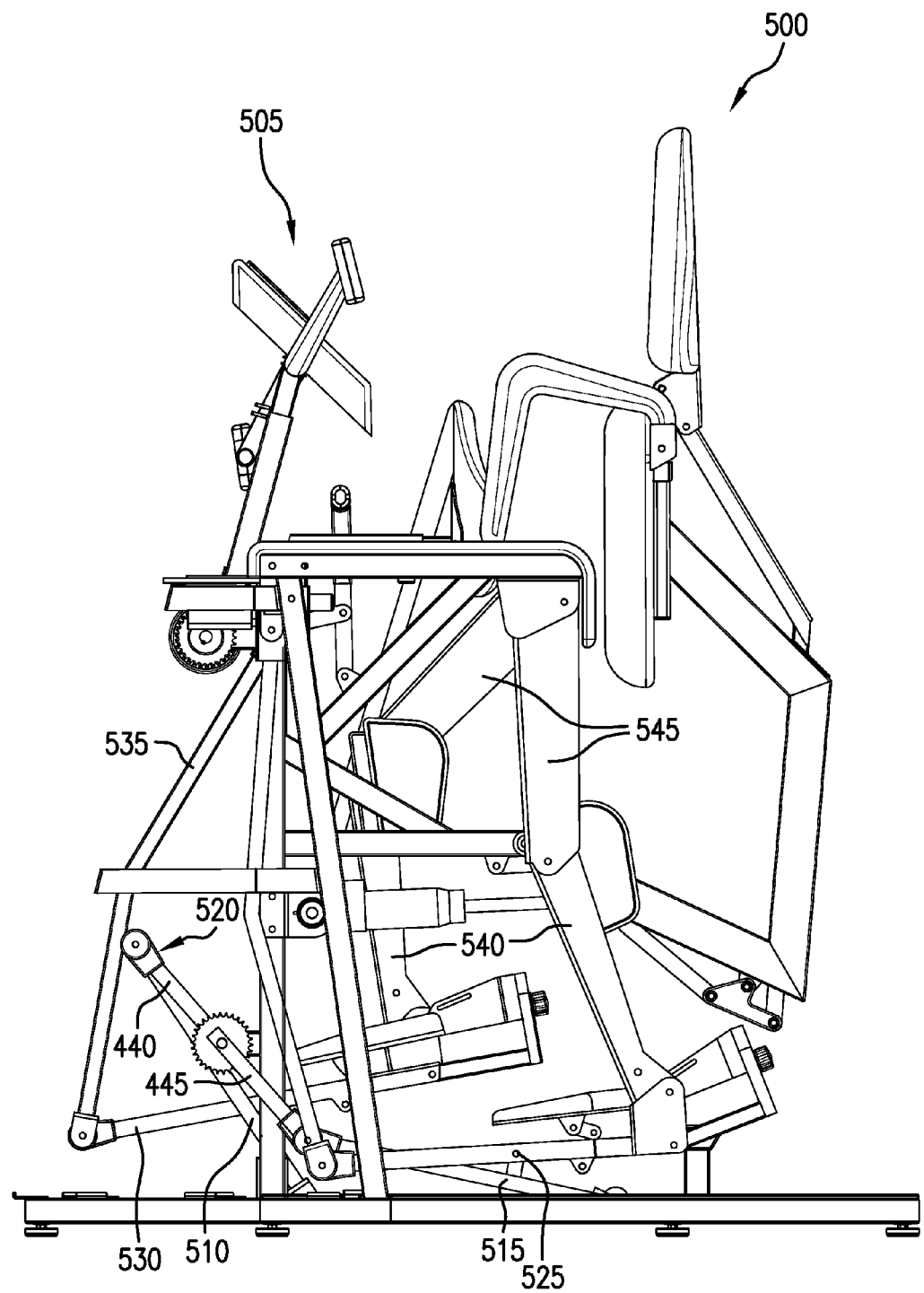
Figure 5F:
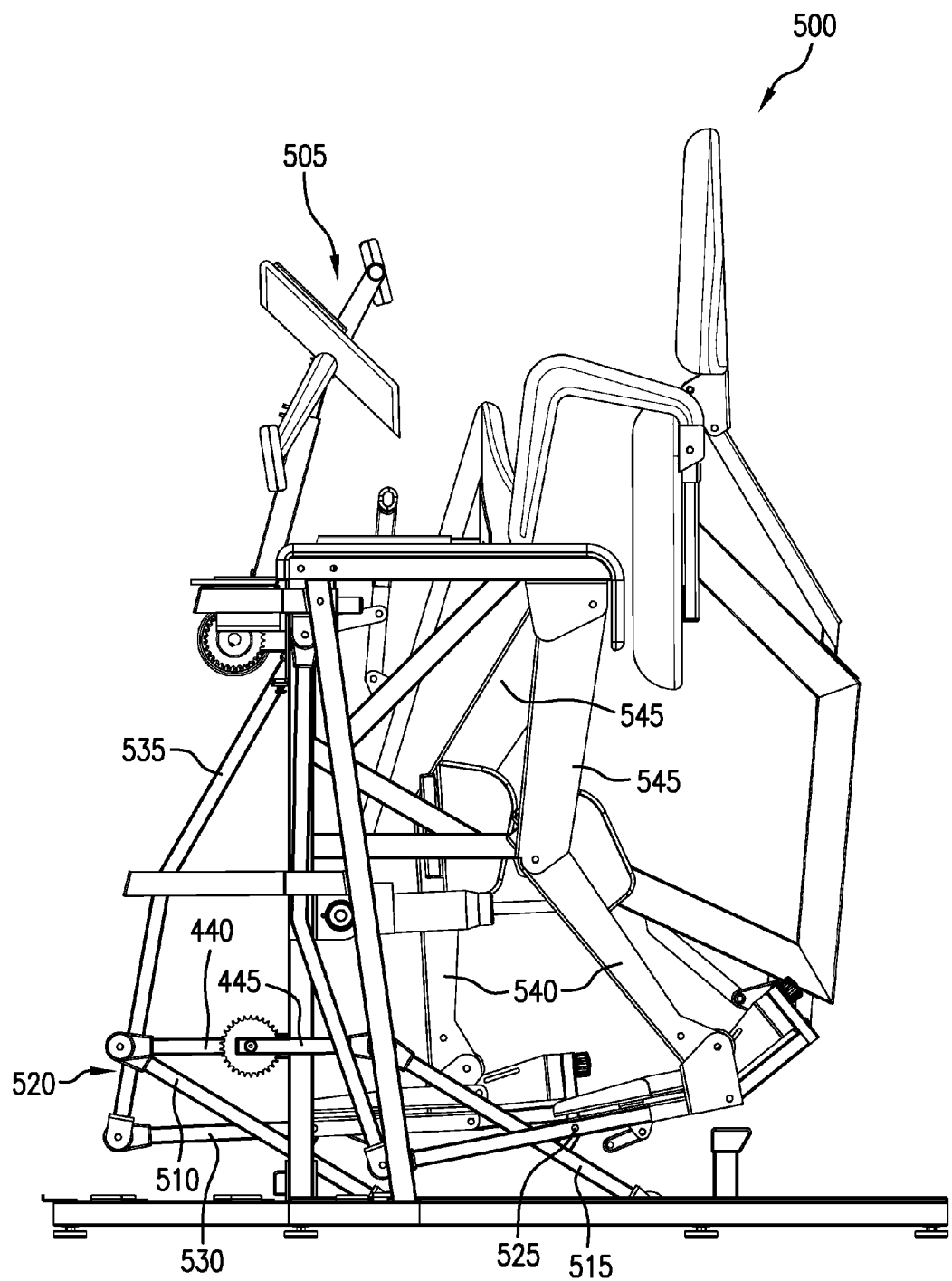
Figure 5G:
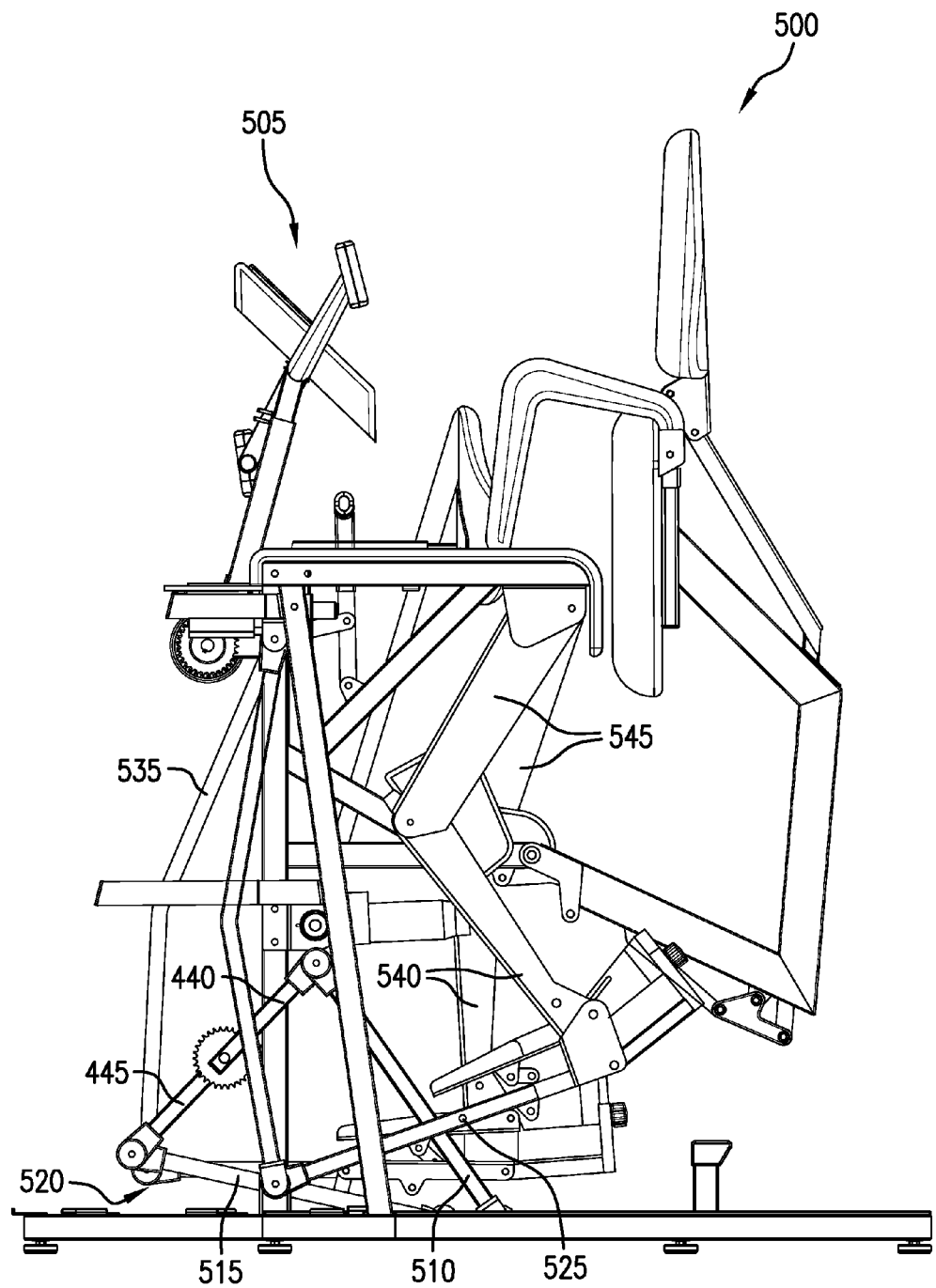
Figure 5H:
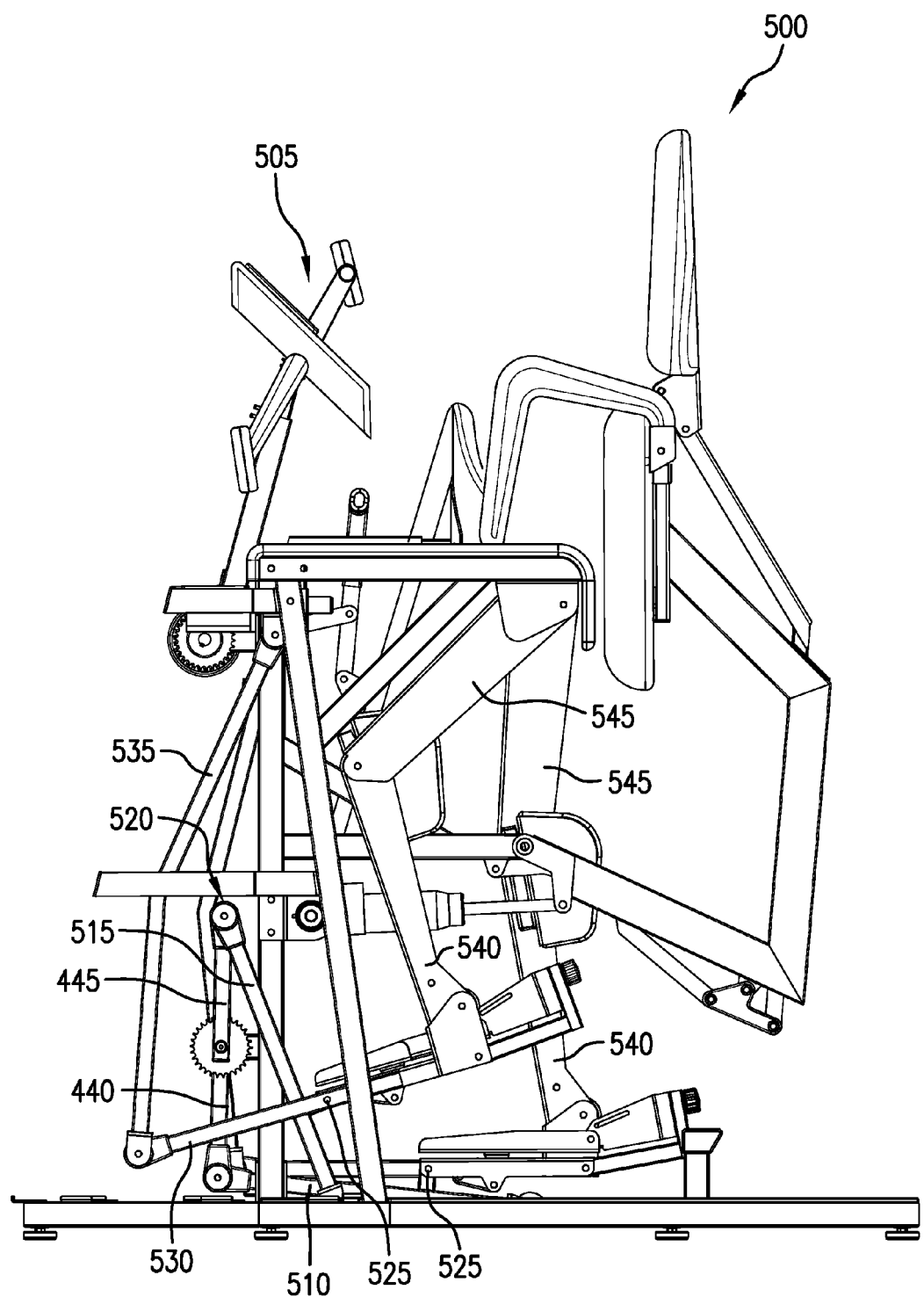

FIGS. 5A-5H depict an exemplary natural-gait therapy device depicting a sequence of phases of the natural-gait locomotion. Each of the FIGS. 5A-5H show an exemplary natural-gait therapy device 500, each with feet positions at different phases in a natural-gait cycle. For example, if the feet position of the FIG. 5A depiction is called the zero degree position, then FIGS. 5B-5H correspond to the 45, 90, 135, 180, 225, 270, and 315 degree positions, respectively. Locomotion of a natural-gait may be induced by a locomotion module. In the depicted embodiment a hand powertrain 505 provide locomotive power to the natural-gait therapy device. In the depictions, a hand powertrain 505 does not reflect the phase orientations that should be associated with the various phase positions of the foot rests.

Figure 6:
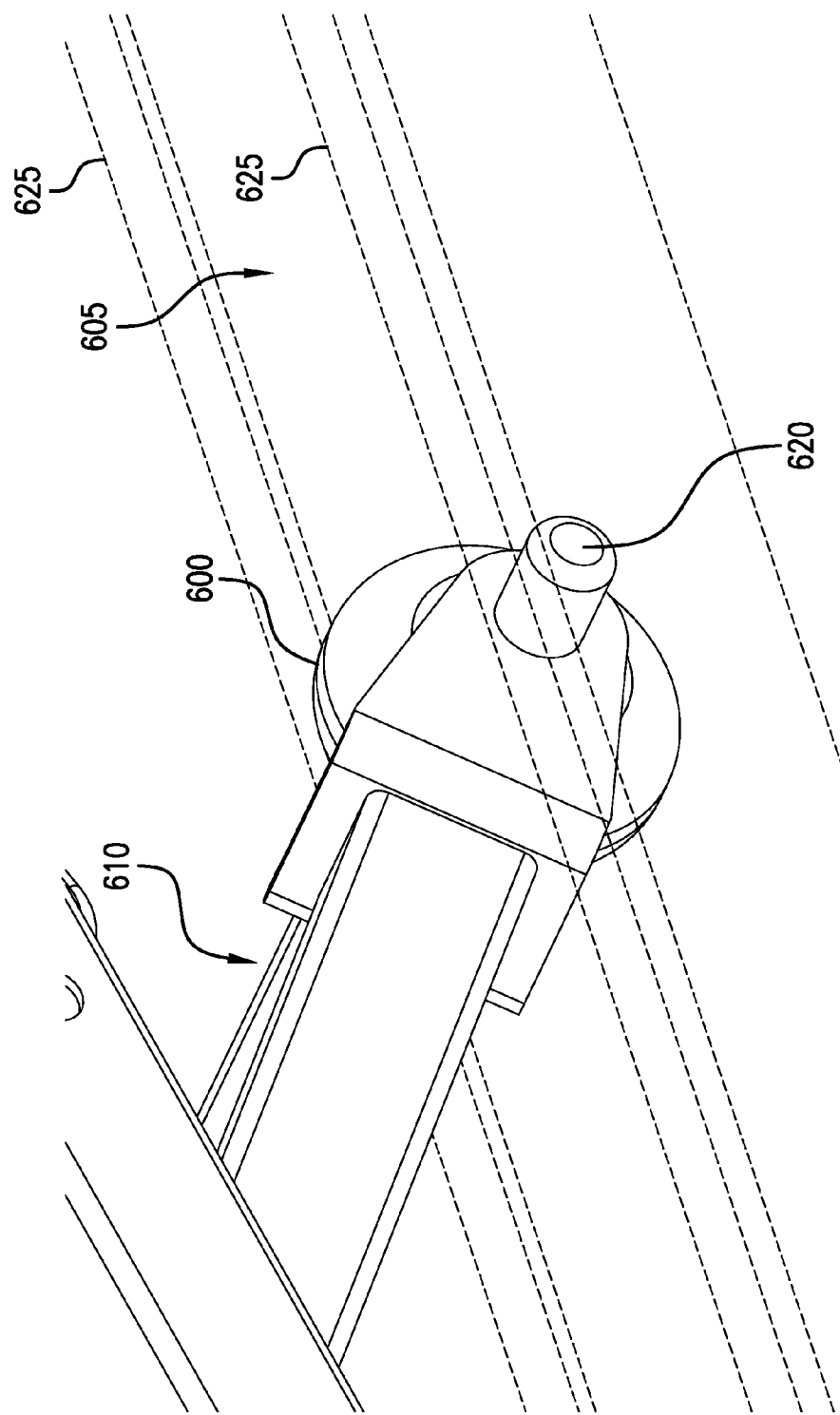
FIG. 6 depicts a close-up view of an exemplary wheel of an exemplary rolling foot-drive member.

When the natural-gait therapy device 500 is operating in a natural-gait mode, each of the left and right drive arms 445, 440 may be pivotably coupled to a left and right rolling foot-drive member 510, 515, respectively. FIG. 6 depicts a close-up view of an exemplary wheel of an exemplary rolling foot-drive member 510, 515. Each of the depicted rolling foot-drive members 510, 515 has a wheel 600 that rides in a drive track 605. The wheel 600 may be attached to a distal end 610 of the rolling foot-drive member 510, 515. In the depicted embodiment, a protruding axel guide 620 may extend from either side of an axel of the wheel 600. This protruding axel guide 620 may be captured by one or more flanges 625 of the drive track 605. The flanges 625 of the drive track 605 may retain the rolling foot-drive member 510, 515 within the drive track 605. The retention of the rolling foot-drive member 510, 515 within the drive track 605 may prevent the rolling foot-drive member 510, 515 from being accidentally removed from the drive track 605. Various users may present various forces upon the contact points with an exemplary natural-gait therapy device. Different types of user's bodies and different user's abilities may provide for a broad distribution of force profiles. For example, when transitioning from a sitting position to a standing position, some users may exert a force on the knee pads that may otherwise result in the rolling foot-drive member 510, 515 to rise up and out of the drive track 605.

A proximal end 520 of the rolling foot-drive member 510, 515 may be pivotably coupled to the left or right drive arm. The proximal end may travel in a circular orbit determined by the rotating drive arm 440, 445 to which the rolling foot-drive member 510, 515 may be pivotably coupled. The distal end 610 may travel in a back-and-forth linear motion along the drive track 605. A foot-drive connecting point 525 somewhere between the distal end 610 and the proximal end may pivotably couple the rolling foot-drive member 510, 515 to the foot motion platform 225. The motion of this foot-drive connecting point 525 is determined by the interpolated motion of the back-and-forth linear motion and the circular motion of the extreme ends (distal and proximal ends). This motion may be called elliptical motion and has a forward and backward component as well as an up and down component.

Not only will the foot motion platform be moved in an elliptical fashion at the foot-drive connecting point 525, but a rotation of the angle of the foot rest 215 with respect to the ground may also be achieved. In the depicted embodiment, the rotation of the foot rest 215 may have a cyclic behavior having the same cycle frequency as the elliptical motion. This may result from a linkage creating the foot rotation, the linkage being driven by the elliptical movement. In the depicted embodiment, a foot extension member 530 extends from the foot motion platform 225 forward and past the pivotable connection point of the foot motion platform 225 and the rolling foot-drive member 510, 515. At the distal end of foot extension member 530 as measured from the foot motion platform 225, the foot extension member 530 pivotably couples to a pendulum support member 535. The other end of the pendulum support member 535 is attached to the cage 255 at a pivot location. The amount of foot rotation may be determined by a ratio of the lengths of the foot extension member 530, from the pivot location of the foot motion platform 225 to the pivot location at the pendulum support member 535, to the length of the pendulum support member between its two pivot points. In some embodiments, one or both of these members may be adjustable so as to control the amount of foot rotation.

The knee movement is coupled to the cyclic motion of the foot motion platforms 225. In the depicted embodiment, a lower leg member 540 is pivotably coupled to the foot motion platform 225 at a foot connecting end of the lower leg member 540. The lower leg member 540 is pivotably coupled to an upper leg member 545 at a knee end of both the lower and upper leg members 540, 545, respectively. The upper leg member 545 is pivotably coupled to the cage 255 at a hip connecting end of the upper leg member 545. The lower and upper leg members 540, 545 move in response to the foot motion platforms 225 which are driven by the rolling foot-drive members 510, 515. The pivot locations connecting the knee ends of the upper leg members 545 to the knee ends of the lower leg members 540 may facilitate a natural-gait leg motion during natural-gait operation.

FIG. 7 depicts a close-up view of an exemplary knee engagement member. In the FIG. 7 embodiment, a knee engagement member 700 may couple to the knee end of the lower leg member 540. A knee pad 230 may be slidably coupled to the knee securing member 550 providing a vertical slide path for the knee pad 230. A slidable knee coupling member 705 may protect against chafing of the knee during the cyclic movement of the natural-gait movement. For persons whose leg dimensions mismatch the corresponding dimensions of the natural-gait therapy device 500, the slidable knee coupling member 705 may minimize sheer forces to the user's knee against the knee pad 230. In some embodiments, the natural-gait motion of a user's legs may exercise the slidable knee coupling member 705 to prevent chafing the user's knees.

In some embodiments, the knee engagement member 700 and the knee pad 230 are configured to locate a pivot joint of the user's knees to be in line with the pivot joint of the pivotable connection between the lower leg member 540 and the upper leg member 545. In some embodiments a knee engagement surface of the knee pad 230 is forward of the line connecting the pivot joints of the pivotable connection between the lower leg members 540 and the upper leg members 545. Forward configurations may account for the pivoting axis of a user's knee to be rearward of the knee engagement surface of the knee pad, providing better alignment between the pivot joint of the natural-gait therapy device 500 and the user's knee joint. In some embodiments, the forward location of the knee pad 230 may be adjustable to accommodate the anatomy of different users. For example, different sized shims may be insertable between the knee pad 230 and the knee engagement member 700. In the depicted embodiment, the knee pad 230 is positioned slightly forward of knee pivot joints of the natural therapy device so that the user's knee pivots in-line with these pivot point.

Figure 8B:
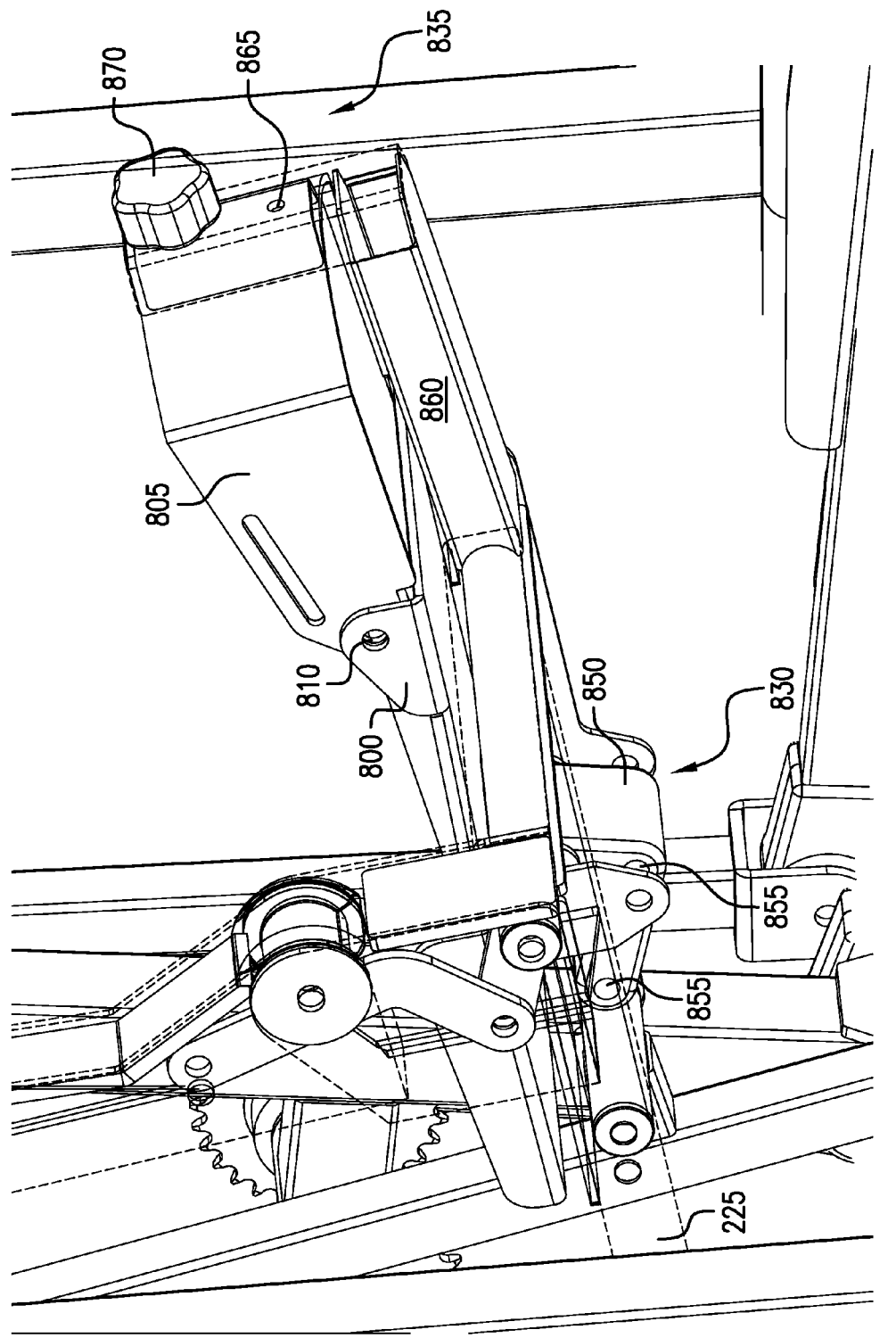

In some embodiments, a heel lift will be cyclically performed in response to the elliptical motion of the foot rests. FIGS. 8A-8B depict a close-up view of a heel lift system. The foot rest in the depicted embodiment provides for adjustable foot height and for heel lift coordination. The footrest height adjustment may be performed as in the depicted embodiment. Two height adjustment controls, a forefoot height adjustment control and a heel adjustment control are depicted. The forefoot height may be adjusted by selecting a coupling distance between a forefoot rest 800 and the foot motion platform 225. The forefoot rest 800 may be adjustably coupled to the foot motion platform 225 by coupling the foot motion platform 225 to one of a plurality of height adjustment apertures 850 of a coupling member 855. In the depicted embodiment, two height adjustment apertures 850 are visible. In some embodiments three or more height adjustment apertures may be used. The heel height may be adjusted by selecting a coupling distance between a heel rest 805 and a heel pivot lever 860. The heel rest 805 may be adjustably coupled to the heel pivot lever 860 by coupling the heel rest 805 by selecting one of a plurality of height adjustment apertures 865. In the depicted embodiment, a spring loaded selection pin 870 may engage one of the plurality of height adjustment apertures 865, for example.

The heel pivot coordination may be performed as in the depicted embodiment. In the figures, a foot rest 215 includes the forefoot rest 800 and the heel rest 805. The forefoot rest 800 and the heel rest 805 are shown pivotably coupled at a heel pivot 810. The heel pivot control includes a heel rotation pivot axel 815 and a pivot control arm 820. The pivot control arm 820 is rigidly coupled to the pivot axel 815. In the figure, the pivot control arm 820 is depicted extending from the pivot axel 815 at a ten o'clock orientation. If the pivot control arm 820 is rotated to a nine o'clock orientation, the heel rest 805 will rotate in a clockwise direction promoting heel lift. If, however, the pivot control arm 820 is rotated to an eleven o'clock orientation, the heel rest 805 will rotate in a counterclockwise direction producing a heel fall. The pivot control arm 820 is actuated by a pivot control lever 825 pivotably attached to a heel end of the lower leg member 540. As the distance between the pivot point of the pivot control lever 825 at the heel end of the lower leg member 540 and the pivot axel 815 is reduced, the control arm 820 will move in a counter clockwise direction. And as the distance between the pivot point of the pivot control lever 825 at the heel end of the lower leg member 540 and the pivot axel 815 is increased, the control arm 820 will move in a clockwise direction. Because a pivot connection 830 between the lower leg member 540 and the foot rest 215 is aft and lower than the line connecting the pivot point of the pivot control lever 825 at the heel end of the lower leg member 540 and the pivot axel 815, the distance between the pivot point of the pivot control lever 825 at the heel end of the lower leg member 540 and the pivot axel 815 will reduce when the angle between the lower leg member 540 and the foot rest 215 is reduced. Conversely, the distance between the pivot point of the pivot control lever 825 at the heel end of the lower leg member 540 and the pivot axel 815 will increase when the angle between the lower leg member 540 and the foot rest 215 increases. In summary, as the lower leg member 540 is angled forward toward the foot rest 215, the heel rest will lift, and as the lower leg member 540 straightens increasing the angle between the lower leg member 540 and the foot rest 215, the heel rest will fall.

Figure 9A:
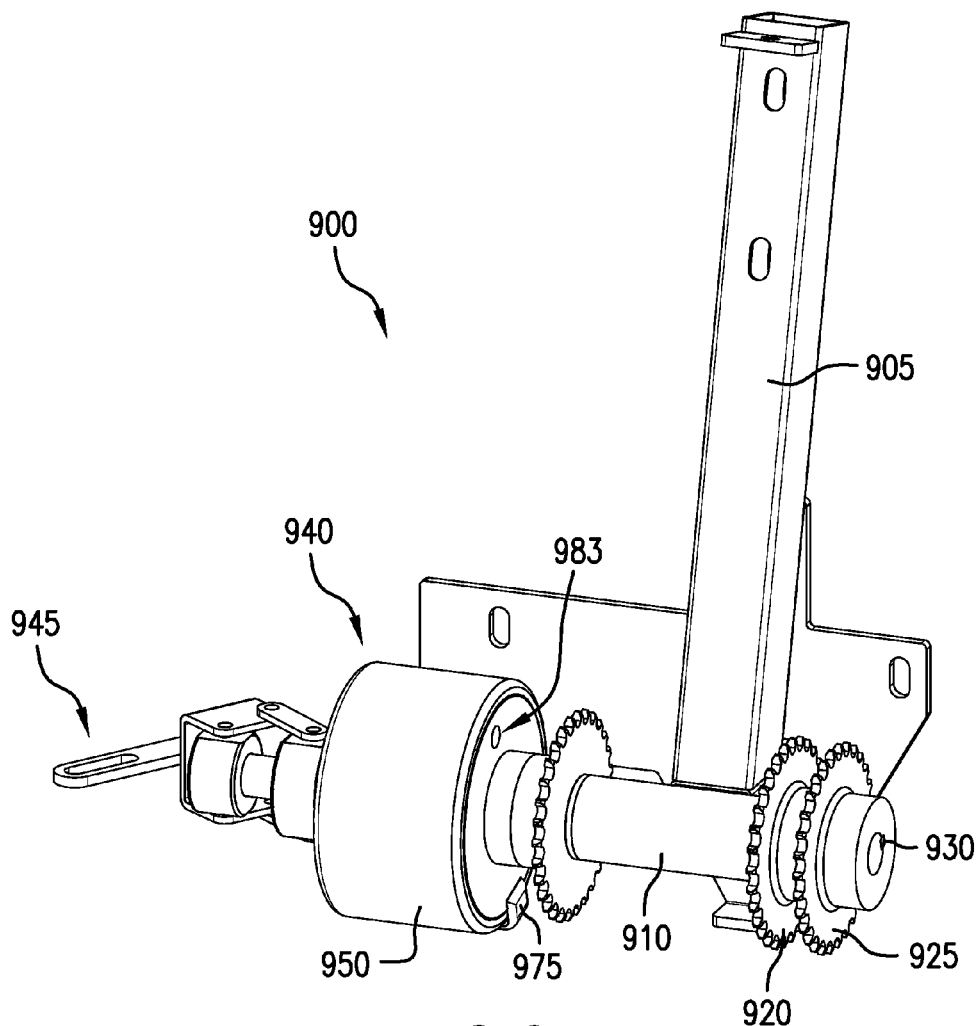
FIGS. 9A-9B depict an exemplary transmission module for an exemplary natural-gait therapy device.
Figure 9B:
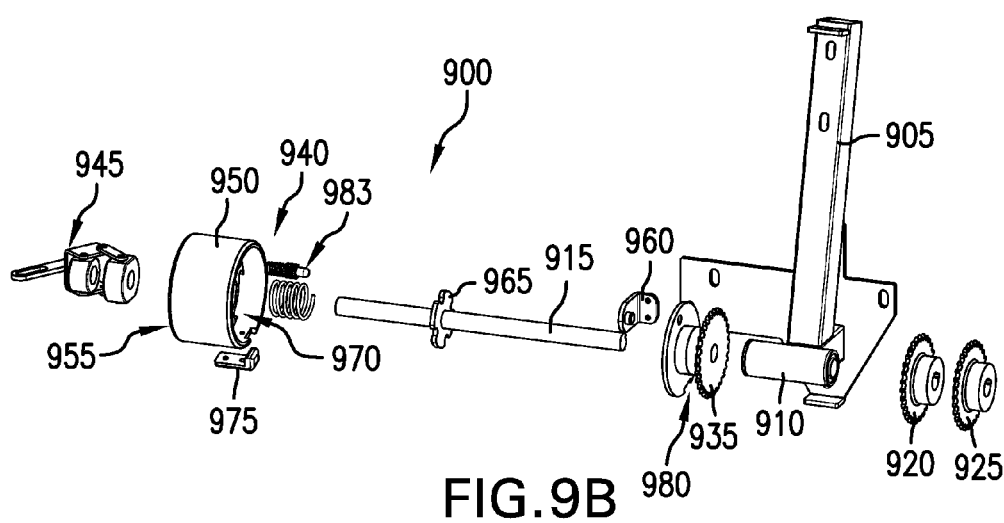

FIGS. 9A-9B depict an exemplary transmission module for an exemplary natural-gait therapy device. The functions of this exemplary transmission module may include one or more of the following: i) unlock the foot rests from the transfer/standing positions; ii) enable one of the leg cranks to rotate from a side-by-side/standing location to an opposition/natural-gait position; iii) when opposition is reached, automatically engage the second leg crank and fix its relative location to be 180 degrees out of phase with the first leg crank; iv) disengage the coupling of the two leg cranks into an opposition alignment, while simultaneously enabling both left and right side locks which locks each leg cranks when it is positioned in the transfer/standing position.

In FIG. 9B, the transmission module is depicted in an exploded view. The depicted transmission module 900 is rotatably couple to a vertical support member 905 via and axel bearing 910. In some embodiments an axel bushing may be used to rotatably couple the transmission module 900. A drive axel 915 is supported by the axel bearing 905 and coupled to a left-leg drive gear 920 and a power drive gear 925. The power drive gear 925 may be chain coupled to a hand drivetrain 505. The hand drivetrain 505 may provide locomotion to a natural-gait therapy device 500. In some embodiments, locomotion may be provided by alternative means. For example, in some embodiment, an electric motor may provide locomotive power to the power drive gear 925. In an exemplary embodiment, the drive axel 910 may be driven by a locomotive force. The power drive gear 925 and the left-leg drive gear 920 are depicted as coupled to the drive axel 915 using a key 930. The key 930 may rotationally couple the power drive gear 925 and the left-leg drive gear 920 to the drive axel 915. In this way, when the power drive gear 925 is rotated, the drive axel 915 may be rotated and the left-leg drive gear 920 may be rotated.

The depicted transmission module 900 includes a right-leg drive gear 935. The right-leg drive gear 935 may not be rigidly coupled to the drive axel 915 as is the left-leg drive gear 920. The right-leg drive gear 935 may be selectively coupled to the drive axel 915 when in an opposition alignment position with respect to the left-leg drive gear 920. An opposition coupling mechanism 940 may couple the right-leg drive gear 935 to the drive axel 915 when the drive axel 915 is rotated to an opposition alignment position with respect to the left-leg drive gear 920. Such an opposition alignment position may be attained when the transmission module 900 is in an engaged mode. The engaged mode may facilitate a user's natural-gait motion, such as, for example, a walking gait wherein the user's feet may be oppositionally aligned.

The transmission module 900 may have an engaged mode and a locked mode. When in the locked mode, both the right-leg drive gear 935 and the left-leg drive gear 920 may be effectively locked into a transfer/standing position, in which a user's feet may be in a side-by-side position. A transmission engagement lever 945 may perform the engagement/locking operation of the transmission. When the transmission engagement 945 lever is pulled, the transmission 900 may be engaged. This engagement may force a coupling hub 950 to slide along the drive axel 915 away from the engagement lever 945. When the coupling hub 950 slides away from the engagement lever 945, a coupling hub locking aperture 955 (in a back-side of the coupling hub in this depiction) may disengage a hub locking member 960. In the FIG. 9A depiction, the hub locking aperture 955 in the coupling hub 950 has the hub locking member 960 inserted therein. But when the coupling hub 950 is slid away from the engagement lever 945, the coupling hub 950 clears the hub locking member 960. The coupling hub 950 is slidably coupled to the drive axel 915 via a star gear 965. Within the coupling hub 950 is a star gear aperture 970, within which the star gear 965 slidably engages the coupling hub 950. The coupling hub 950 and drive axel 910 are rotationally coupled via the star gear 965 and complementary star gear aperture 970. Thus, regardless of the mode, engaged or locked, the coupling hub 950 may be rotationally locked to the drive axel 915. Thus, when the coupling hub 950 is locked, the drive axel 915 is locked, the left-leg drive gear 920 is locked and the power drive gear 925 is locked.

When the coupling hub 950 is engaged (slid along the axel), not only is the hub locking member 960 disengaged from the locking aperture 955 in the coupling hub 950, but the right-leg drive gear 935 is unlocked from the coupling hub 950. A right gear locking member 975 disengages from a complementary locking aperture 980 in the right-leg drive gear 935. When both locking members 960, 974 are disengaged, both the left-leg drive gear 920 and the right-leg drive gear 935 are free to rotate. The transfer/standing position of the foot rests 215 may be at the lowest elevation of the elliptical cycle. The weight of the user may keep the foot rests 215 in the transfer/standing position even when unlocked by the transmission module 900.

When the coupling hub 950 is locked, both locking members 960 975 may be locked. The locking member 960 may lock the coupling hub 950 so that the coupling hub 950 cannot rotate. As the coupling hub 950 may be rotationally coupled to the axel 915 and in turn, the left-leg drive gear 920, the locking member 960 may lock the left leg into a locked transfer standing position. The locking member 975 may lock the coupling hub 950 to the right-leg drive gear 935. As the coupling hub 950 is rotationally coupled to the left-leg drive gear 920, the locking member 975 may lock the left-leg drive gear to the right-leg drive gear. The locking alignment of the locking member 975 may be such that the left-leg is aligned in a side-by-side alignment with the right-leg when in the locking member 975 is engaged. When both locking members 960, 975 are engaged, both of the user's legs may be locked into a side-by-side transfer/standing position. This locked transfer/standing position may lock the foot rests in a transfer position, which may be that position that the feet are in a specific anatomic position with respect to the knees of the user, so as to be able to transition between a sitting position and a standing position without compromising anatomic motion. The locking of the feet position may substantially inhibit feet motion both in the longitudinal direction and differential motion of both feet. The locked transfer position may be the lowest elevation positions of both of the foot motion platforms 505 over their periods of elliptical orbits. At the lowest elevation positions, gravity may assist the user in returning to the transfer position when the locking members 960, 975 are both disengaged.

When the transmission module 900 is in the engaged mode, and both the left-leg and right-leg drive gears 920, 935 are unlocked, the hand drivetrain may now provide drive power to the main power gear 925. When the main power gear 925 is rotated, the left-leg drive gear 920 is simultaneously rotated. The left-leg drive gear 920 then may be chain coupled to the left-leg crank gear 435, which in turn moves the left leg. The right-leg drive gear 935 may remain uncoupled from the drive axel 915 until the coupling hub 950 is rotated into the opposition coupling position. When the user's left leg is rotated to a position in which the left leg is 180 degrees out of phase as the right leg, a spring loaded opposition coupling member 983 couples the coupling hub 950 to the right-leg drive gear 935. Further rotation of the power drive gear 925 now will rotate both the left-leg and right-leg drive gears 920, 935. This in turn may rotate both the left and right foot rests 215 proving power for their elliptical orbits. In some embodiments, a one-to-one ratio of gear teeth between the leg drive gears 920, 935 and the left and right chain gears 430, 435 may ensure that each turn of a leg drive gear 920, 935 produces a single turn of each of the chain gears 420, 435. This one-to-one ratio between the leg drive gears 920, 935 and the chain gears 420, 435 may permit the transmission to reliably lock the foot rests into both the foot-opposition position and the side-by-side position.

Various gear ratios may be used to make the locomotion operation easier or more difficult. In some embodiments, each hand powertrain 505 rotation may produce a single rotation to the power drive gear 925. In some embodiments, to make it easier to hand-locomote the natural-gait operation, two rotations of the hand powertrain 505 may produce a single rotation of the power drive gear 925. Various turns ratios may be used to provide users with varying degrees of hand strength proper levels of effort for good natural-gait therapy. In an exemplary embodiment, a selectable gear transmission module may provide user electability as to the gear ratio for use. In an exemplary embodiment, a bicycle type of derailleur may be used to facilitate gear ratio changes.

Figure 10:
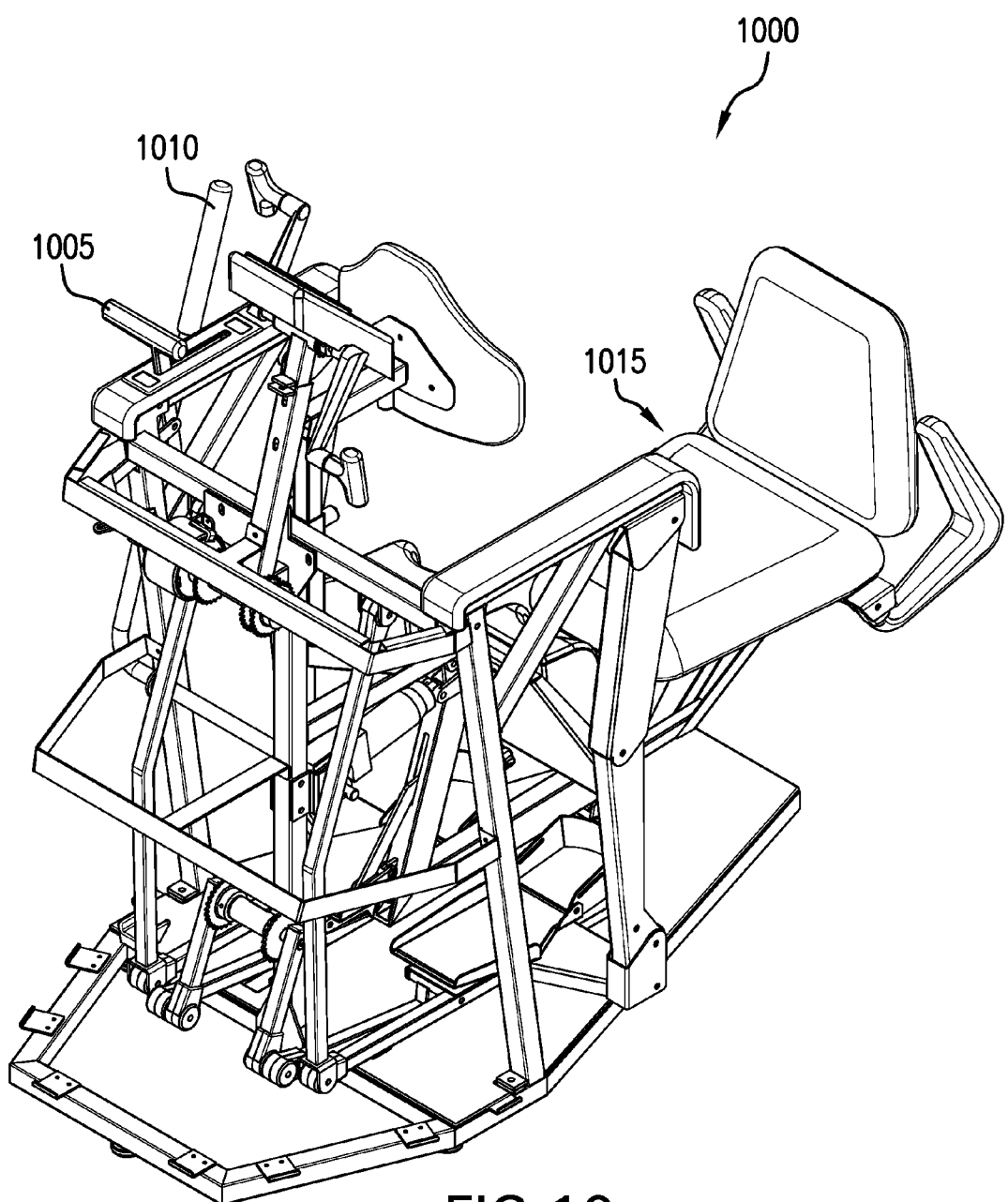
FIG. 10 depicts a perspective view of an exemplary natural-gait therapy device.

FIG. 10 depicts a perspective view of an exemplary natural-gait therapy device. In the FIG. 10 embodiment, an exemplary natural-gait therapy device 1000 includes a locked/engagement lever 1005. The locked/engagement lever may couple to the transmission engagement lever. When in a forward position, the locked/engagement lever may control the transmission to be in the locked position, in which the user may be in a standing position with side-by-side feet. When in the rearward position, the locked/engagement lever may put the transmission into the engaged position, in which the user may be in a walking position with oppositionally aligned feet. The depicted natural-gait therapy device 1000 also includes a lifting pump handle 1010. The lifting pump handle may control the lifting and lowering of the seat 1015 and a user's body seated in the seat 1015. For example, when the lifting pump handle is pulled in a rearward direction, the hydraulic pump may raise the seat 1015 a quantified amount. Each pull of the lifting pump handle 1010 may further raise the seat 1015. The lifting pump handle may ratchet the seat toward a standing position as the lifting pump handle is pulled to and fro between a mid-forward position and a rearward position. If, however, the handle is pushed to a far-forward position, the hydraulic pump may then lower the seat to its transfer position. The depicted locked/engagement lever 1005 extends to the lateral side of the natural-gait therapy device impeding the throw of the lifting pump handle 1010. This imposition may perform an interlocking function. For example, if the locked/engagement lever 1005 is in the rearward position engaging the transmission, and the user attempts to push the lifting pump handle 1010 to its far-forward position, the lifting pump handle 1010 may encounter and contact the lateral extension of the locked/engagement lever 1005. If the user continues pushing the lifting pump handle 1010 to reach its far-forward position, the locked/engagement lever 1005 may be pushed to its forward position, locking the transmission. The foot position of the foot rests may then be transferred to their side-by-side position. A side-by-side foot position is the safe position for permitting a user to transition between a standing position and a sitting position. This interlocking feature may provide a safe side-by-side foot position for a user who attempts to sit before intentionally changing the transmission from engaged mode to locked mode.

Various means for interlocking the locked transmission mode to the pump release operation may be performed. In some embodiments, the interlock may be performed using electrical signals. For example, a position detector may generate an electronic signal indicative of the seat height position. If the seat height position begins to descend from the standing position, an electronic release of the feet positions may be initiated. In some embodiments, the pump may be prevented from performing a sitting operation until a user locks the transmission, for example.

Figure 11:
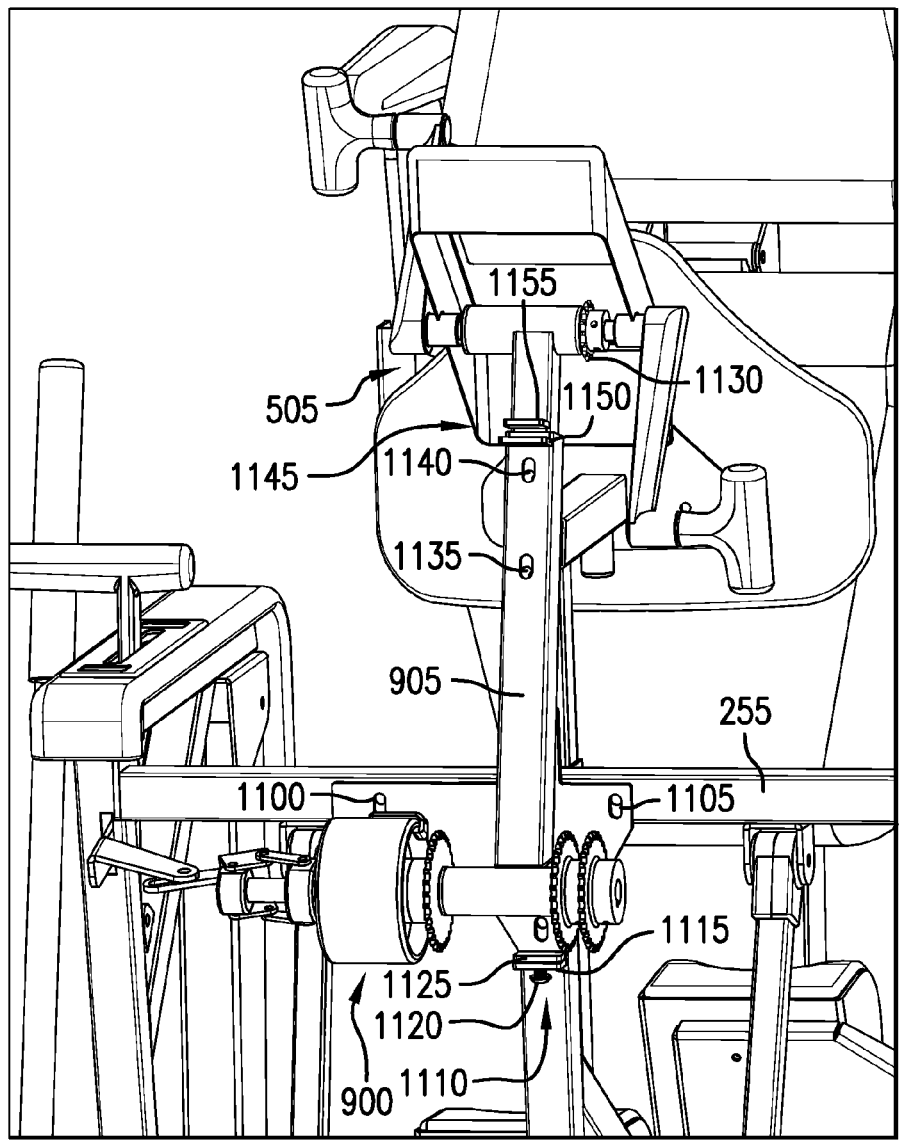
FIG. 11 depicts a perspective view of an exemplary natural-gait therapy device having independent upper and lower chain tensioning mechanisms.

FIG. 11 depicts a perspective view of an exemplary natural-gait therapy device having independent upper and lower chain tensioning mechanisms. In the FIG. 11 embodiment, an exemplary natural-gait therapy device 1100 includes a vertical support member 905 that is adjustably attachable to the cage 255. The vertical support member 905 provides support for the transmission module 900. The adjustable attachment may facilitate the tensioning of lower coupling chains which may couple the left-leg and right-leg drive gears 920, 935 to the left and right chain gears 430, 435. The depicted embodiment includes two slotted connection points 1100, 1105 and a screw tensioning module 1110. A threaded flange 1115 is coupled to the cage 255. A screw 1120 is threaded into the flange and impinges upon a flat flange 1125 that is attached to the vertical support member 905. When the screw is turned in a clockwise direction, the impinging end of the screw may push the vertical support member in an upward direction, thereby increasing the tension of the lower coupling chains. When the chains have sufficient tension for proper coupling operation, screws may be inserted into the slotted connection points 1100, 1115 to secure the vertical support member 905 to the cage 255 in the chain tensioned position.

The hand powertrain 505 is shown adjustably connected to the vertical support member 905 in a similar fashion. The depicted hand powertrain 505 includes a hand drive gear 1130. An upper coupling chain may couple the hand drive gear 1130 to the power drive gear 925 of the transmission module 900. The depicted hand drive gear 1130 may have fewer teeth than the power drive gear 925 so as to facilitate the ease of hand locomotion of a natural-gait, as depicted in FIG. 11. The adjustable attachment may facilitate the tensioning of the upper coupling. The depicted embodiment includes two slotted connection points 1135, 1140 and a screw tensioning module 1145. A threaded flange 1150 is coupled to the vertical support member 905. A screw may be threaded into the flange and may impinge upon a flat flange 1155 that is attached to the hand powertrain 505. When the screw may be turned in a clockwise direction, the impinging end of the screw may push the vertical support member in an upward direction, thereby increasing the tension of the upper coupling chain. When the chain has sufficient tension for proper coupling operation, screws may be inserted into the slotted connection points 1135, 1140 to secure the vertical support member 905 to the hand powertrain 505 in the chain tensioned position.

Although various embodiments have been described with reference to the Figures, other embodiments are possible. For example, in some embodiments, a bio stimulator may include a phase detection module. An exemplary phase detection module may provide a bio-stimulator unit information regarding the current phase of a natural-gait operation. In this way, the user may control the speed and manner of the natural-gait therapy, and the phase detection module will provide phase information in response to a user-controlled natural-gait phase. In some embodiments, a plurality of neurological stimulators may be controlled by a bio-stimulator unit. For example, one or more muscles may be stimulated by each of the neurological stimulators. In some embodiments, three or more neurological stimulators may be controlled for each leg of a user. In an exemplary embodiment, a quadriceps stimulator, a hamstring stimulator, and a calf stimulator may be controlled by an exemplary bio-stimulator unit.

In an exemplary embodiment, a bio stimulator may have parameters that are varied in response to one or more metrics of the gait cycle. For example, the intensity of a neurological stimulation may increase as the frequency of the gait increases. In some embodiments, a neurological stimulation may begin at a beginning phase associated with a gait cycle and end with an ending phase associated with a gait cycle. The beginning and/or ending phase may advance or retard as the frequency of the gait cycle increases, for example. The location of the muscle or muscle groups, the intensity, the waveform, the frequency of stimulation all may respond to the various gait cycle metrics, for example.

Figure 12C:
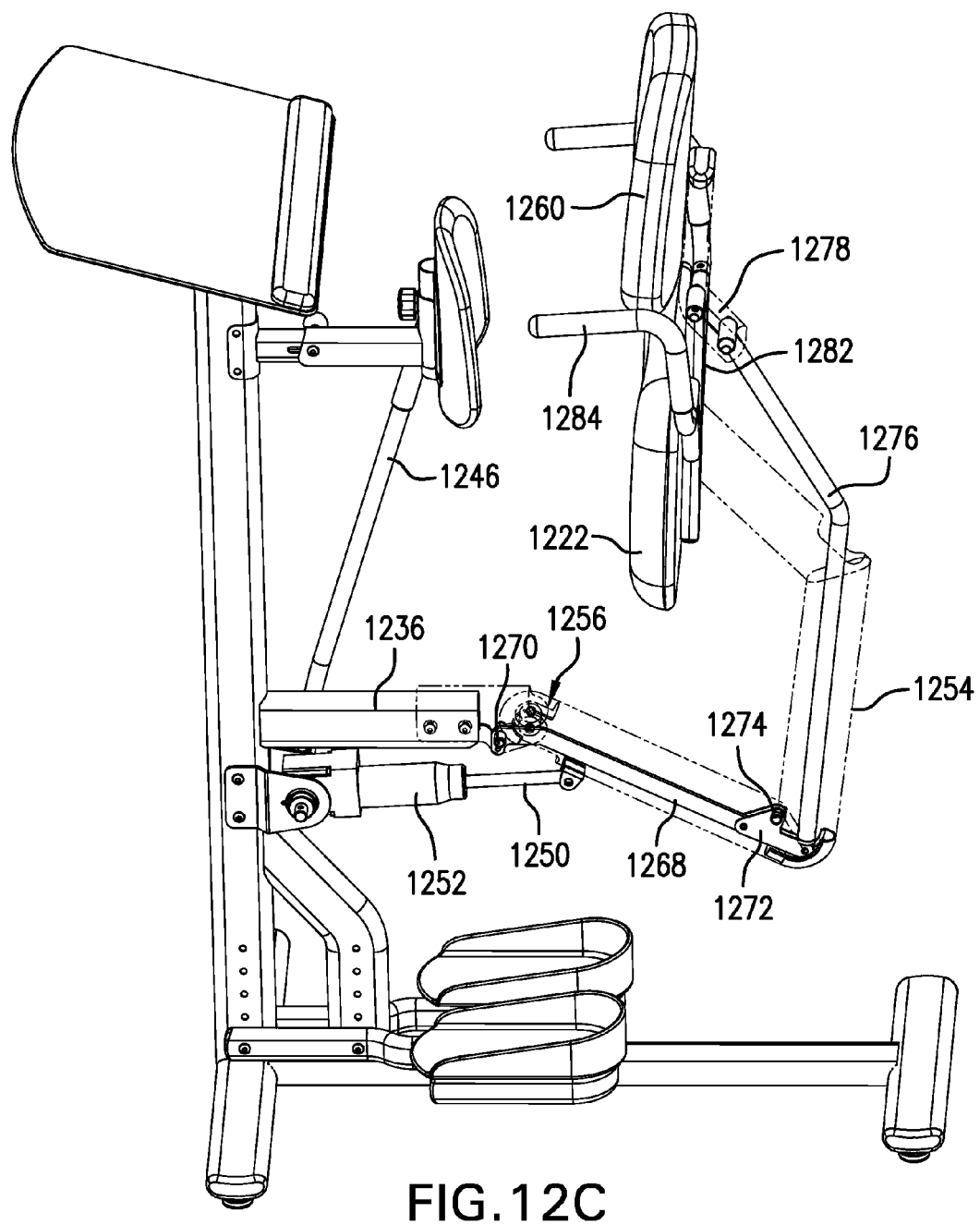

FIGS. 12A-12C depict an exemplary sit-to-stand therapy device. In FIG. 12A, an exemplary sit-to-stand therapy device 1200 is depicted in a perspective view. The depicted sit-to-stand therapy device 1200 includes an adjustable frame 1202, a pivotable seat assembly 1204 and means for pivoting the pivotable seat assembly 1204 from a sitting position to a standing position. In the depicted embodiment, the pivoting means includes a hydraulic pump system 1206. In some embodiments, the pivoting means may include an electric motor, for example. In an exemplary embodiment, the pivoting means may include a hydraulic piston that is electrically controlled. In some embodiments a pneumatic system may assist pivoting of the pivotable seat assembly 1210. A mechanical ratchet may pivot the pivotable seat assembly in some embodiments.

The adjustable frame 1202 of the depicted embodiment includes a ground-engaging base assembly 1208 and a vertical assembly 1210. The ground-engaging base assembly 1208 includes two transverse ground contacting members 1212 connected by a longitudinal member 1214. Each of the transverse ground contacting members 1212 has foot pads 1216 located at lateral ends 1218 of each transverse ground contacting member 1212. The foot pads 1216 may be Z-height adjustable, for example. Z-height adjustable foot pads 1216 may facilitate leveling of the sit-to-stand therapy device 1200. The longitudinal member 1214 has a longitudinal axis 1220 (e.g. X-axis) that is substantially coplanar with a median sagittal plane of a user seated upon the pivotable seat assembly 1204. By having the longitudinal member 1214 substantially coplanar with the median sagittal plane of a seated user, a wheel chair may be positions with a front wheel of the wheelchair adjacent to the longitudinal member 1214 and with a wheelchair's seat positioned adjacent to a seat bottom 1222 of the pivotable seat assembly 1204. The coplanarity of the longitudinal member 1214 and the median sagittal plane of a seated user may advantageously facilitate the close juxtapositioning of a wheelchair to the seat bottom 1222 from either side of the sit-to-stand therapy device 1200.

The depicted vertical assembly 1210 of the adjustable frame 1202 further includes a vertical beam 1224 which is braced by a bracing beam 1226. A torso engagement assembly 1228 projects from the vertical beam 1224 toward a user when seated in the pivotable seat assembly 1204. The torso engagement assembly 1228 includes a torso engagement pad 1230 and an adjustable connecting beam 1232. In some embodiments the torso engagement pad 1230 can be adjusted in the Y-direction. In some embodiments, the torso engagement pad 1230 can be adjusted in the Z-direction. The adjustment of the torso engagement pad 1230 may advantageously facilitate comfortable positioning of the torso engagement pad 1230 to a user's torso, when in the standing position.

The depicted vertical assembly 120 of the adjustable frame 1202 further includes a stand 1234. In some embodiments, the stand may provide securement devices to secure an object to the stand. For example, a ledge may support a base of a book upon the stand 1234. In some embodiments an electronic device may be secured upon the stand 1234. For example, a tablet computer may be secured to the stand 1234.

The depicted vertical assembly 1210 of the adjustable frame 1202 further includes a seat-assembly connecting beam 1236 projecting from the vertical beam 1224. The seat-assembly connecting beam 1236 supports a knee engagement assembly 1238. The knee engagement assembly 1238 may be adjustable. For example, the knee engagement assembly 1238 may be movable in the X-direction. An X-direction adjustment may facilitate a collinear positioning of knee pivot points as will be described below. The knee engagement assembly 1238 has two knee pads 1240. The separation distance (Y-direction separation) and/or the Z-height of the knee pads 1240 may be adjustable. In some embodiments, the knee pads 1240 may be slidably coupled to the knee engagement assembly 1238. In such embodiments, the knee pads may freely move in the Z-direction as the user is pivoted from a sitting position to a standing position. Such free movement may accommodated incidental changes in the Z-height of a user's knees as the user is pivoted from a sitting position to a standing position, for example.

Height adjustable foot rests 1242 are shown couple to the vertical assembly 1210. The height of the foot rests 1242 can be adjusted by selecting a pair of mounting holes 1244 for use in affixing the foot rests 1242 to the vertical assembly 1210. In some embodiments, the foot rests 1242 may be adjustably positioned along the longitudinal axis (X-direction adjustability).

The hydraulic pump system 1206 includes an operating handle 1246 that may be used to operate the hydraulic pump 1248. In some embodiments, the operating handle 1246 may be pulled back and forth (e.g. in the X-direction) to deploy a piston 1250 from a pump housing 1252 (as depicted in FIG. 12C). In an exemplary embodiment, pushing the pump handle to a far forward position (from a user's perspective) may permit the piston 1250 to be forced back into the pump housing 1252. A person's bodyweight may facilitate the forcing of the piston 1250 into the pump housing 1252, for example.

In FIGS. 12A-12B, the sit-to-stand therapy device is shown in the sitting position and the standing position, respectively. In both FIGS. 12A-12B, the knee engagement assembly 1238 has been hidden so as to facilitate the viewing of the pivotable seat assembly 1204. In FIG. 12B, the pivotable seat assembly 1204 includes a step-over connecting beam 1254 pivotable connected at a proximal-end pivot point 1256 to the seat-assembly connecting beam 1236. The step-over connecting beam 1254 is connected at a distal end to the seat bottom 1222. A seat-back attitude control assembly 1258 may maintain an attitude of a seat back 1260 throughout a movement of the pivotable seat assembly 1204 from a sitting position to a standing position. The step-over connecting beam 1254 has been made semi-transparent in FIGS. 12B-12C so that the seat-back attitude control assembly 1258, which travels within a hollow region of the step-over connecting beam 1254, can be seen.

When the pivotable seat assembly 1204 is in the sitting mode as is depicted in FIG. 12B, the step-over connecting beam 1254 may be traversed by the user's feet without requiring the feet to be raised high above an elevation of the foot rests 1242. The step-over connecting beam 1254 connects the seat bottom 1222 to the adjustable frame 1202. When in the sitting mode, the step-over connecting beam 1254 traverses a path from the knee pivot location down (Z-direction) to a proximal location near the floor and then longitudinally (X-direction) near a ground surface to a location rearward of the foot rests 1242, and then upward (Z-direction) to the seat bottom 1222. Such a traversal may provide leg space in front of the seat bottom 1222 for a user to laterally (Y-direction) transfer a leg across the median sagittal plane.

Leg transfer accommodating leg space may be improved by locating a longitudinal portion 1262 of the path of traversal of the step-over connecting beam as near to the longitudinal member 1214 of the base assembly 1208 as is practical. In an exemplary embodiment, for example, the step-over connecting beam 1254 may touch the longitudinal member 1214 when in the sitting position. A pivot descending portion 1264 of the step-over connecting beam 1254 may travel forward in its descent from the pivot point 1256. Such a forward angled profile may provide improved leg space for a user to laterally (Y-direction) transfer a user's foot across the median sagittal plane to a foot rest 1242.

A segmented central axis of the depicted step-over connecting beam 1254 is substantially coplanar with the median sagittal plane of the user, when seated. The segmented central axis of the step-over connecting beam 1254 is substantially coplanar with the longitudinal axis 1220 of the longitudinal member 1214 or the base assembly 1208. Wheelchair access to the sit-to-stand therapy device may not be further inhibited by the step-over connecting beam 1254, due to the coplanarity of the segmented central axis of the step-over connecting beam 1254 and the longitudinal axis 1220 of the longitudinal member 1214.

In some embodiments, a support block may be interposed between the longitudinal member 1214 and the step-over connecting beam 1254. The support block may determine a seat bottom height above a ground surface, for example. In some embodiments the support block may be adjustable. For example, the seat height may be adjustably set above a floor surface for accommodating transfer from wheelchairs of different seat heights. In some embodiments, the support block may be replaceable. For example, a support block may be selected from a set of support blocks of different dimensions corresponding to different seat heights. In an exemplary embodiment, a seat height may be set by a limiting member interposed between the brace member 1226 and the step-over connecting beam 1254. In some embodiments, dimensions of the hydraulic pump 1248 with the piston 1250 fully retracted into the piston housing 1252 may determine the seat height, when in the sitting position.

In the FIG. 12B embodiment, the foot rests 1242 may be vertically adjustable so that a knee-height distance 1266 between the footrests 1242 and the pivot point 1256 may be substantially equal to the distance between a user's sole of the foot to a user's knee pivot point. When a user has placed a user's feet in the foot rests 1242 and the user's knees against the knee rests 1240, the pivot points of the user's knees may be collinear with the pivot point 1256 of the pivotable seat assembly 1204. When the pivot points are so aligned, a user's seat may rest upon the seat bottom 1222 at a fixed distance from the pivot point 1256. As the seat bottom 1222 is raised to a standing position, the fixed distance between a pivot points of the user's knee and the user's seat may be substantially equal to the fixed distance between the pivot point 1256 and the seat bottom 1222 at the point of contact with the user's seat. The substantially equal distances between the contacting points of the user's body and the contacting points of the sit-to-stand therapy device may advantageously facilitate a user's elevation from a sitting position to a standing position without subjecting the contacting body features to sheer forces.

In FIG. 12C, the pivotable seat assembly 1204 is depicted in a standing position. The step-over connecting beam 1254 has been pivoted about a pivot point 1256 by the hydraulic pump 1248. In the depicted embodiment, the pivotable seat assembly 1204 is configured as a class 3 lever, wherein the effort is between the fulcrum and the resistance. In the exemplary embodiment, the hydraulic pump 1248 serves as the effort, and the pivot connection 1256 serves as the fulcrum. The resistance is the weight on the distal end of the pivotable seat assembly 1204.

The seatback attitude control assembly 1258 includes a first linkage member 1268 that is pivotably coupled at a proximal end pivot point 1270 to the seat-assembly connecting beam 1236. The first linkage member 1268 is then connected at a distal end to a pivot lever 1272 at an effort location. The pivot lever 1272 has a pivotable fulcrum 1274 connected to the step-over connecting beam 1254. A second linkage member 1276 is connected at a proximal end to an effort location of the pivot lever 1268. The second linkage member 1276 is then connected at a distal end to a seatback control lever 1278 at an effort location. A fulcrum 1280 of the seatback control lever 1278 is pivotably connected to the seat bottom member 1282. The described mechanism of the seatback attitude control assembly 1258 may maintain the seatback 1260 in a substantially vertical orientation independent of an elevation of the seat bottom 1222. The first 1268 and second 1276 linkage members as well as the pivot lever 1272 run substantially within a hollow cavity of the step-over connecting beam 1254. By locating portions of the seatback attitude control assembly 1258 within a cavity of the step-over connecting beam 1254, the pivotable seat assembly 1204 may present a small form factor to facilitate a user's entry and exit from the sit-to-stand therapy device 1200.

The depicted sit-to-stand therapy device 1200 may be used by individuals who are unable and/or have difficulty rising from a sitting position to a standing position. The sit-to-stand therapy device 1200 may support a standing user and/or help the user remain standing. A user's seat may be transferred from a wheelchair to the seat bottom 1222, for example. A user's feet may be transferred into the adjustably located foot rests 1242. The seat bottom 1222 may then be raised to lift the user to a standing position. The user may ratchet the pump handle 1246 to ratchet the seat bottom 1222 to a desired vertical position and/or horizontal position. As the seat bottom 1222 may be pivoted from the sitting position to the standing position, a normal vector of an seat-engaging surface of the seat bottom 1222 may rotate from a substantially vertical orientation (e.g. aligned with Z-direction) to a substantially forward lateral orientation (e.g. aligned with X-direction). When in the standing position, the normal vector of the engagement surface of the seat bottom 1222 and a normal vector of an engagement surface of the seat back 1260 may be oriented in substantially the same direction. When in the standing position, the seat bottom 1222 and/or the seat back 1260 and the torso engagement pad 1230 may substantially oppose one another. When so opposed, the torso engagement pad 1230 and the seat bottom 1222 and/or seat back 1260 may sandwich a user therebetween.

Figure 12D:
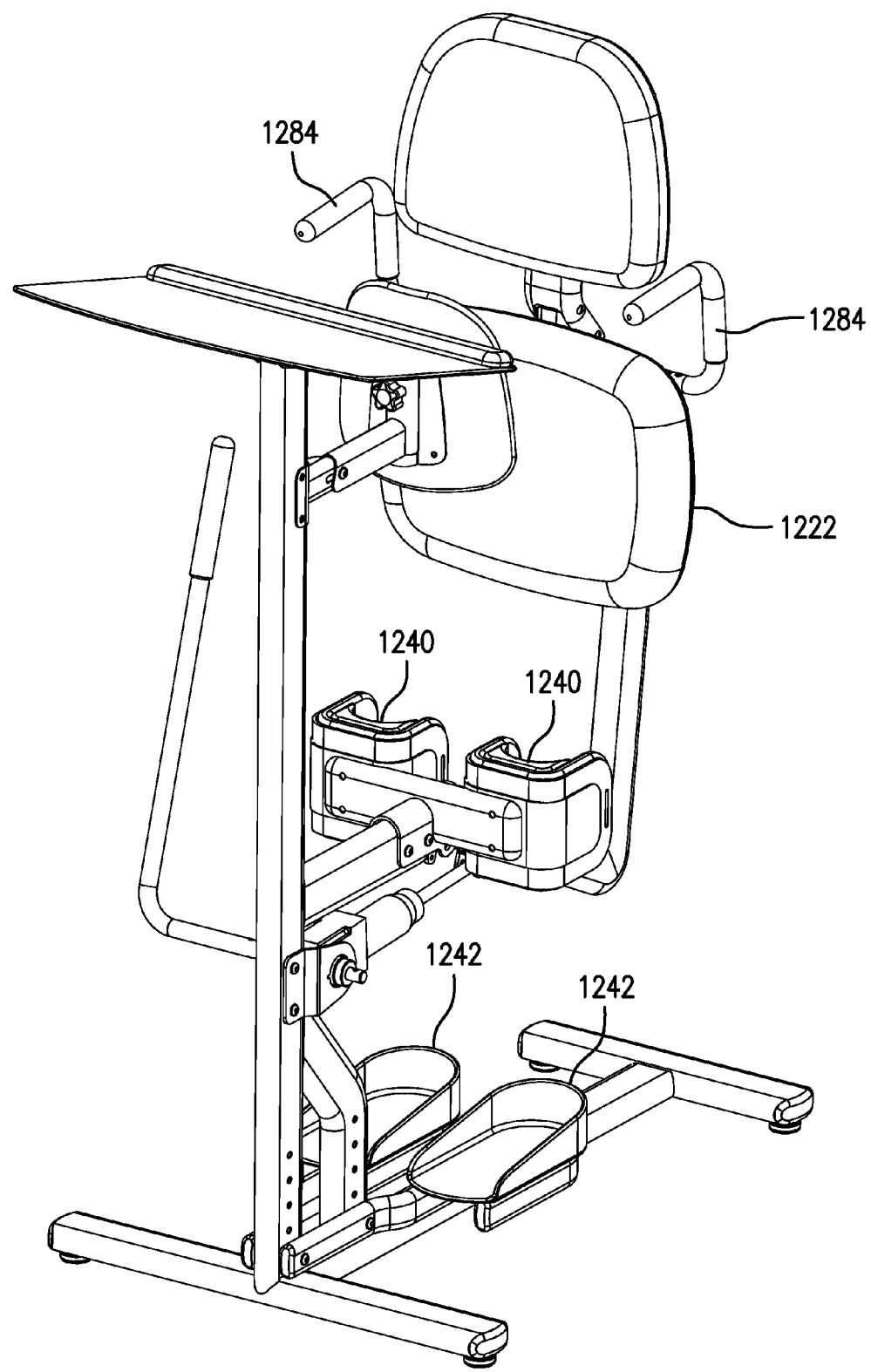

FIG. 12D depicts the sit-to-stand therapy device 1200 in a standing configuration with the knee pad assembly 1238 unhidden. The arm rests 1284 may facilitate the lateral securing of a user's body within the sit-to-stand therapy device 1200, especially when in the standing position. A user would be make contact with the foot rests 1242, the knee pads 1242, the torso engagement pad 1230 and the seat bottom 1222. Note that, in the depicted embodiment, arm rests 1284 may be pivoted with respect to the seat bottom 1222. The arm rests 1284 may prevent the user from laterally falling when in the standing position.

Facilitating a user, who are otherwise unable, to stand may have many positive health benefits. For example, by providing weight bearing on the user's legs, bone integrity may be improved. Bone density, can be improved when bones are forced to bear loads. A user's circulation may improve by exercising in such a manner. Improved renal function may result from regular use. In some circumstances improved range of motion can result.

FIGS. 13A-13B depicts a perspective view of an exemplary natural-gait therapy system.

In FIG. 13A, an exemplary natural-gait therapy system 1300 is in a sitting position. The depicted natural-gait therapy system 1300 includes an exemplary protective cover 1305 that covers many of the moving parts of the natural-gait therapy system 1300. The depicted natural-gait therapy system 1300 includes a sit-to-stand locomotion system 1310, a natural-gait locomotion system 1315, and a stand-to-walk transmission system (obscured by the protective cover 1305 in this perspective view). In some embodiments, the sit-to-stand locomotion system 1310 may be similar to systems described with reference to FIGS. 12A-12D.

In FIG. 13B, an exemplary natural-gait therapy system 1320 is in a sitting mode. The depicted natural-gait therapy system 1320 includes an exemplary protective cover 1325 that covers many of the moving parts. The depicted natural-gait therapy system 1320 includes a sit-to-stand locomotion system 1330, a natural-gait locomotion system 1335, and a stand-to-walk transmission system (obscured by the protective cover 1325 in this perspective view). In some embodiments, the sit-to-stand locomotion system 1330 may be similar to systems described with reference to FIGS. 12A-12D. The natural-gait locomotion system will be described below, with reference to FIGS. 14A-14D.

Figure 14A:
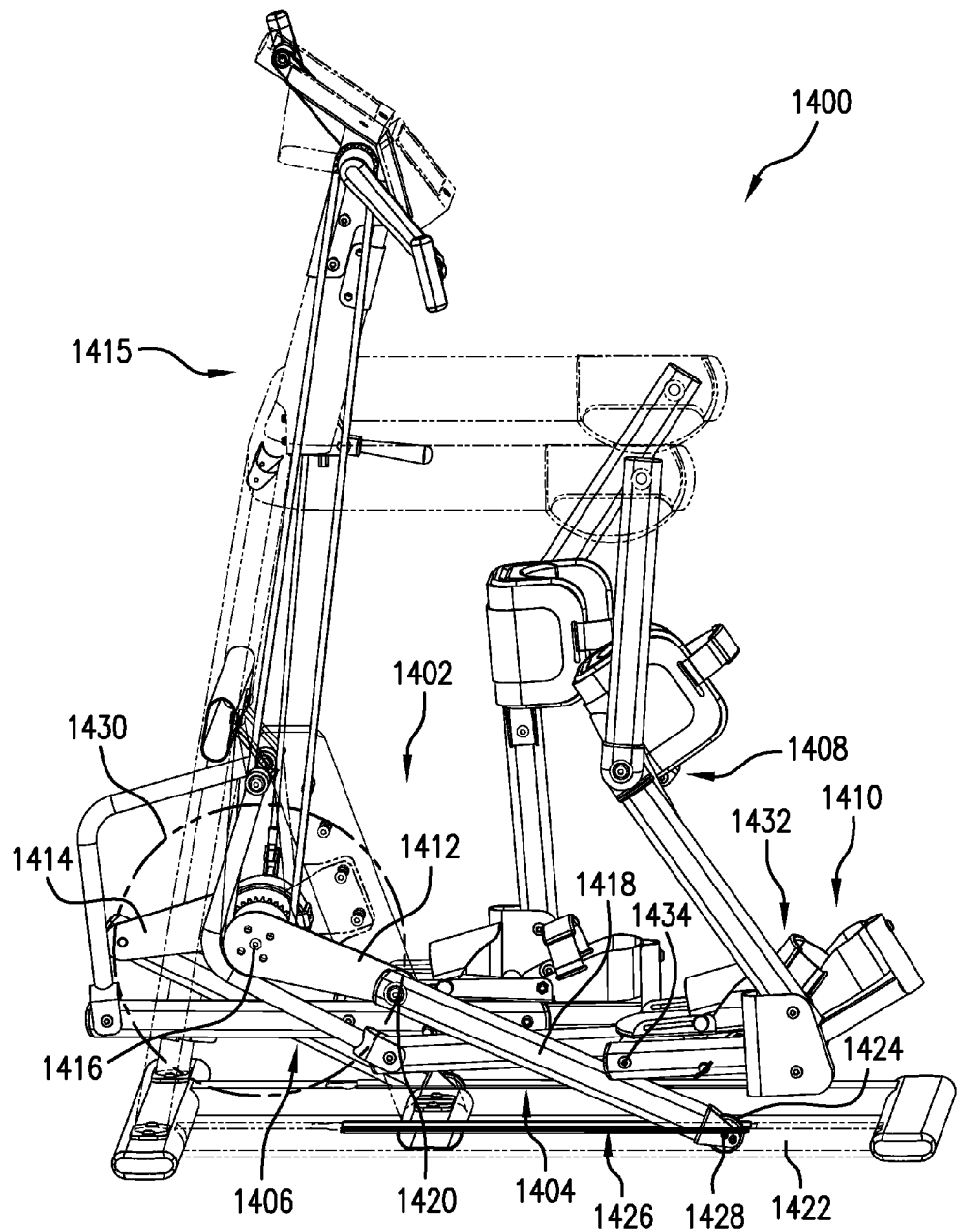
FIGS. 14A-14D depict an exemplary natural-gait therapy system without a protective covering and without a pivotable seat assembly.

FIGS. 14A-14D depict an exemplary natural-gait therapy system without a protective covering and without a pivotable seat assembly. The protective covering and pivotable seat assembly have been hidden in these figures so that a natural-gait locomotion system may be better viewed. The FIGS. 14A-14D depictions show a natural-gait therapy system in a walking mode. When in the walking mode, the two foot rests are operatively coupled at opposite phases of a natural-gait cycle. For example, when one footrest is forward moving, the other footrest will be backward moving. FIG. 14A depicts an exemplary natural-gait therapy system 1400. The depicted natural-gait therapy system 1400 includes a natural-gait locomotion system 1402. The natural-gait locomotion system 1402 includes a toe-position control system 1404, a forefoot-angle control system 1406, knee-position control system 1408 and a heel-lift control system 1410.

The toe-position control system 1404 includes a left crank arm 1412 that is operatively coupled and out-of-phase with a right crank arm 1414. The left 1412 and right 1414 crank arms each rotate in response to locomotion of a power system 1415. The left 1412 and right 1414 crank arms each rotate the about a crank shaft axis. Each crank arm 1412, 1414 is coupled to a crank shaft at a proximal end 1416. Each crank arm 1412, 1414 is pivotably coupled to a drive arm 1418 at a distal-end pivot point 1420. The drive arms 1418 are pivotably coupled to the crank arms 1412 at a proximal end. Each drive arm 1418 is slidably coupled to a longitudinal frame member 1422 at a distal end.

Various means for slidably coupling the distal end of the drive arm 1418 to the longitudinal frame member 1422 can be realized. For example, in the depicted embodiment, a rolling wheel 1424 is coupled to the distal end of the drive arm 1418. The longitudinal frame member 1422 has a guide channel 1426 in which the rolling wheel 1424 may travel. The rolling wheel 1424 may have an axle 1428 laterally projecting from one side or both sides of the rolling wheel 1424. The projecting axle 1428 may extend beyond the guide channel 1426 and within a cavity in the longitudinal frame member 1422. This projecting axle 1428 may serve to retain the distal end of the drive arm 1418 within the guide channel 1426, for example.

As the crank arms 1412 rotate about the axis of the crank shaft, the pivot point 1420 traverses a circular orbit 1430 about the crank shaft axis. Thus, the motion of the proximal end of the drive arm 1418 is substantially circular at the pivot point 1420. If one assigns the origin of an X-Z coordinate system to be at the crank shaft axis, the circular orbit 1430 can be described as:

$$x_1^2 + z_1^2 = r^2$$

Here, r is the radius of the pivot point with respect to the crank shaft axis.

The distal end of the drive arm 1418 is substantially linear as a result of the slidable coupling. The position of the distal end of the drive arm 1418 is linear, but related to the circular position 1430 of the pivot point 1420. The z coordinate of the distal end is fixed ($z_2$). But the x coordinate of travel is related to the circular coordinate system by way of the distance, L, form the pivot point 1420 to the axel 1428 of the rolling wheel 1424:

$$x_2 = x_1 + \sqrt{L^2 - (z_2 - z_1)^2}$$

Thus, as the pivot point 1420 is driven in its circular orbit 1430, the axel 1428 of the rolling wheel 1424 is linearly driven with fixed z coordinate, $z_2$, and a reciprocating x coordinate, $x_2$.

A foot rest 1432 is pivotably coupled to the drive arm 1418 at a location between the pivot point 1420 and the axel 1428 of the rolling wheel 1424. The foot rest 1432 is thus driven at a pivot point 1434 by the drive arm 1418. The path of travel of the pivot point 1434 is neither perfectly circular, nor perfectly linear, but some relation to both of these. The coordinates of travel for the pivot point is approximately given by:

$$(\alpha x_1 + (1-\alpha)x_2, \alpha z_1 + (1-\alpha)z_2)$$

Here α is the ration of the distance from the pivot point 1418 to the pivot point 1434 and the distance from the pivot point 1418 to the axel 1428 of the rolling wheel 1424. This path of motion of the pivot point 1434 of the foot rest 1432 may approximate a natural gait motion of a human. In the depicted embodiment, the toe-position control system 1404 responds to power system 1415 and positions the foot rest 1432 at a predetermined location for each phase of a natural-gait cycle.

Figure 14B:
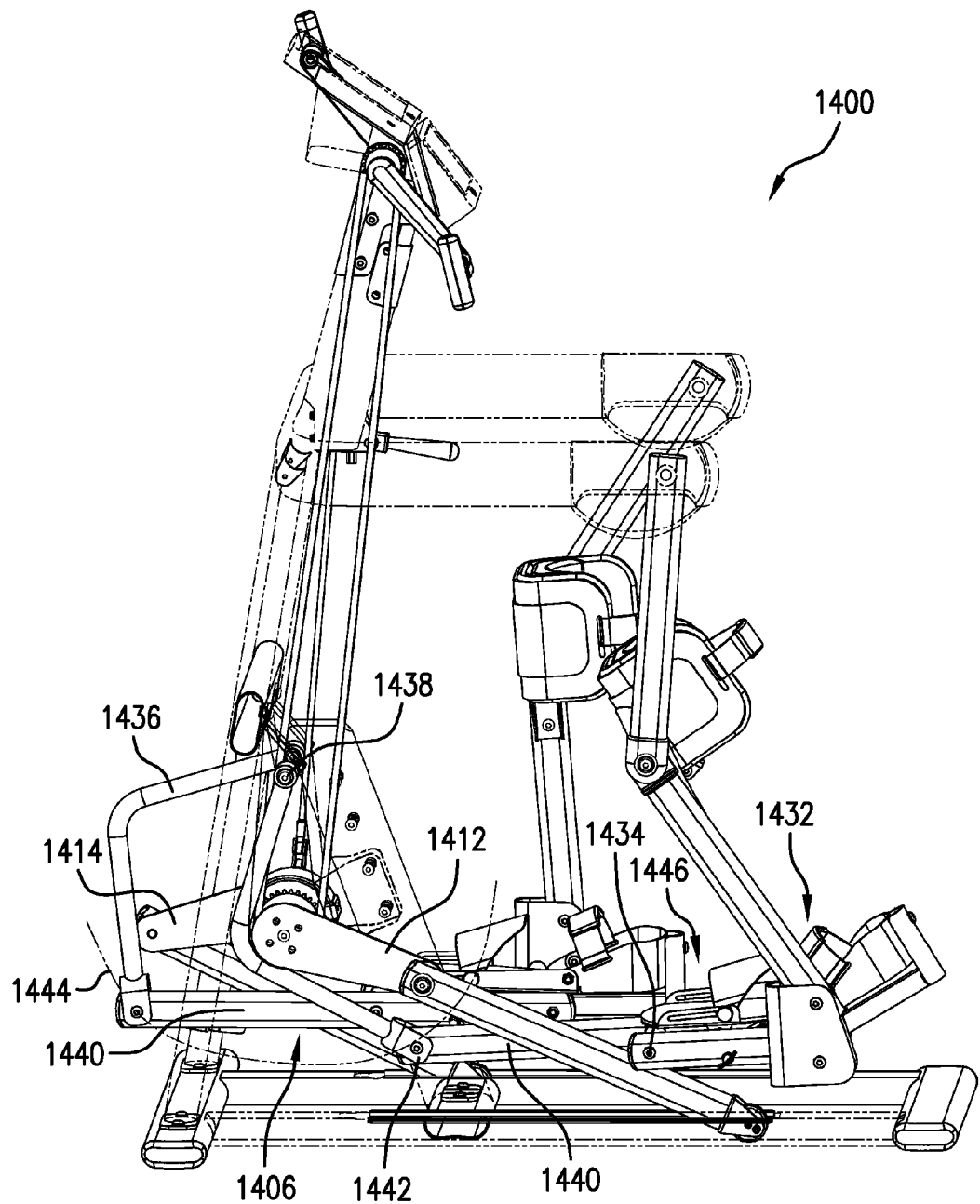

FIG. 14B depicts the exemplary natural-gait therapy system 1400 shown in FIG. 14A. This figure will be used to describe the forefoot angle control system 1406. The forefoot angle control system 1406 includes a pendulum member 1436 pivotably coupled to the frame at a proximal-end pivot point 1428. The pendulum member 1436 is also pivotably coupled to a foot rest beam 1440 at a distal-end pivot point 1442. The travel of the distal-end pivot point 1442 is along a circular arc 1444 about the proximal-end pivot point 1438. The circular arc 1444 lies on the circle defined by:

$$(x_4 - x_3)^2 + (z_4 - z_3)^2 = P^2$$

Here, P is the radial distance of the pivot point 1442 from the pivot point 1438 of the pendulum members 1436. The point ($x_3$, $z_3$) is the coordinate of the pivot point 1438. The coordinate ($x_4$, $z_4$) describe the path of travel for the pivot point 1442. The angle of a forefoot portion 1446 of the foot rest 1432 is determined by the relative heights (z-coordinates) of the pivot point 1442 and the pivot point 1434 (e.g. the relative values of z4 and $\alpha z_1 + (1-\alpha)z_2$).

The exemplary pendulum members 1436 have a bent-knee shape so as to permit them to travel swing back and forth without impinging the power system 1415. Because the pendulum members 1436 are shaped to avoid other elements of the natural-gait therapy system 1400, the pendulum members may located laterally interior to the crank arms 1412, 1414. Such interior locations of the pendulum members 1436 may result in a narrow form factor for the natural-gait therapy system 1400. In the depicted embodiment, the forefoot angle control system 1406 responds to movement of the toe position control system 1404 and provides a predetermined angle of the forefoot portion 1446 of the foot rest 1432 at each phase of the natural-gait cycle.

Figure 14C:
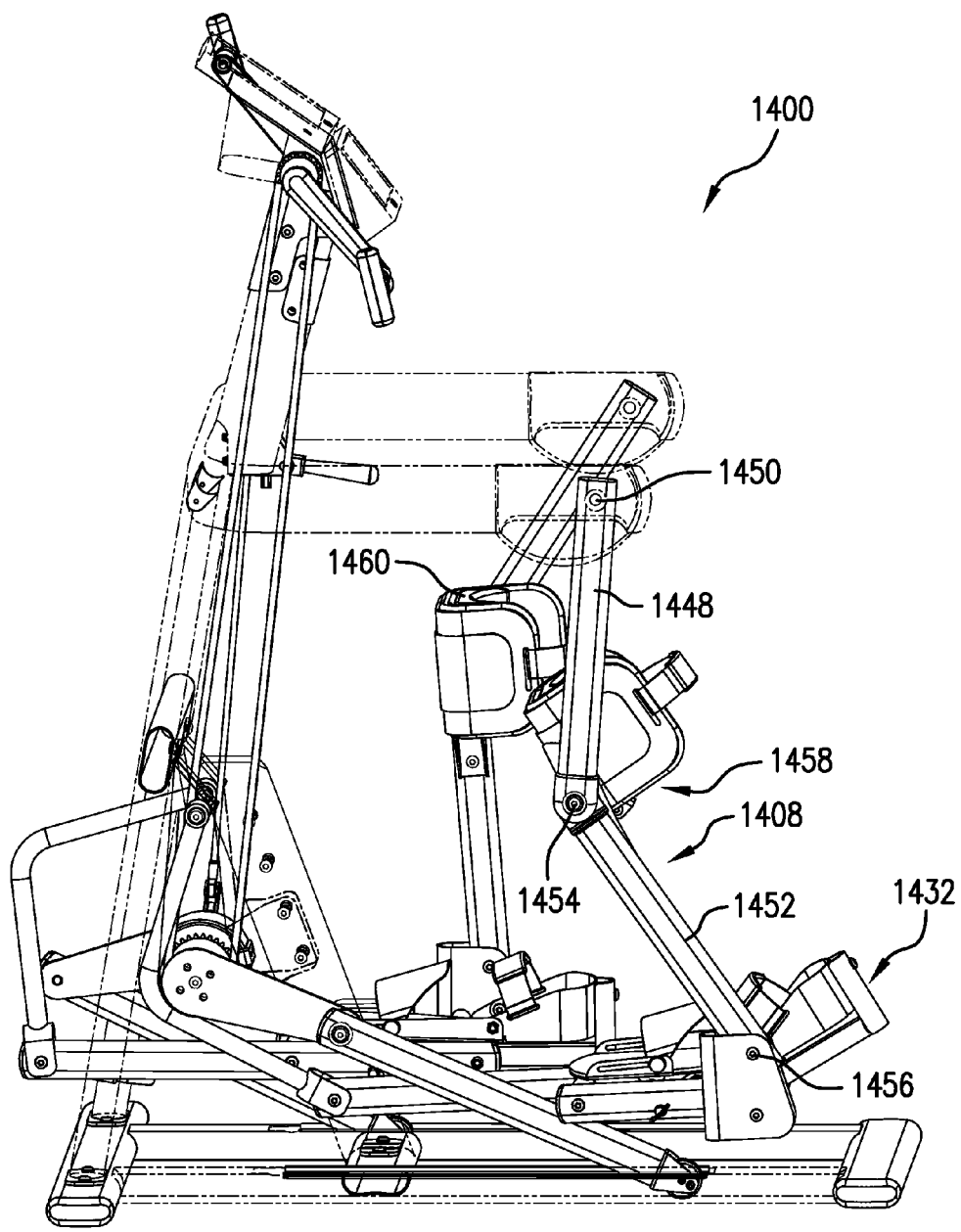

FIG. 14C depicts the exemplary natural-gait therapy system 1400 shown in FIGS. 14A-14B. This figure will be used to describe the knee-position control system 1408. The knee-position control system 1408 includes an upper leg member 1448 pivotably attached to the frame at a hip-end pivot point 1450. The upper leg member 1448 is also pivotably coupled to a lower leg member 1452 at a knee-end pivot point 1454. The lower leg member 1452 is pivotably coupled to the foot rest 1432 at an ankle-end pivot point 1456.

As the foot rest 1432 is driven along its path of travel as described above, the knee-end pivot point 1454 may be propelled along its own path of travel. In response to the coordination of the toe-position and the forefoot angle of the forefoot portion 1446 of the foot rest 1432, the ankle-end pivot point 1456 moves along a path of travel. As the separation distance between the ankle-end pivot point 1456 and the hip-end pivot point changes, a knee joint 1458 may flex and/or unflex. The x-z alignment of the various pivot points with corresponding anatomical pivot points of a user facilitate a natural-gait motion of operation. Thus, the relative position of the ankle-end pivot point 1456 with respect to the foot rest 1432 may correspond to a relative position of an ankle joint to a sole of a foot of a human. And again, the relative lengths of the lower leg member 1448 to the upper leg member 1448 may correspond to the relative lengths of a human's lower leg and upper leg.

The upper leg member 1448, knee joint 1454 and lower leg member 1452 are laterally located outside the foot rests 1432 so as not to interfere with a human user positioned upon the foot rests 1432. Thus, the knee pads 1460 project inward from the knee-position control system 1408. In some embodiments, the knee pads 1460 are supported by a projecting beam coupled to the lower leg members 1452. In some embodiments the knee pads 1460 are supported by a projecting beam coupled to the upper leg members 1448. In an exemplary embodiment, the knee pads 1460 are supported by a projecting beam coupled to the knee joint 1458. In the depicted embodiment, the knee-position control system 1408 responds to the coordinated movements of the toe position control system 1404 and the forefoot-angle control system 1406 and provides a predetermined positioning of the knee pads 1460 at each phase of the natural-gait cycle.

Figure 14D:
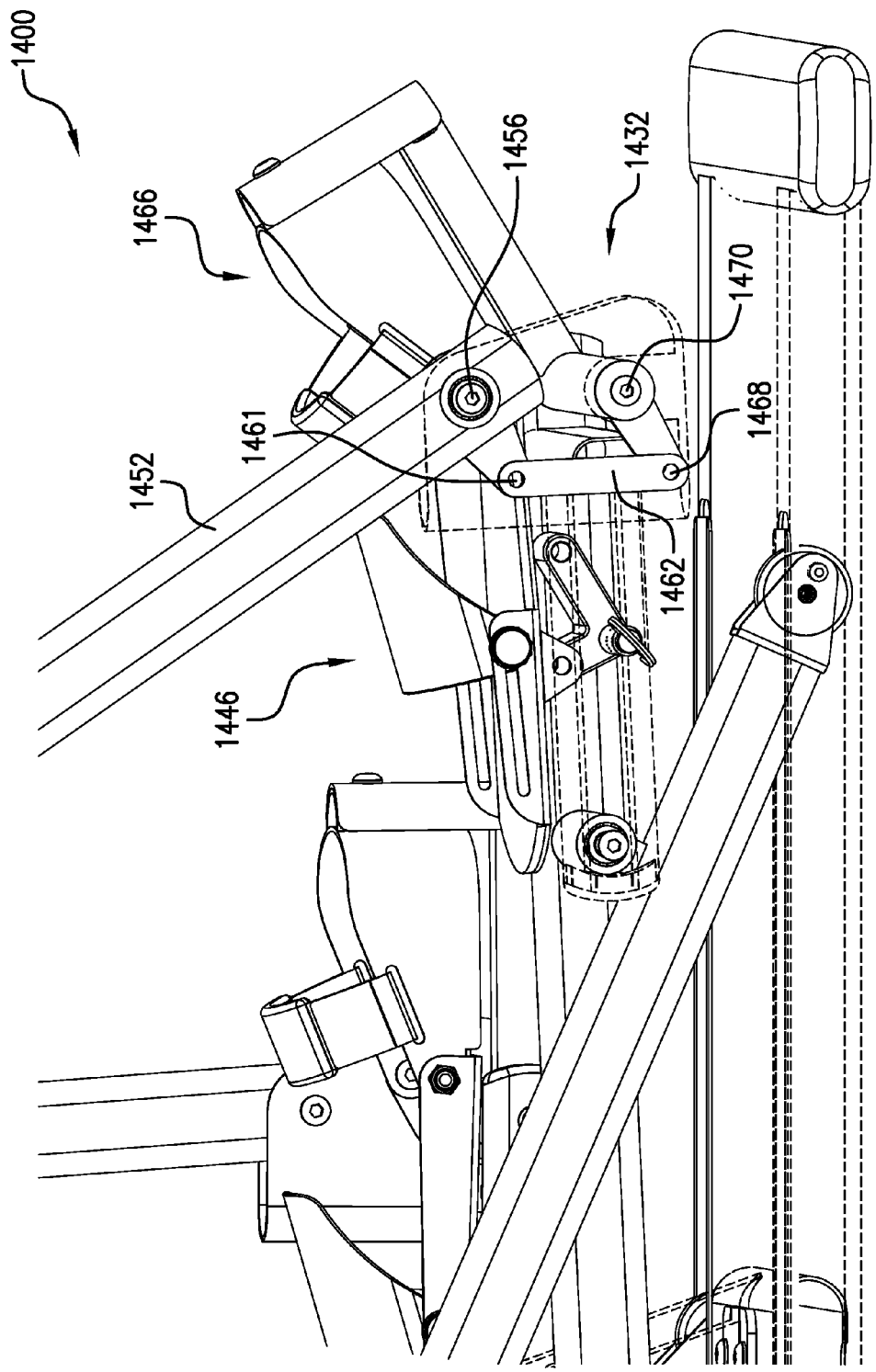

FIG. 14D depicts the exemplary natural-gait therapy system 1400 shown in FIGS. 14A-14C. This figure will be used to describe the heel-lift control system 1410. The heel-lift control system 1410 includes a control arm 1462 pivotably coupled to the lower leg member 1452 at a proximal-end pivot point 1464. The control arm 1462 is also pivotably coupled to a heel portion 1466 of the foot rest 1432 at a distal-end pivot point 1468. As the lower leg member 1452 pivots about the heel-end pivot point 1456, the angle of the lower-leg member 1452 with respect to the forefoot portion 1446 of the foot rest 1432 changes. As this angle changes, the proximal end pivot point 1464 travels along an arc about the heel-end pivot point 1456. The control arm 1462 in turn moves and causes the distal-end pivot point 1468 to travel on an arc about a heal pivot point 1470. Because the distal-end pivot point 1468 is pivotably coupled to the heel portion 1466 of the foot rest, when the distal-end pivot point 1468 travels on its arc, the heel portion 1466 of the foot rest 1432 lifts and/or falls.

The amount of lift that results from a given angle between the lower leg member 1452 and the forefoot portion 1446 of the foot rest 1432 may be determined by the ratio of the separation distance of the heel-end pivot point and the proximal-end pivot point to the separation distance of the distal-end pivot point to the heal pivot point 1470. In the depicted embodiment, the heel-lift control system 1410 responds to the coordinated movements of the toe position control system 1404, the forefoot-angle control system 1406, and the knee-position control system 1408 and provides a predetermined amount of lift to the heal portion 1466 of the foot rest 1432 at each phase of the natural-gait cycle.

Figure 15:
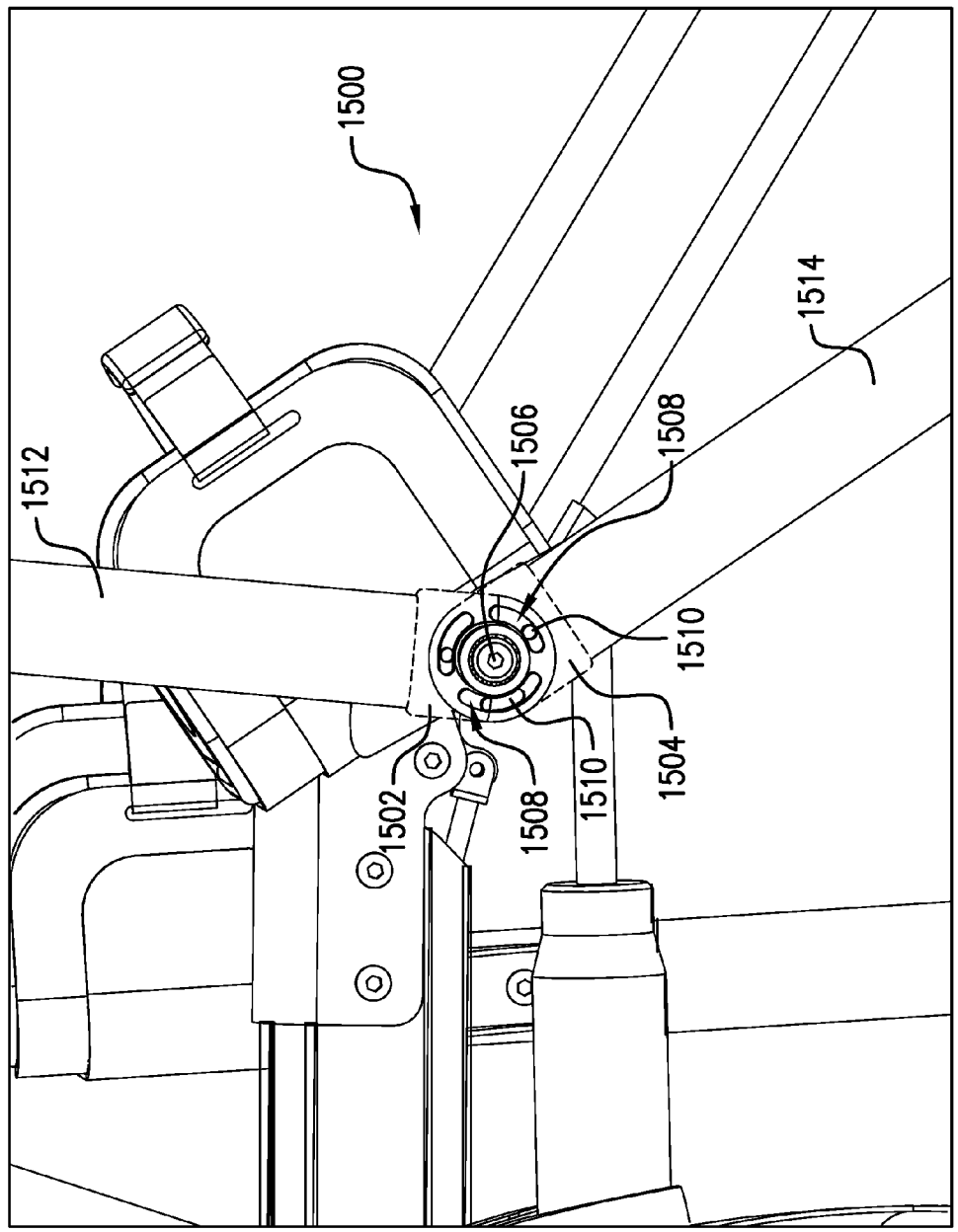
FIG. 15 depicts an exemplary embodiment of a knee position control system with hyperextension protection.

FIG. 15 depicts an exemplary embodiment of a knee position control system with hyperextension protection. An exemplary therapy-system knee joint 1500 is depicted that includes an upper-leg connecting member 1502 pivotably coupled to a lower-leg connecting member 1504 at a knee pivot point 1506. The upper 1502 and lower 1504 connecting members have complementary rotational limiting features for preventing hyperextension of a user's knee joint. The upper 1502 and lower 1504 connecting members have been drawn in transparent fashion so as to permit view of these complementary rotational limiting features. One of the upper 1502 or lower 1504 connecting members has a rotational slot 1508, while the other has a projecting feature 1510 that projects into the rotational slot 1508 when the two connecting members 1502, 1504 are pivotably coupled to each other.

In the depicted embodiment, three rotational slots 1508 are present. In some embodiments more or fewer slots may be provided. Each slot provides an arc of travel for the projecting features 1510 that project therein. The arc of travel may permit the knee joint to pivot over a predetermined range of angles. For example, the relative angle between an upper leg member 1512 and a lower leg member 1514 may be freely permitted from 90 degrees to 180 degrees. But hyperextension of the knee may be prevented by the limited travel of the projecting features 1510 within the slots 1508. In some embodiments, the permitted angles of knee pivot may correspond to a range of angles encountered throughout a cycle of the natural gate motion as described above.

Figure 16A:
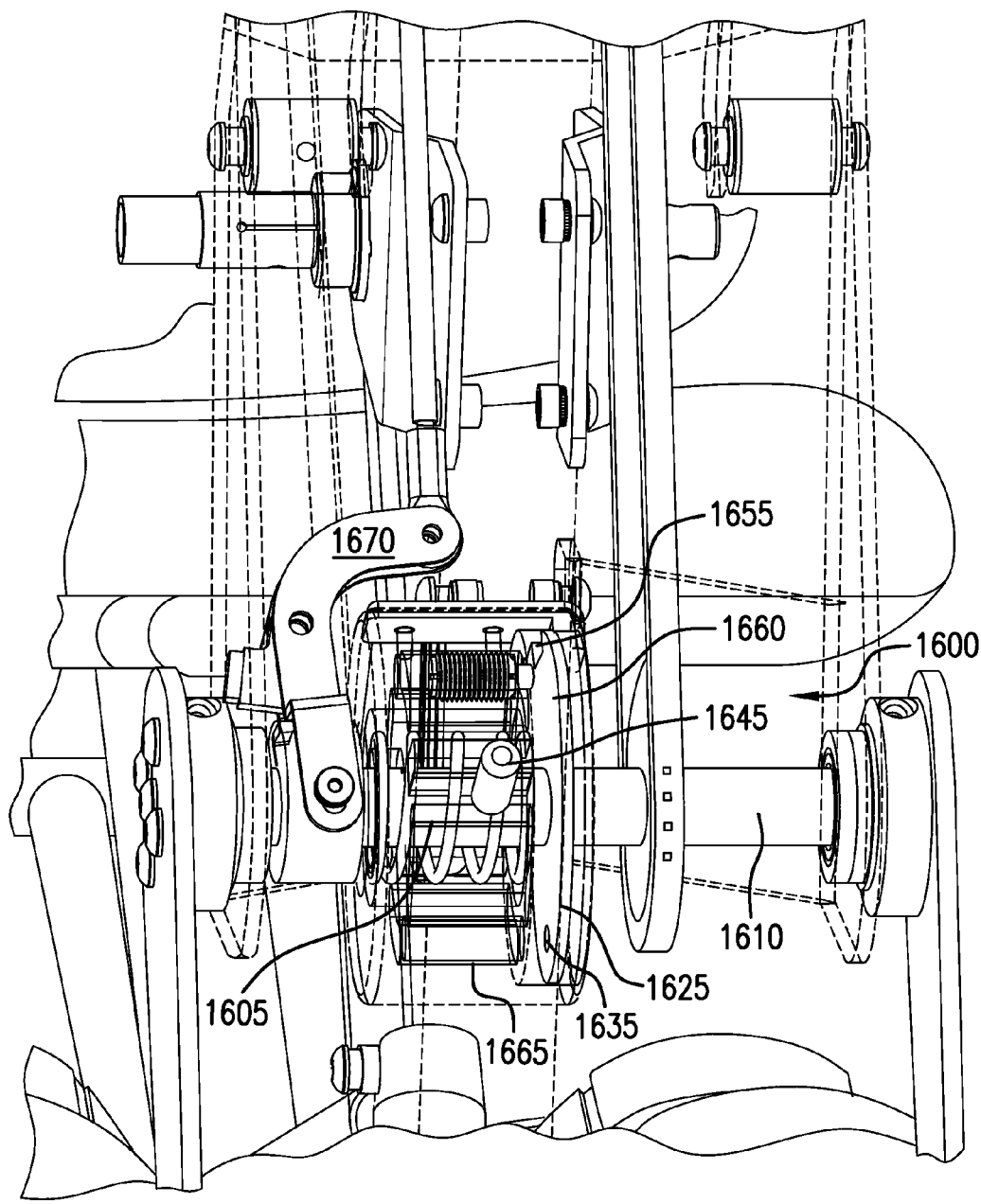
FIGS. 16A-16B depict an exemplary stand-to-walk transmission system.
Figure 16B:
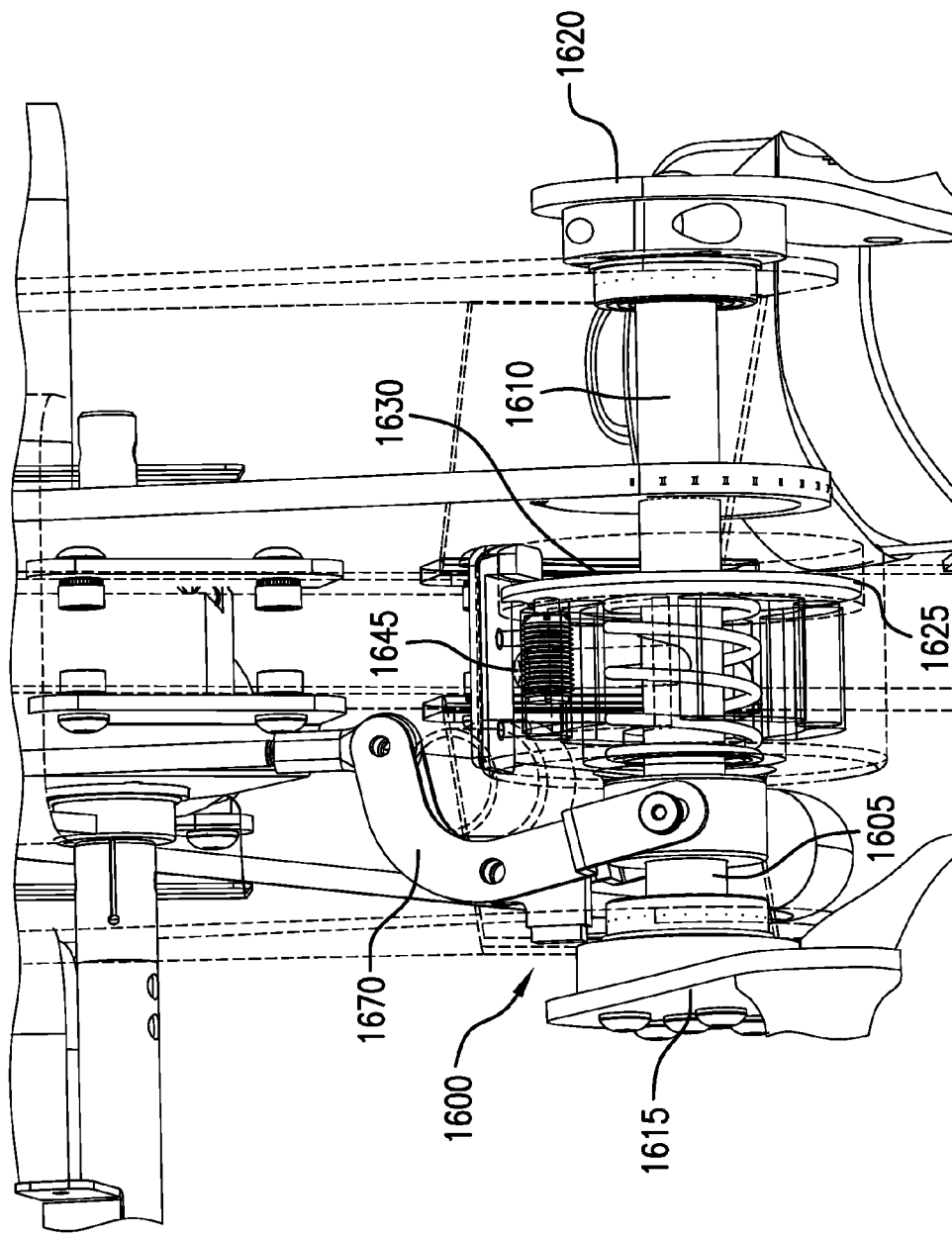

FIGS. 16A-16B depict an exemplary stand-to-walk transmission system. FIGS. 16A-16B make a transmission housing transparent so as to make visible the elements within. FIG. 16A depicts a stand-to-walk transmission system 1600 in a standing mode. FIG. 16B depicts the stand-to-walk transmission system 1600 in a walking mode. The basic principle of the stand-to-walk transmission is to provide two phases coupling a right drive axle 1605 to a left drive axle 1610—0 degrees and 180 degrees.

The right drive axel 1605, and the left drive axle 1610 may be coupled to permit independent rotation of each drive axle 1605, 1610. The right drive axle 1605 and the left drive axle 1610 are axially aligned. In some embodiments, a cylindrical centering rod may be inserted within a cylindrical axial cavity in one or both drive axles 1605, 1610 to provide axial alignment. In an exemplary embodiment, one of the drive axels 1605, 1610 may have a cylindrical axial lumen, and the other drive axle 1610, 1605 may be solid, but have one side machined so as to be insertable into the cylindrical axial lumen of the other drive axle.

The right drive axle 1605 is coupled to a right crank arm 1615. The left drive axle 1610 is coupled to a left crank arm 1620. Each of the crank arms 1615, 1620 control the natural gait motion of the foot rests 1432 and knee pads 1460 as described above. A natural-gait motion is 'natural' when the left side foot rest 1432 and knee pad 1460 are approximately 180 degrees out of phase with the right side foot rest 1432 and knee pad 1460. Thus, to provide a natural-gait phase relationship between the two otherwise independently rotatable crank arms, the transmission may provide a means for locking the transmission in a 180 degree phase relation.

But when a person stands, the person's feet are normally side by side or "in phase." And when a person is in the process of transitioning from a sitting position to a standing position or vice-versa, a person often positions the feet side-by-side. A side-by-side foot arrangement may provide a safe configuration for sitting or standing, as each side of the body may move in a symmetrical fashion about a median sagittal plane. Thus, to provide a natural position for transitioning a user from a sitting position to a standing position and/or vice-versa, the transmission may provide a means for locking the transmission in a 0 degree phase relation.

To accomplish these two modes of phase-locking the left drive axle 1605 to the right drive axle 1610, each drive axle 1605, 1610 has a complementary locking member. In the depicted embodiment, the left drive axle 1610 is rigidly coupled to a left locking member 1625, in this embodiment in the form of a solid disk. The left locking member 1625 has a zero-degree locking feature 1630 and a 180 degree locking feature 1635. In this exemplary embodiment, the zero degree locking feature 1630 is in the form of a peripheral cutout of the left locking member 1625, and the 180-degree locking feature 1635 is in the form of an aperture interior to the periphery of the left locking member 1625.

The right axel 1605 is slidably coupled to a complementary right locking member 1640, in this embodiment in the form of a housing (shown in transparent fashion). The right locking member 1640 is rotational coupled to the right axle 1605 via rotational locking system. The rotational locking system includes a transverse coupling member 1645 that is rotationally coupled to the right drive axle 1605. Within the right locking member 1640 are opposing slots 1650 that are parallel to a rotational axis about which the right 1605 and left 1610 drive axles rotate. The transverse coupling member 1645 may slide within the opposing slots 1650. But the transverse coupling member 1645 and slots 1650 provide rotational coupling between the two members 1645, 1650.

The right coupling member 1640 has a zero-degree coupling member 1655, which, in this embodiment, includes a projecting feature configured to engage the zero-degree coupling recess 1630 of the left locking member 1625. In this embodiment, the zero-degree coupling member 1655 is in the form of a tab that, when engaged within the zero-degree coupling recess 1630 provides rotational coupling at zero degrees phase difference. The right coupling member 1640 also has 180-degree coupling member 1660 configured to engage the 180-degree coupling feature 1635 of the left locking member 1625. In this embodiment, the 180-degree coupling member 1660 is in the form of a spring loaded pin configured to engage the aperture of the left locking member 1625.

The right coupling member 1640 may be axially slid from a zero-degree phase position to a 180-degree phase position. When transitioning from the zero-degree phase position to the 180-degree phase position, the user may control a transmission lever 1670 to provide a force directing the slidable right locking member 1640 toward the left locking member. The force may be provided by a spring 1665, for example. And when transitioning from the 180-degree phase position to the zero-degree phase position, the user may control operate the transmission lever 1670 in a manner substantially inverse from the operation used to transition from the zero-degree phase position to the 180-degree phase position. Such an inverse operation may provide a force directing the slideable right locking member 1640 away from the left locking member 1625, for example.

In the depicted embodiment, a drive belt 1675 may provide power to rotate the left drive axle 1610. When transitioning either from the zero-degree phase relation to the 180-degree phase relation or vice versa, rotating the left drive axle 1610 will result in only the rotation of the left drive axle 1610 until the complementary locking members 1625, 1640 become coupled in the intended phase manner. When transitioning from a walking position to a standing position, the weight of a user's body may facilitate a rapid transition to a zero-degree phase relation when both foot rests attain their minimal gravitational energy position (e.g. their lowest z-height).

Figure 17A:
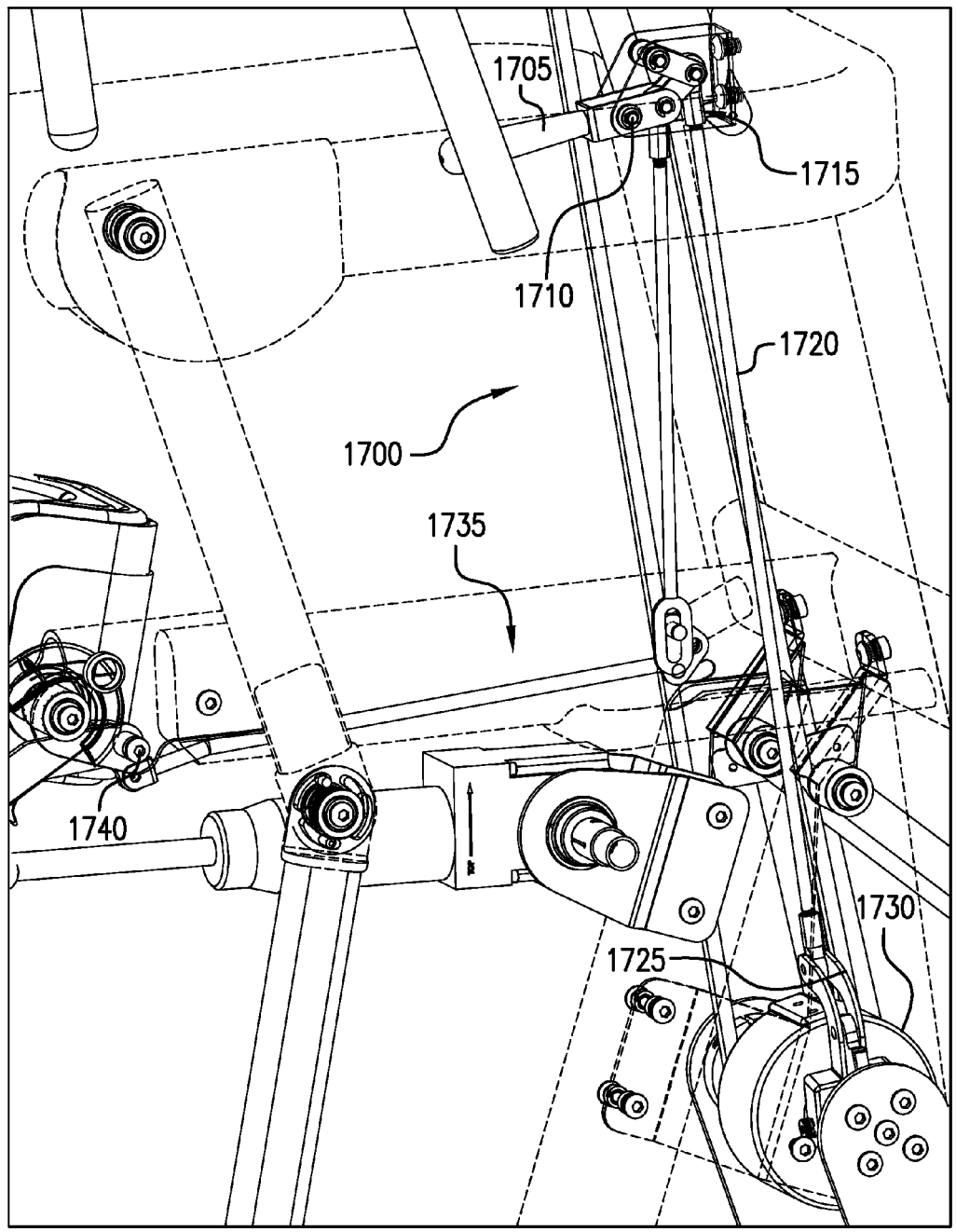
Figure 17B:
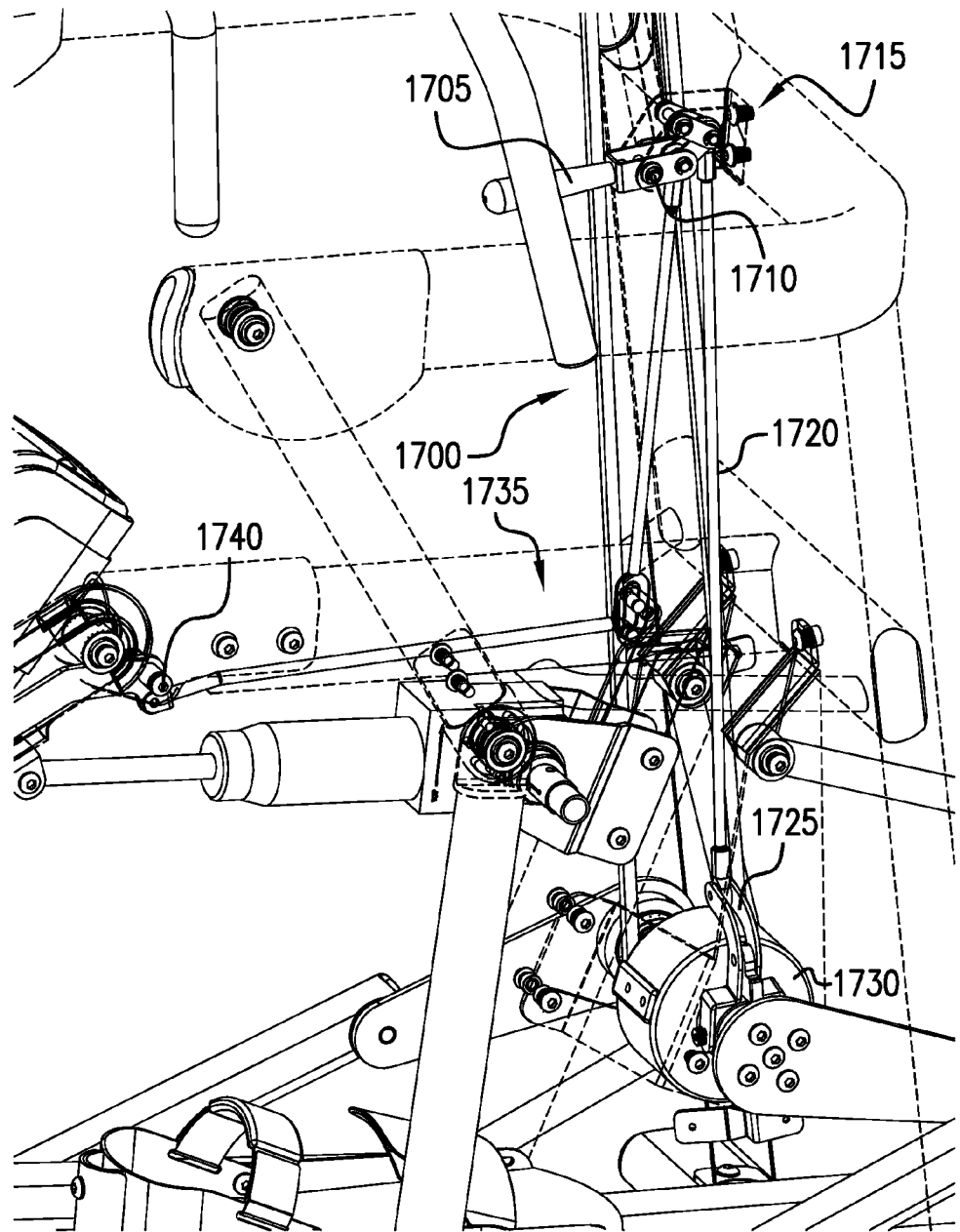

FIGS. 17A-17B depict an exemplary stand-to-walk transmission system. FIG. 17A depicts a stand-to-walk transmission system 1700 in a standing mode. FIG. 17B depicts the stand-to-walk transmission system 1700 in a walking mode. The stand-to-walk transmission system 1700 includes a control lever 1705. The control lever 1705 is pivotably coupled to the frame at a pivot point 1710. The control lever 1705 is also coupled to a linkage system 1715 that controls the vertical throw of a transmission connecting rod 1720. The transmission connecting rod 1720 is connected to the control lever 1725, which operates the slidable right locking member 1730. A zero-degree safety system 1735 operates to ensure that the transmission is in a zero-degree phase relationship whenever the pivotable seat assembly is lowered to a sitting position. Such a zero-degree safety system may advantageously protect a user from injury resulting from improper body kinetics during sitting transitions.

Figure 18A:
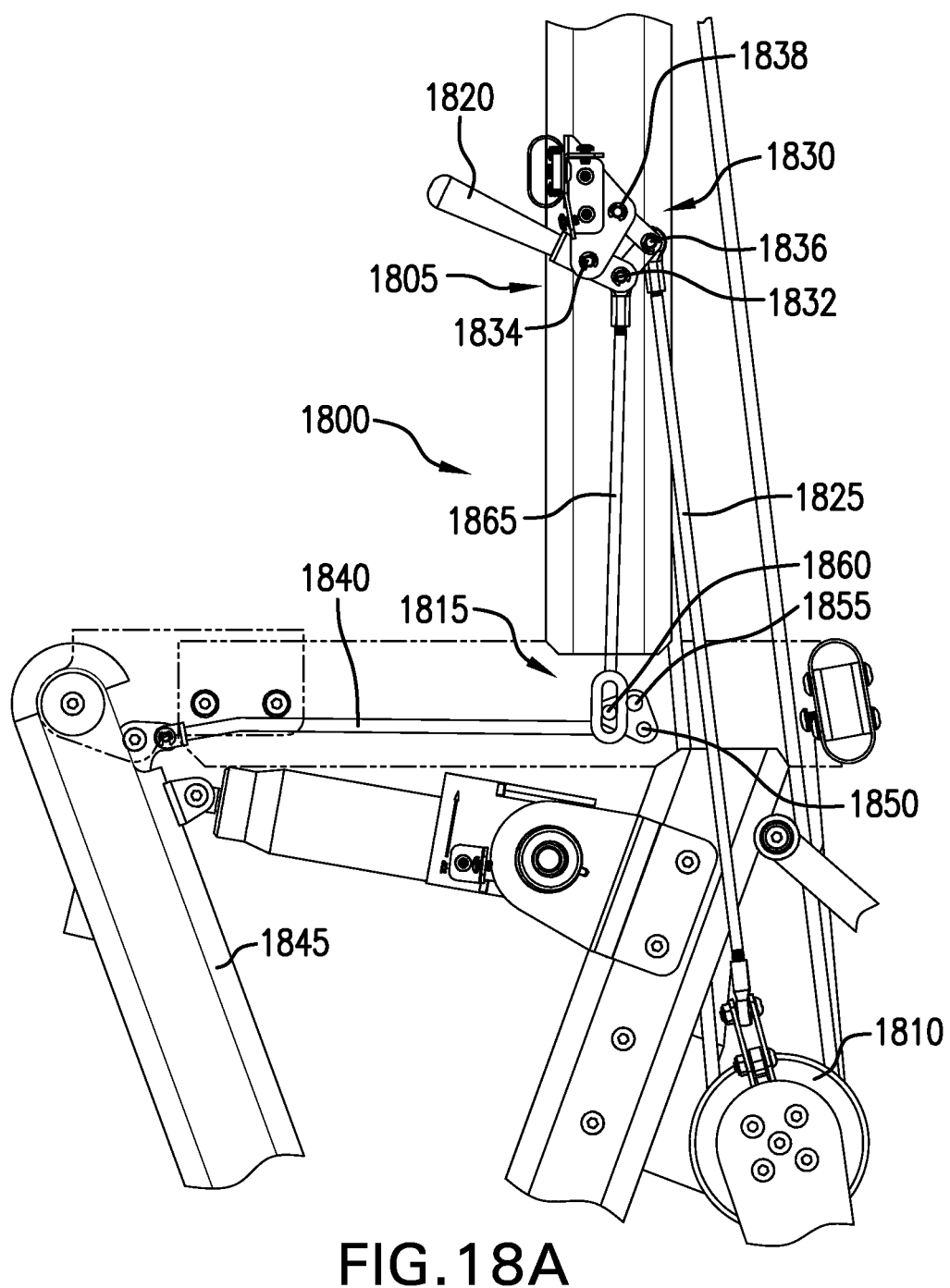
Figure 18B:
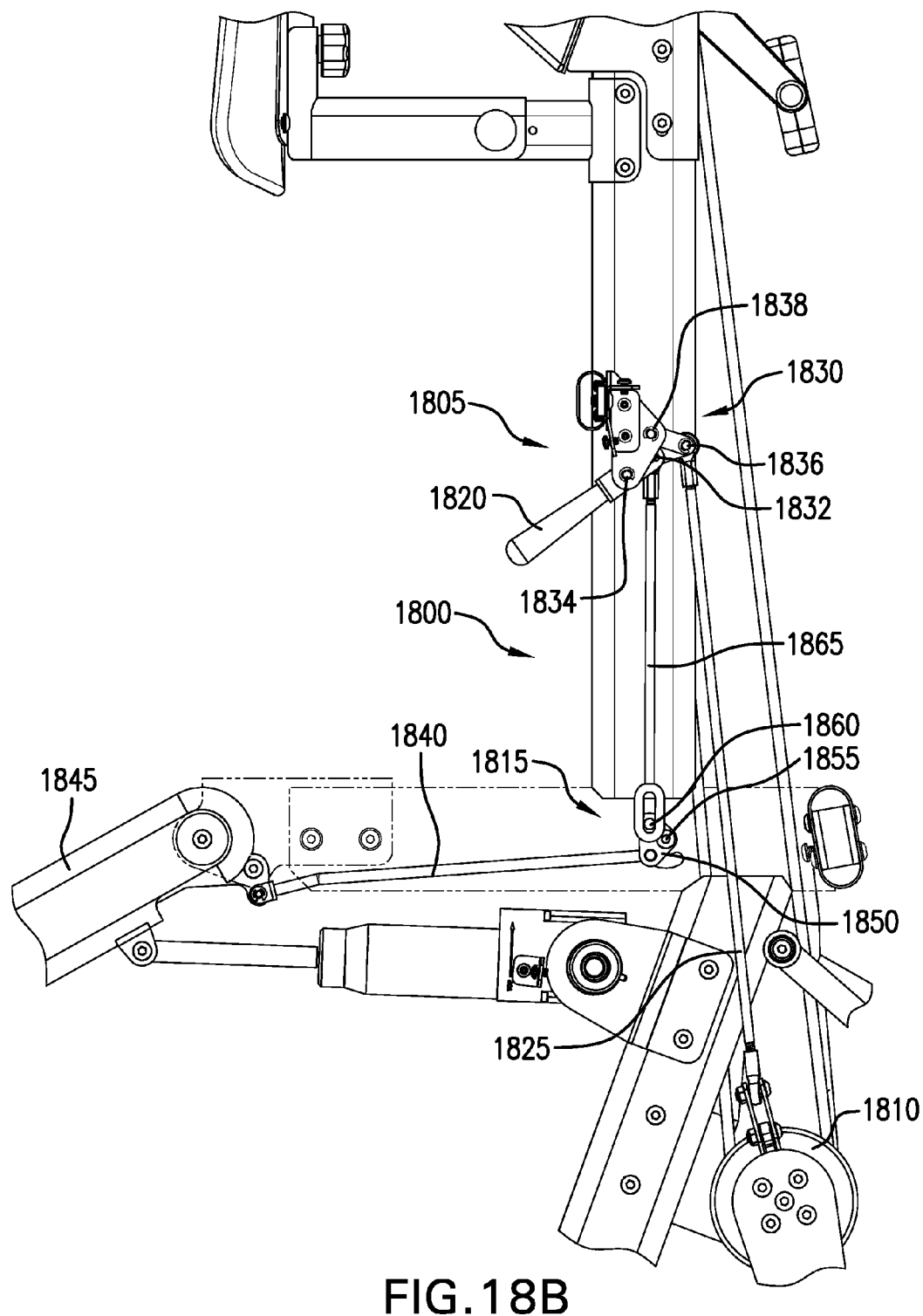

FIGS. 18A-18B depict an exemplary zero-degree safety system. FIG. 18A depicts a zero-degree safety system 1800 when a pivotable seat assembly is in a sitting position. FIG. 18B depicts the zero-degree safety system when a pivotable seat assembly is in a walking position. In FIGS. 17A-17B, a control arm 1740 may pivot in response to the position of the pivotable seat assembly. In both FIGS. 18A-B, a foot phase control system 1800 includes a hand control mechanism 1805, a transmission module 1810 and a zero-degree safety system 1815. The zero-degree safety system 1815 may ensure that a user's feet are in a side-by-side configuration during sit-to-stand and/or stand-to-sit operations. Ensuring such a side-by-side feet configuration during such operations may advantageously prevent injury that may result from anatomically incorrect feet position during such standing or sitting operations.

The hand control mechanism 1805 depicted in FIGS. 18A-B include a manual control lever 1820 that may be actuated by a user. The depicted manual control lever 1820 may be toggled between a first position depicted in FIG. 18A and a second position depicted in FIG. 18B. The first position, depicted in FIG. 18A may force a transmission control rod 1825 toward the transmission module 1810. When the transmission control rod 1825 is forced toward the transmission module 1810, the transmission module 1810 may couple a right and a left foot drive gears in a zero-degree phase relation. The second position, depicted in FIG. 18B may force a transmission control rod 1825 away from the transmission module 1810. When the transmission control rod 1825 is forced away from the transmission module 1810, the transmission module 1810 may couple a right and a left foot drive gears in a 180-degree phase relation.

A biasing force may be used to bias the hand control mechanism 1805. For example, a spring may bias the transmission control rod 1825 in the direction toward the transmission module 1810. When so biased, the hand control mechanism 1805 may have two stable positions, the depicted first position of FIG. 18A and the depicted second position of FIG. 18B. Positions that are intermediate to the first position and the second position may automatically return to either the first position or the second position by the biasing mechanism.

The depicted hand control mechanism 1805 has a four-bar linkage system 1830 that four pivotable connections 1832, 1834, 1836, 1838. When a first 1832 of the four pivotable connections 1832, 1834, 1836, 1838 is below center of a position between a second 1834 and a third 1836 of the four pivotable connections 1832, 1824, 1826, 1838, the biasing mechanism may return the first pivotable connection 1832 to the first position, depicted in FIG. 18A, absent user control of the manual control lever 1820. When the first pivotable connection 1832 is above center of the position between the second 1834 and the third 1836 pivotable connections, the biasing mechanism may return the second pivotable connection 1832 to the second position, depicted in FIG. 18B, absent user control of the manual control lever 1820.

There may be a danger, however, that the user may forget to manually operate the control lever 1820 to lock the user's feet in a side-by-side configuration before the user actuates the pump release that allows the user to sit. The zero-degree safety system 1815 may be configured to automatically operate the control lever 1820 to the first position when the seat is being lowered to a sitting position. The zero-degree safety system 1815 may pull the first pivotable connection 1832 below center of the location between the position between the second 1834 and third 1836 pivotable connections, when the seat assembly is lowered below a predetermined threshold.

As the seat assembly is lowered, a control bar 1840, which is coupled to both a pivotable seat connecting member 1845 and a pivoting plate 1850, moves. When the control bar 1840 moves, the pivoting plate 1850 pivots about a pivot point 1855. As the pivoting plate 1850 pivots in a counterclockwise direction, a connecting member 1860 pulls downwardly on a connecting rod 1865. The downward moving connecting rod 1865 pulls the first pivotable connection 1832 downward. When the first pivotable connection 1832 is pulled below center of the second 1834 and third 1836 pivotable connections, the biasing mechanism may complete the operation of placing the foot phase control system 1800 into the first position, depicted in FIG. 18A.

Figure 19A:
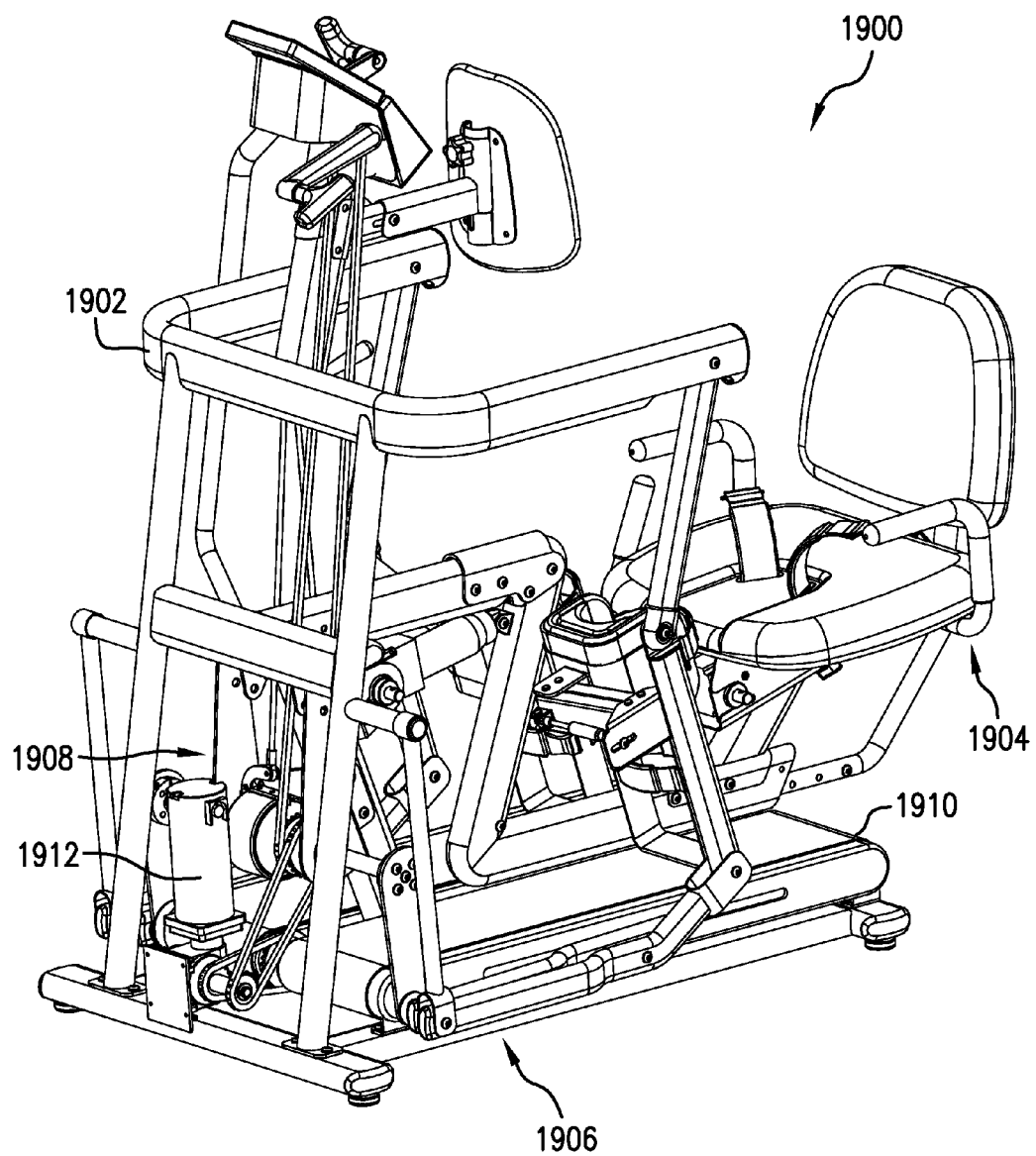
FIGS. 19A-19C depict an exemplary automated treadmill therapy system.
Figure 19B:
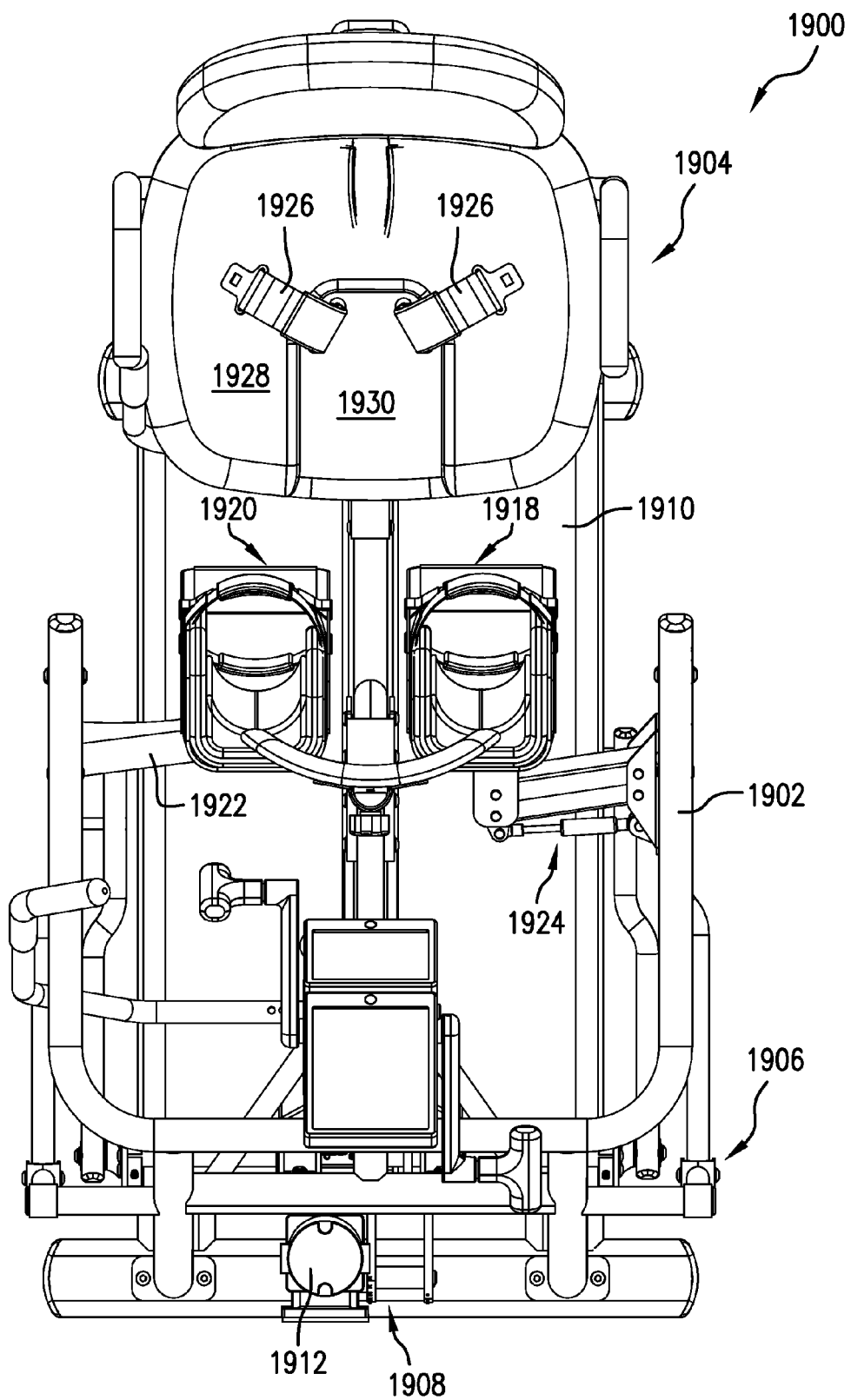
Figure 19C:
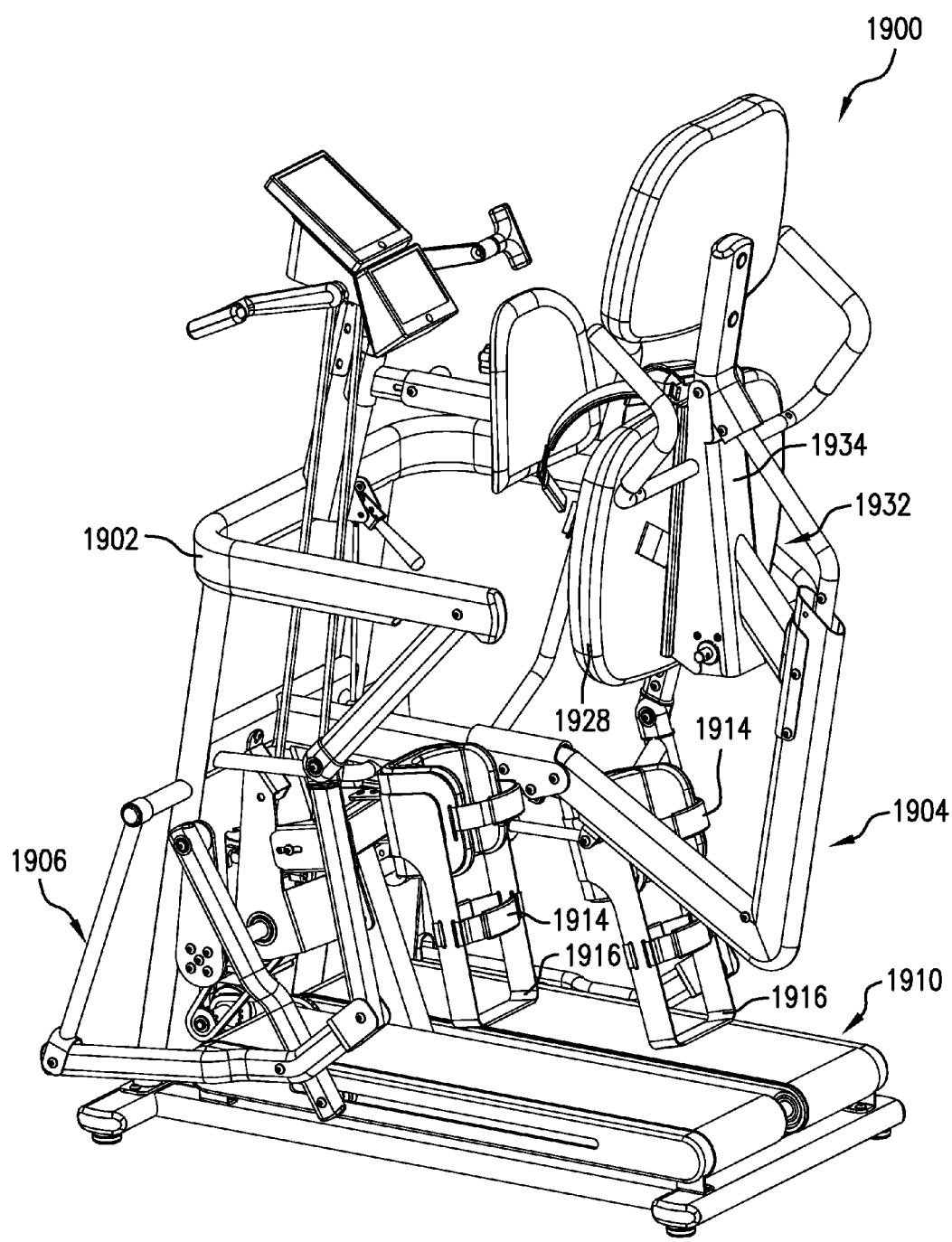

FIGS. 19A-19C depict an exemplary automated treadmill therapy system. In FIGS. 19A-19C an exemplary treadmill therapy system 1900 includes a frame 1902, a sit-to-stand system 1904, a natural-gait assisting system 1906, a locomotion power drive system 1908, and a treadmill system 1910. In FIG. 19A the exemplary treadmill therapy system 1900 is depicted in a sitting position. Treadmill therapy devices may be used, for example, to provide therapy to users who have some leg function. For example, a stroke victim may have use of one side of the victim's body. And so a therapy device that permits the stroke victim to walk on one side, while simultaneously assisting the other side may yield positive medical benefits. A philosophy of such a therapy device is to provide a graduated level of assistance to a person and only where needed.

In the depicted embodiment, the locomotion power drive system 1908 includes an electric motor 1912. The electric motor 1912 may prove drive power to one or both of the treadmill system 1910 and the natural-gait system 1906. The treadmill system 1910 and the natural-gait assisting system 1906 may be powered in a coordinated fashion. For example the rate that the treadmill runs may be substantially the same rate that the natural gait system runs. The natural-gait assisting system 1906 includes a lower leg engagement system 1914. The lower leg engagement system 1914 may include a stirrup 1916 to provide support to a user's foot. In some embodiments, the stirrup 1916 may be made of a flexible material. For example, the stirrup 1916 may include a webbing material. A flexible stirrup 1916 may permit a user to engage a treadmill surface when the natural-gait assisting system positions the user's foot in close proximity to the treadmill surface. Synchronizing the treadmill system 1910 to the natural-gait assisting system 1906 may provide optimum therapy to user's who have some limited motor function.

In FIG. 19B, the depicted treadmill therapy system 1900 has dissimilar connecting members for left leg engagement system 1918 and a right leg engagement system 1920. A right-side connecting member 1922 may rigidly connect the right leg engagement system 1920 to a right-side natural-gait control member. A left-side connecting member 1924 may flexibly connect the left leg engagement system 1918 to a left-side natural-gait control member. The left-side connecting member 1924, may present a spring force to the user's left leg, for example. If the user desires to move the left leg in somewhat dissimilar manner than the motion imparted by the natural-gait assisting system, the left-side connecting member 1924 may accommodate such dissimilar movements.

In some embodiments, the flexible connecting member 1924 may permit forward and/or backward lower leg movement (e.g. x-axis movement). In some embodiments, the flexible connecting member 1924 may permit vertical lower leg movement (e.g. z-axis movement). In some embodiments the flexible connecting member 1924 may permit x-z rotational movements. In some embodiments, various combinations of such permitted movements may be together permitted. In an exemplary embodiment, only a leg engagement system and its associated connecting member may be entirely removed so as to permit a user to use one side of the treadmill independently while being assisted on the other side.

In various embodiments, a leg engagement system may include pressure sensors therein. Such pressure sensors may provide feedback for use in assessing a therapy session, for example. A pressure measurement may, for example, provide information useful in adjusting a spring constant or a gas pressure in a flexible connecting member 1924. Such changes may effect a change in the resistance offered by the flexible connecting member 1924.

In some embodiments, the sit-to stand system 1904 may lift a user not just to a standing position, but to a position just above such a standing position. After being lifted to such a position, the user may be lowered to the treadmill in a manner that controls the amount of a user's weight that is subjected to the treadmill. The user may employ a seat-attached harness 1926 to secure the user's legs to a seat bottom 1928, for example. The seat may have a deployable support member 1930 for supporting the user when the seat bottom is otherwise oriented perpendicular to a ground surface (e.g. when in the standing position). The deployable support member 1930 may be pivotably connected to the seat bottom 1928. The deployable support member 1930 may be rotated to project between a user's legs, thereby providing a support.

Various means of controllably lowering a user to the treadmill may be performed. For example, the controlled lowering of a user to the treadmill may be performed using a seat slide control system 1932. The seat bottom 1928 may be slidably coupled to a seat support member 1934. The seat bottom 1928 may be ratcheted back before the user transitions to a standing position. In some embodiments, the seat bottom 1928 may be ratchet up as the user transitions to a standing position. In some embodiment, a hydraulic pump may provide power for seat-slide operation. In some embodiments and electric motor may provide power for seat-slide operation. Controlling the amount of weight that a user's legs must bear may advantageously minimize injury risk to user's who have poor bone density, for example.

Figure 20A:
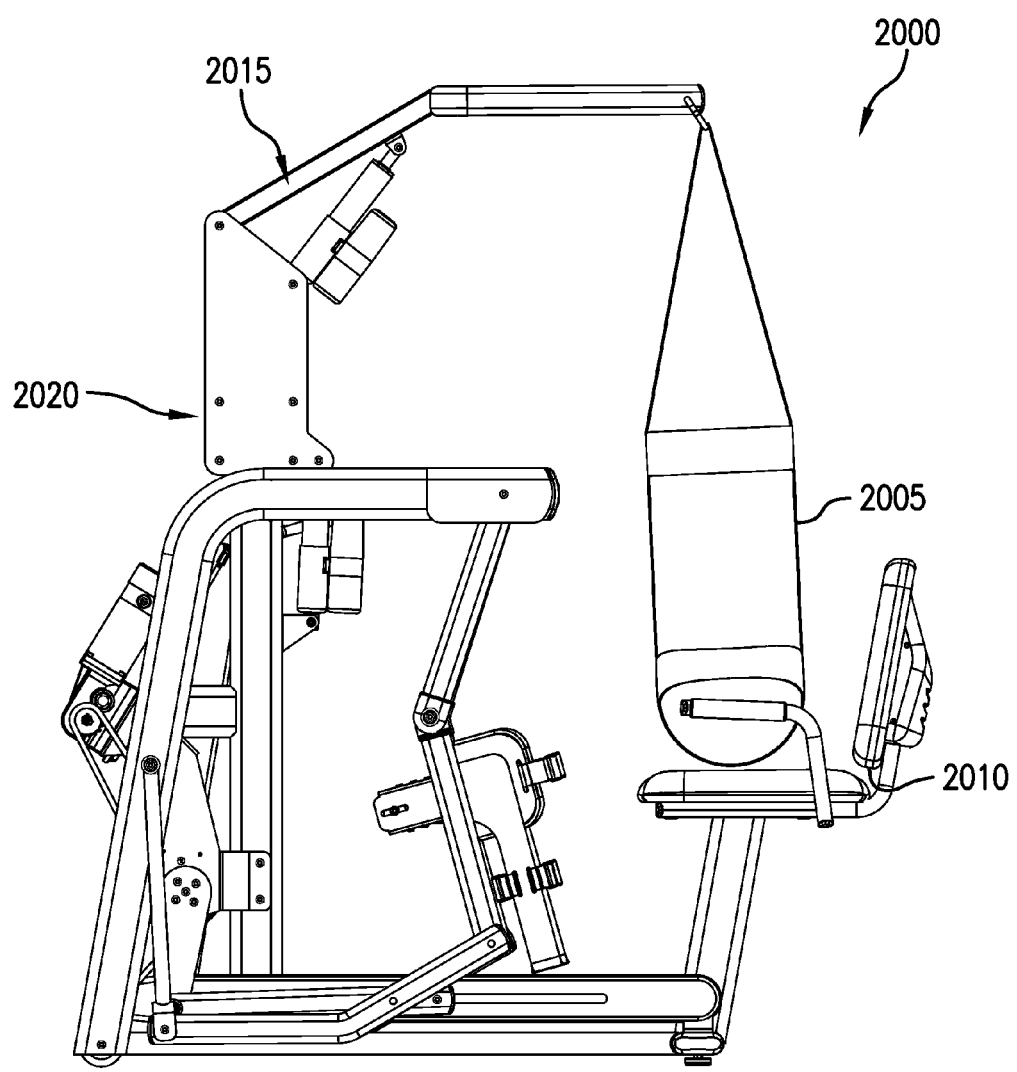
FIGS. 20A-D depict an exemplary lift system for use with a natural-gait therapy system.
Figure 20B:
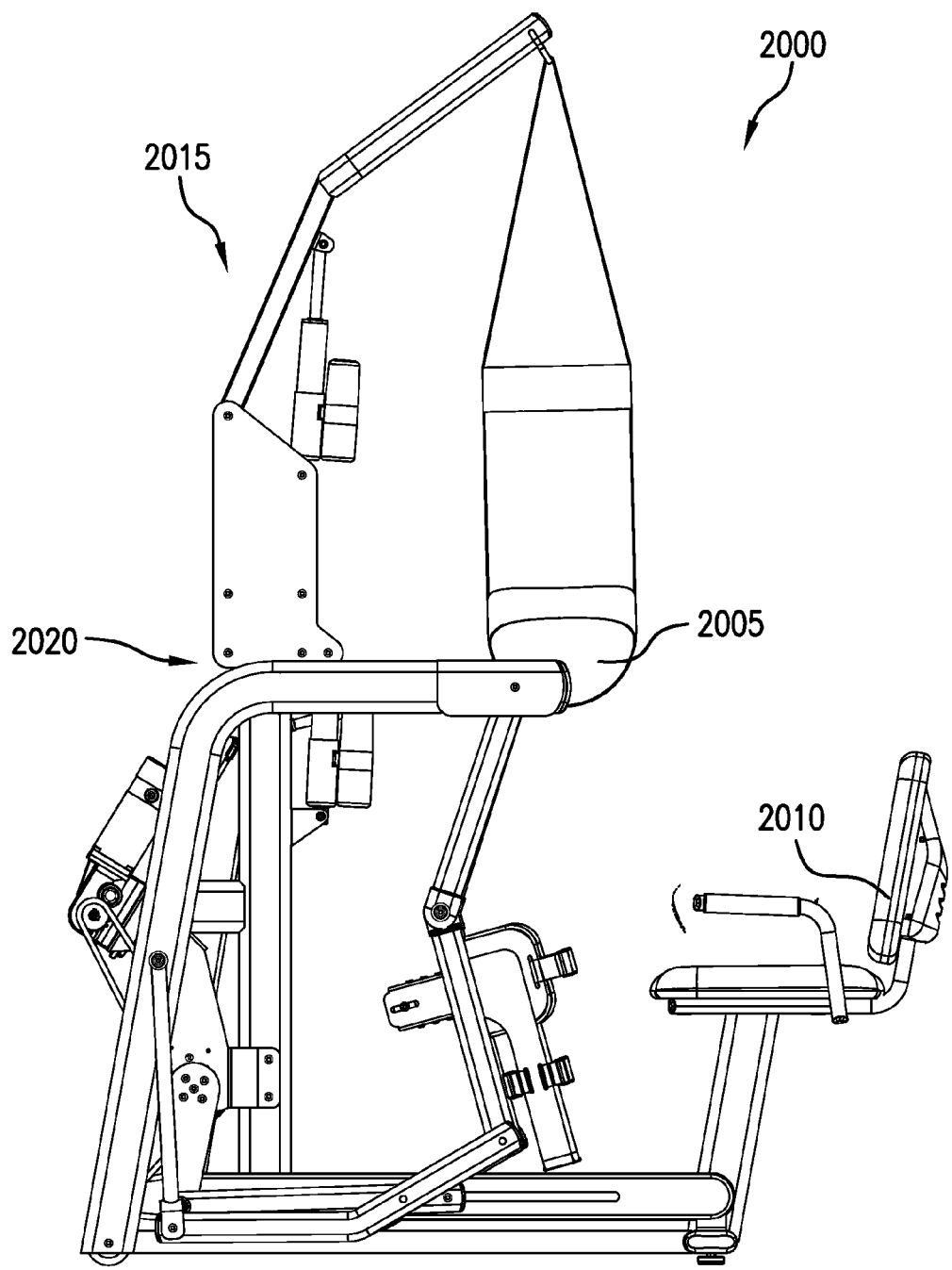
Figure 20C:
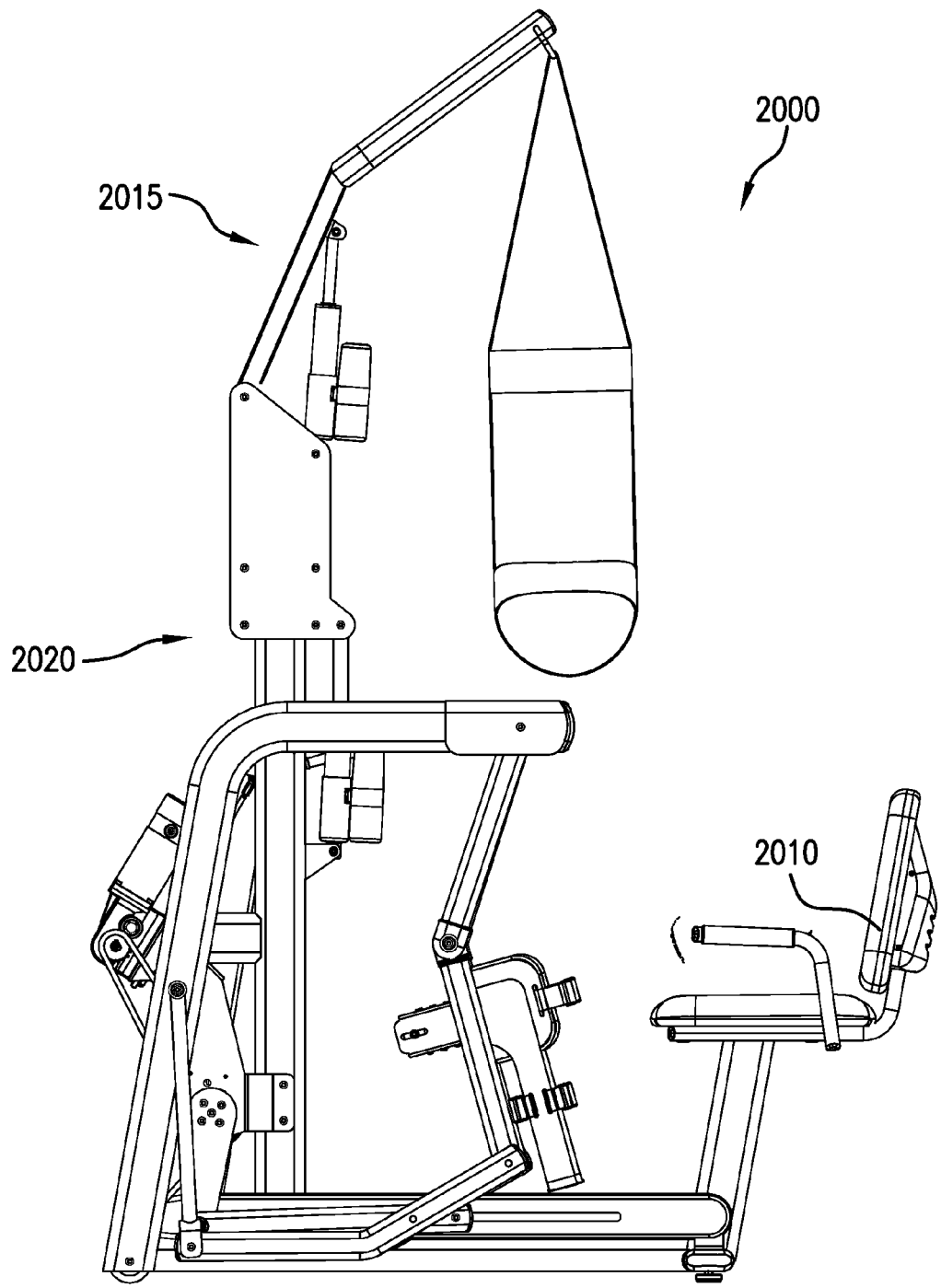

FIGS. 20A-D depict an exemplary lift system for use with a natural-gait therapy system. FIG. 20A, depicts the exemplary lift system 2000 in a sitting configuration. In such a sitting configuration, a harness 2005 is accessable to a user who is seated in a chair 2010. The user may secure the harness 2005 to the user's body. The user may then actuate a pivoting mechanism 2015 to lift the user to a standing configuration, such as that depicted in FIG. 20B. The depicted exemplary lift system 2000 includes a linear lifting mechanism 2020 that can be used to raise or lower the user to a desired altitude above a treadmill 2025, for example. A lift control system may coordinate the operation of both the linear mechanism 2020 and the pivoting mechanism 2015 to raise the user from a sitting position to a standing position in an atomically correct fashion. In some embodiments, a lifting trajectory may be customized for each user of the natural-gait therapy system.

In some embodiments, after the user has been lifted to a standing position, the user may adjust the linear mechanism 2020 to permit more or less body weight incident upon the treadmill surface. For example, a user who may have been injured may desire to be substantially suspended high above the treadmill. As the user heels over time, the user may adjust the linear mechanism 2020 lower and lower. A lower position may permit the user to bear more of the user's weight as the user is heeling. Eventually, as the user becomes strong, the user may position adjust the linear mechanism 2020 so low that the user bears virtually all of the user's weight. The harness may simply be present, in such a case, as a safety device should the user fall during therapy.

Figure 20D:
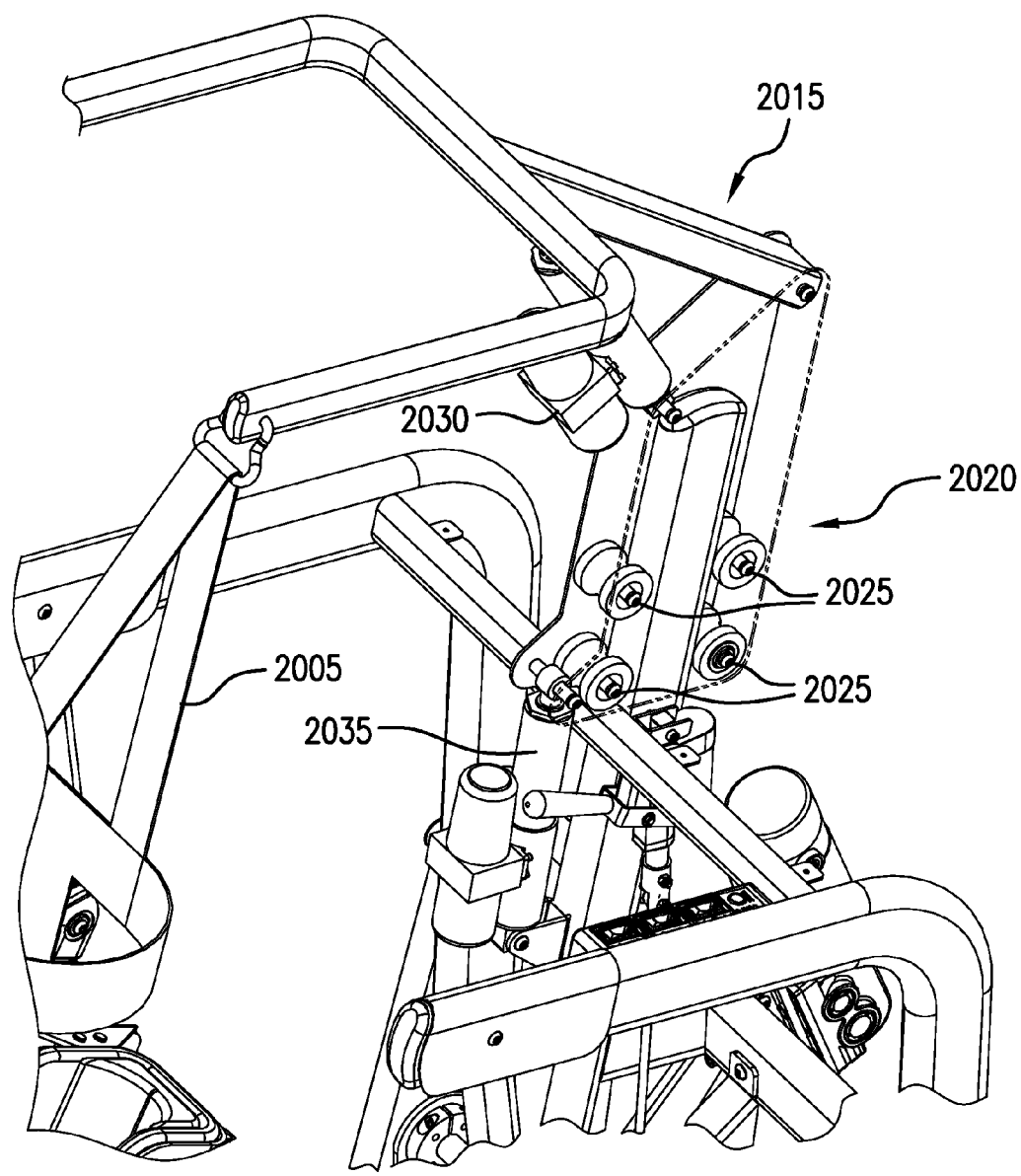

FIG. 20D depicts a closeup perspective view of the exemplary lift system 2000. The linear mechanism 2020 has been made semi-transparent so that inner rolling guides 2025 are visible. In the depicted embodiment, the pivoting mechanism 2015 can be actuated via a hydraulic pump 2030. The linear mechanism 2020 too is actuatable by a hydraulic pump 2035. Each of these hydraulic pumps 2030, 2035 may be controlled by toggle switches 2040 accessable to a user.

Figure 21A:
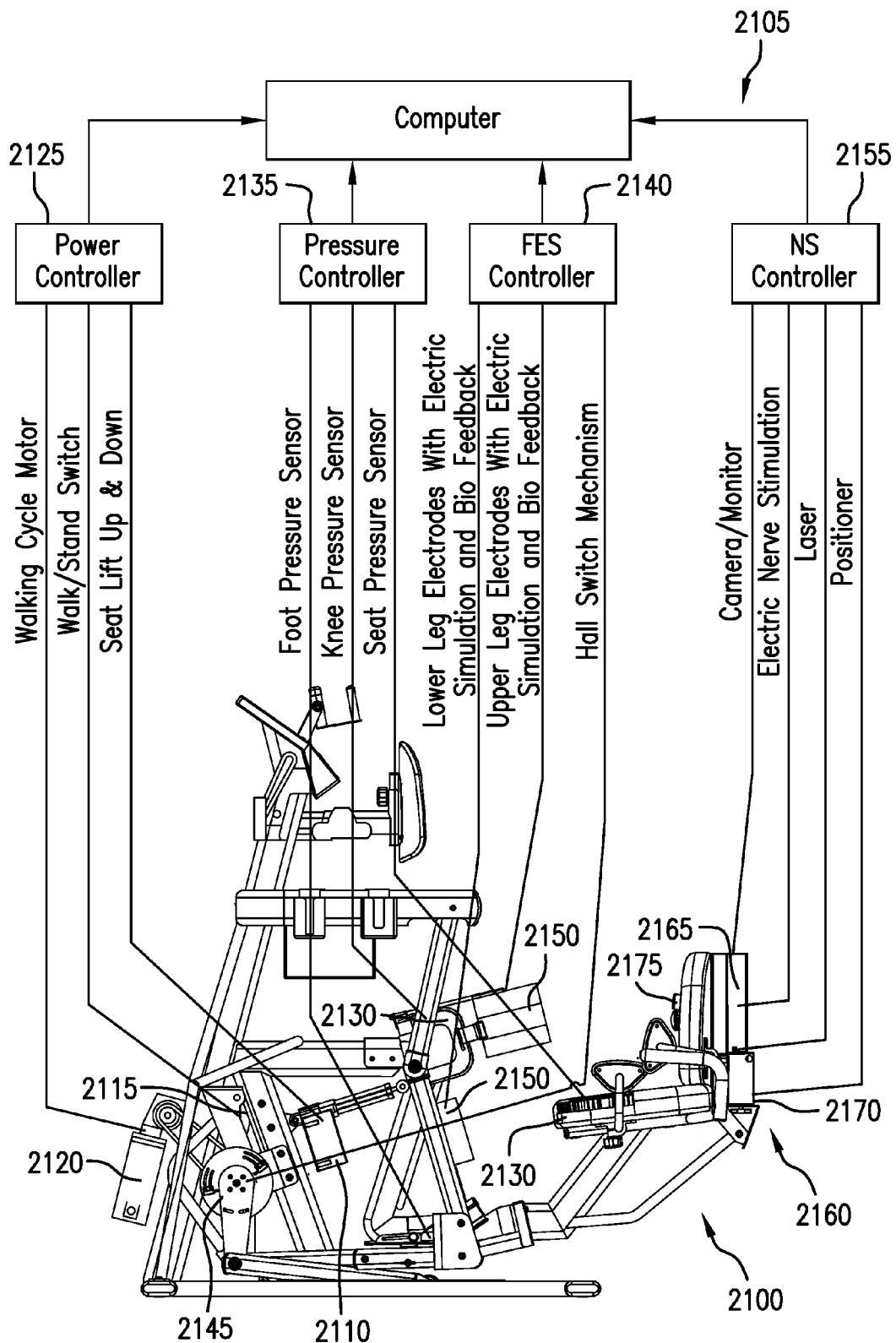
FIGS. 21A-B depict an exemplary multi-modal therapy platform control system.

FIG. 21A depicts a schematic diagram of an exemplary multi-modal therapy platform control system. In the figure, an exemplary multi-modal therapy device 2100 and a therapy control system 2105 are depicted. The depicted multi-modal therapy device 2100 is automated so as to facilitate therapy for a user who may have severely compromised physical function, for example. The automated functions of the multi-modal therapy device 2100 includes a seat lift motor 2110, a solenoid actuator 2115 for a foot phase transmission module, and a natural-gait locomotion motor 2120. Each of these automated functions may be coordinated by a power controller 2125 of the therapy control system 2105.

The multi-modal therapy device 2100 includes pressure sensors 2130 for monitoring a user's engagement of the various engagement surfaces (e.g. seat bottom, seat back, knee rests, foot rests, etc.). A pressure monitoring system 2135 may receive signals from the pressure sensors 2130, each signal may be indicative of a pressure at an engagement surface. The received signals may be used in various ways. For example, the pressure controller may record these pressure indicative signals for use in post therapy analysis. If a received signal indicates an overpressure condition, the pressure controller may send a signal to the power controller, the sent signal indicating that the power controller should terminate operation, for example.

Functional Electrical Stimulation (FES) and/or bio-feedback may be performed using the depicted multi-modal therapy device 2100. An FES controller and/or bio feedback system 2140 may receive signals from a phase detector 2145 indicative of a user's leg positions within a natural-gait cycle. The FES controller and/or bio feedback system 2140 may send signals to muscle stimulating electrodes 2150 for stimulating various muscles in response to the detected positions of a user's legs. In this way, stimulation of a user's muscles may be coordinated with position corresponding to one that these muscles would be activated if the user were locomoting the gait under the user's own power. Bio feedback sensors may sense electrical activity associated with the stimulated muscles. The sensed electrical activity may be sent to the FES controller and/or bio feedback system 2140. In some embodiments, the elctrodes 2150 may be used for both electrical stimulation and for sensing electrical activity of a particular muscle or muscle group1. In some embodiments, an electrical sensor distinct from an associated stimulation electrode may be used to sense electrical activity associated with a muscle or muscle group.

Neural stimulation (NS) may be performed on a user's spinal region using the depicted multi-modal therapy device 2100. An NS controller 2155 may interface with various components located proximate a seatback assembly 2160. The NS controller may control operation of an electric neural stimulator 2165 which can be positioned at an appropriate location relative to a user's spine. For example the neural stimulator 2165 may be positioned near an injury location of a user's spine. A position motor 2170 may be controlled by the NS controller 2155, for example. The NS controller 2155 may position the neural stimulator 2165 in a static fashion, for example. The NS controller 2155 may dynamically oscillate the position of the neural stimulator 2165 about a spinal location, for example. The NS controller 2155 may receive imagery and/or other diagnostic signals from a camera 2170 and/or other sensors, in some embodiments. The NS controller 2155 may control an excitation of a laser stimulator 2175. In some embodiments the laser stimulator 2175 may be positionable by the NS controller 2155.

Figure 21B:
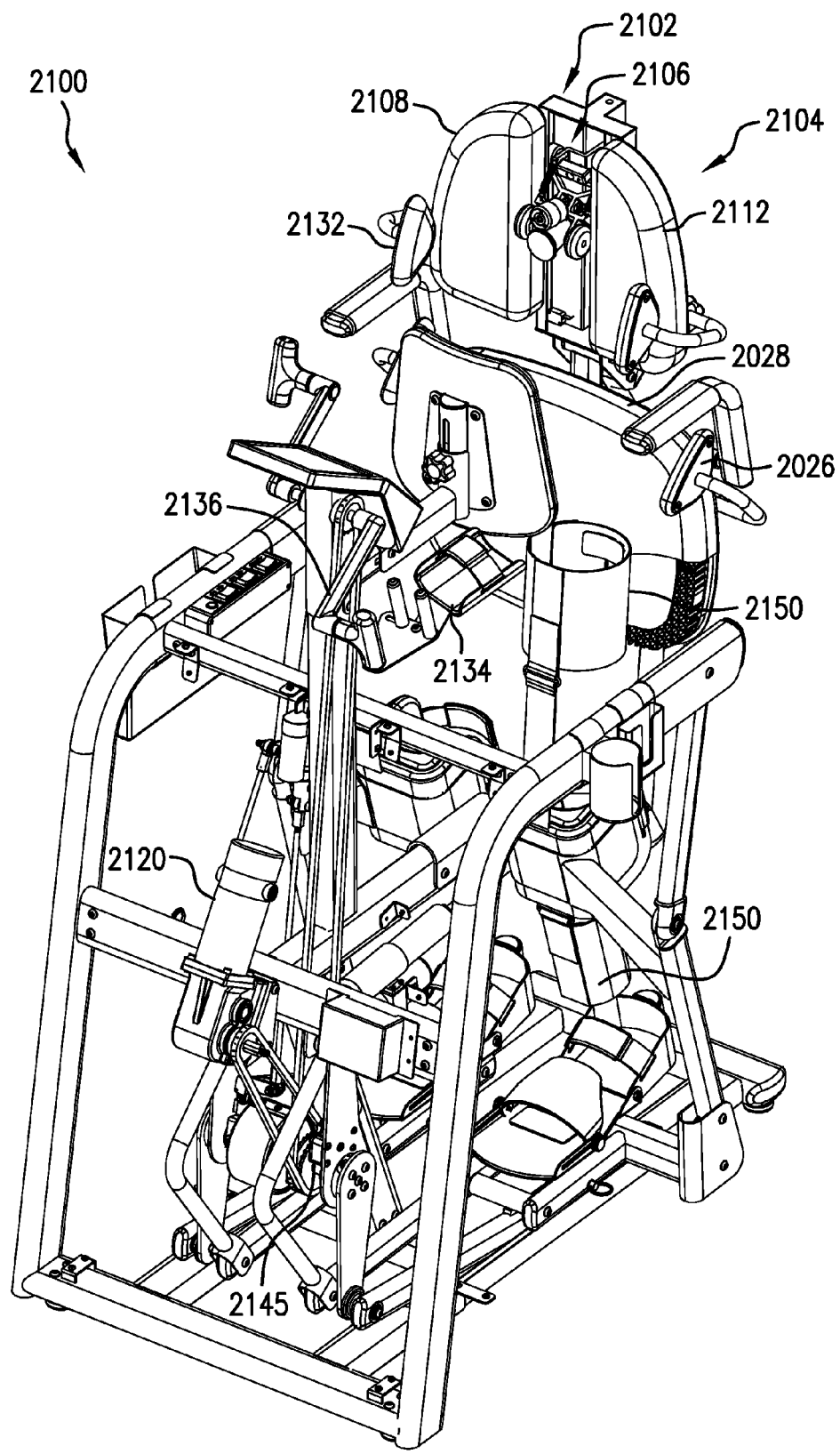

FIG. 21B depicts an exemplary multi-modal gait-based therapy platform. In the FIG. 21B embodiment, a multi-modal gait-based therapy platform 2100 includes a synchronized muscle stimulation system, a nerve stimulation system, a powered natural-gait system, and a pressure monitoring system. The synchronized muscle stimulation system may electrically cause muscle contractions of various muscles at appropriate phases of a natural-gait cycle. The synchronized muscle stimulation system may include a phase detection system 2145, a muscle electrode system, and an FES controller and/or bio feedback system 2135. The phase detection system 2145 may include a drive axle angle detector. Such a phase detection system 2145 may include a shaft encoder. Shaft encoders may be optical, for example. In some embodiments a shaft encoder may be mechanical. In an exemplary embodiment the phase detection system 2145 may include a 360-degree hall sensor.

The muscle electrode system may include a muscle stimulating electrodes 2150. The muscle stimulating electrodes 2150 may be coupled to a knee pad assembly for example. The muscle stimulating electrodes 2150 may be in the form of a cuff containing an exposed electrode. The user may simply affix the cuff to the body part aligning to the cuff. In some embodiments, a Velcro strap may belt the cuff to a leg, for example. In an exemplary embodiment, the cuff may be secured using a webbing and clasp, for example.

In some embodiments, an electrical stimulator cuff may be configured to self-align to muscles in the upper leg. In an exemplary embodiment, an electrical stimulator cuff may be configured to self-align to muscles in the lower leg. In the depicted embodiment, both such electrical stimulator cuffs are present, and upper leg stimulator 2122 and a lower leg stimulator 2124. Control signals for an electrical stimulator may be run within frame members of the multi-modal gait-based therapy platform 2100 so as not to present hazards (e.g. wires caught on clothing) to a user.

The FES controller 2140 may receive signals indicative of the phase from the phase detection system 2145. The FES controller 2140 may calculate a phase based on the received signal indicative of the phase. The FES controller 2140 may compare the calculated phase to a predetermined signal initiation phase associated with a specific muscle or muscle group. The FES controller 2140 may compare the calculated phase to a predetermined signal termination phase associated with the specific muscle or muscle group. If the calculated phase is greater than the signal initiating phase and less than the signal termination phase, the FES controller 2140 may send a predetermined stimulation signal to an electrode associated configured to couple to the specific muscle or muscle group.

A bio-feedback system 2140 may be used in conjunction with the FES controller and/or independently. The bio-feedback system may sense electrical activity associated with a muscle or muscle group. An electrical activity sensor may be included in the electrical stimulator cuffs 2150. In some embodiments, the stimulator electrode may be used as an electrical activity sensor. In some embodiments, an electrical activity sensor may be distinct from a stimulator electrode. The electrical activity sensor may send a signal indicative of sensed electrical activity to a bio-feedback system monitor. In some embodiments the sensed electrical activity signal may be send to a display device for presentation to the user. In some embodiments the electrical activity signal may be logged for later analysis by a therapist or care giver.

Various methods of spinal therapy may be coordinated with the multi-modal gait-based therapy platform 2100. A spinal therapy system 2102 may be coupled to a seat back 2104 of the multi-modal gait-base therapy platform 2100.

The spinal therapy system 2102 may include one or more distinct spinal therapy systems. By way of example and not limitation, an exemplary spinal therapy system 2102 may include a laser stimulation system, an electrical nerve stimulation system, an electrical sensing system, and/or one or more monitoring device (e.g. a camera, an ultrasonic sensor, etc.). The spinal therapy system 2102 may be positionable along a user's spine. In the depicted embodiment, the seat back 2014 has a recess 2106 between a right side 2108 and a left side 2112. The spinal therapy system 2102 may be configured to be positioned vertically within the recess 2106. In some embodiments, a position control system may statically and/or dynamically position the spinal therapy system 2102 within the vertical recess 2106.

Figure 22A:
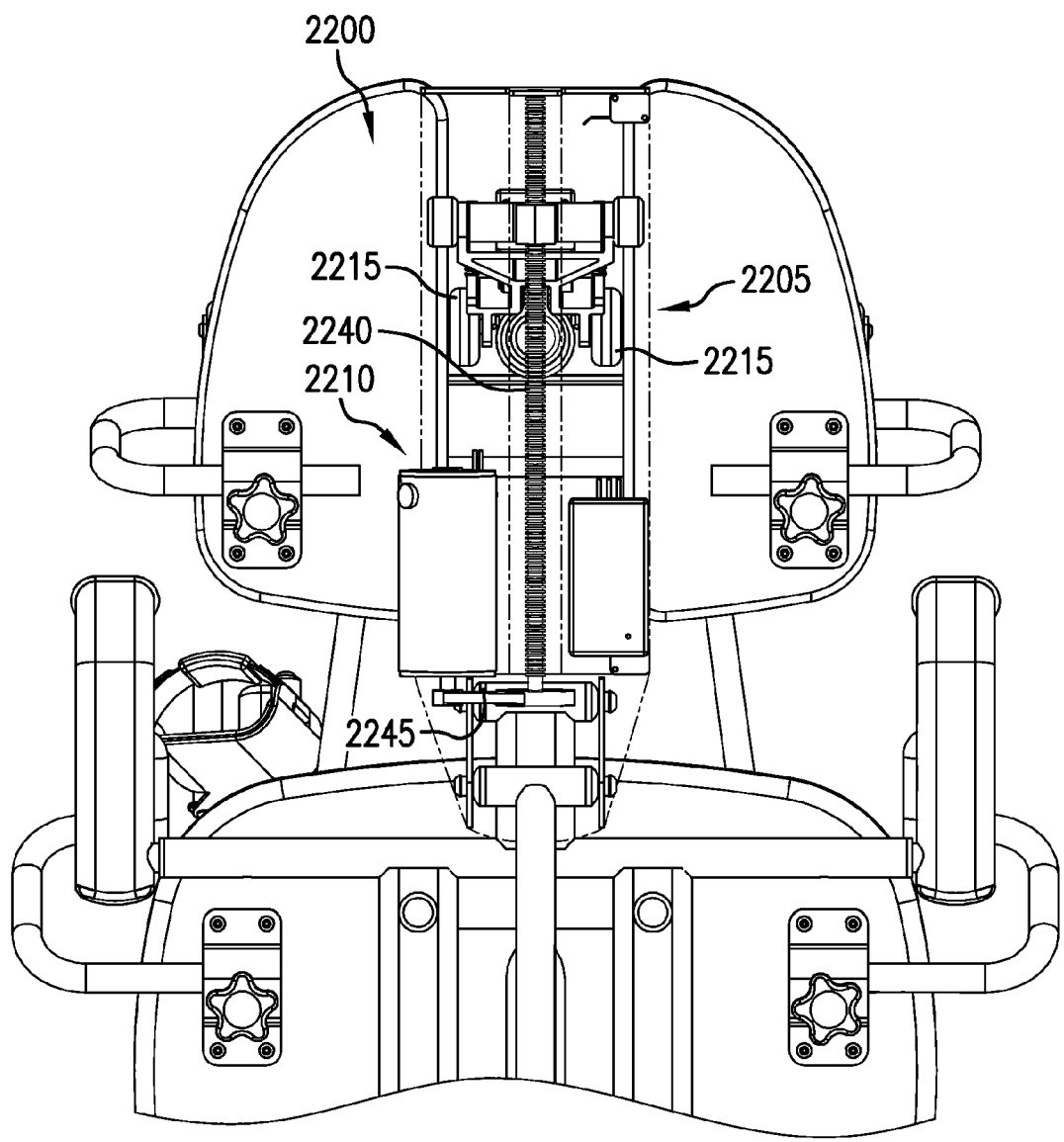
FIGS. 22A-B depict close-up views of an exemplary spinal therapy system.
Figure 22B:
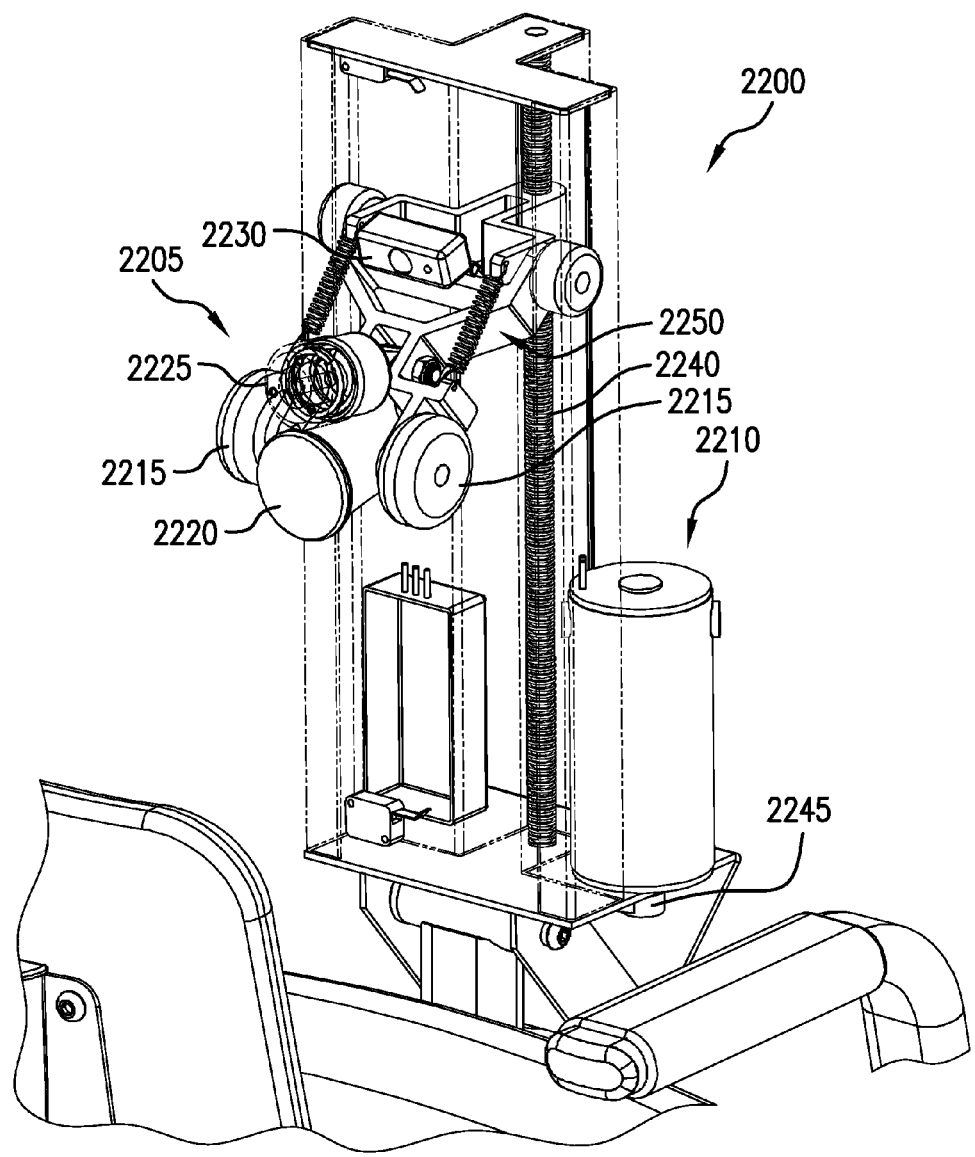

FIGS. 22A-B depict close-up views of an exemplary spinal therapy system. In the FIGS. 22A-B depiction, an exemplary spinal therapy system 2200 includes a positionable carrier 2205 and a positioning system 2210. The positional carrier 2205 includes two rolling stimulating electrodes 2215, an electrical activity sensor 2220, a laser 2225, and a visible light camera 2230. The positioning system 2210 includes a motor 2235 and a screw drive 2240 coupled via a belt 2245. The positioning system 2210 may statically locate the positionable carrier 2205 at a fixed position along the screw drive 2240, for example. The positioning system 2210 may oscillated the positionable carrier 2205 up and down along the screw drive 2240 in some modes, for example. When the positioning system 2210 is operating in a dynamic mode, the rolling stimulating electrodes may maintain electrical connection with a user's back. In some embodiments, one of the rolling stimulating electrodes may be located on one side of a user's spine and the other of the rolling stimulating electrodes may be located on the other side of the user's spine.

The positionable carrier may have a biasing system 2250 that keeps the therapy subsystems 2215, 2220, 2225 in contact with a user's back. In some embodiments, the biasing system may independently bias each of the subsystems 2215, 2220, 2225, so as to maintain contact with a user's back. In some embodiments, a single biasing mechanism may be used to provide a biasing force to the positionable carrier 2210, for example. In some embodiments, the spinal therapy system 2200 may communicate with a remote communications system. For example, the signal information detected by the various analysis devices may be transmitted to a remotely located therapist. The remotely located therapist may then analyze the data and decide to modify the position of a laser therapy device, for example. The remotely located therapist may then send control signals to the nerve stimulation system 2004 corresponding to the laser position. The spinal therapy system 2200 may then provide corresponding control signals to the laser positioning device.

In some embodiments, an automated leg connecting member may adaptively provide movement correction to that movement provided by the natural-gait assisting system. For example, a user may have good use of one side of the body but poor use of the other side. The good-use side may be connected to a flexible connecting member that has sensors to sense the movement difference between that provided by the natural-gait therapy system and the user's actual movement. The automated leg connecting member may then provide the identical corrections at the appropriate phase of the natural-gait of the poor-use side. In this way, the poor-use side will be stimulated to operate in a symmetric manner as the good-use side.

Other features are depicted in the FIG. 21B embodiment. For example, the depicted multi-modal gait-based therapy platform 2100 includes hip support pads 2026. The hip support pads 2026 may be rotatable coupled to the seat bottom 2028 so as to be able to rotate out of a user's way when entering and exiting the multi-modal gait-based therapy platform 2100. Similarly, lateral support structures 2132 may be rotatably coupled to the backrest 2104. Such lateral support structures 2132 may provide support at the sides of a user's torso, for example. A quad grip drive handles 2134 are shown coupled to crank members 2136 of a power drive system. In some embodiments that have a motor drive, such as the depicted multi-modal gait-based therapy platform 2100, a motor disconnect may permit a user to select between providing power manually or electrically, for example.

Various users may configure a multi-modal gait-based therapy platform 2100 in various ways. Some users may require more automation, for example, than other users. For users who require more automation, the multi-modal gait-based therapy platform 2100 may be configured with a power sequencer. The power sequencer may be configured to provide power to the sit-to-stand system in response to an input signal generated by a user interface. The power sequencer may then actuate the stand-to-walk transmission in response to another input signal generated by a user interface. The power sequencer may then actuate a motor that drives the natural-gait locomotion system, for example. The power sequencer may then actuate terminate the natural-gait locomotion system in response to an input signal generated by a user interface. The power sequencer may then actuate the stand-to-walk transmission to return the user's feet to a side-by-side condition. The power sequencer may then transition the user from a standing position to a sitting position.

Figure 23:
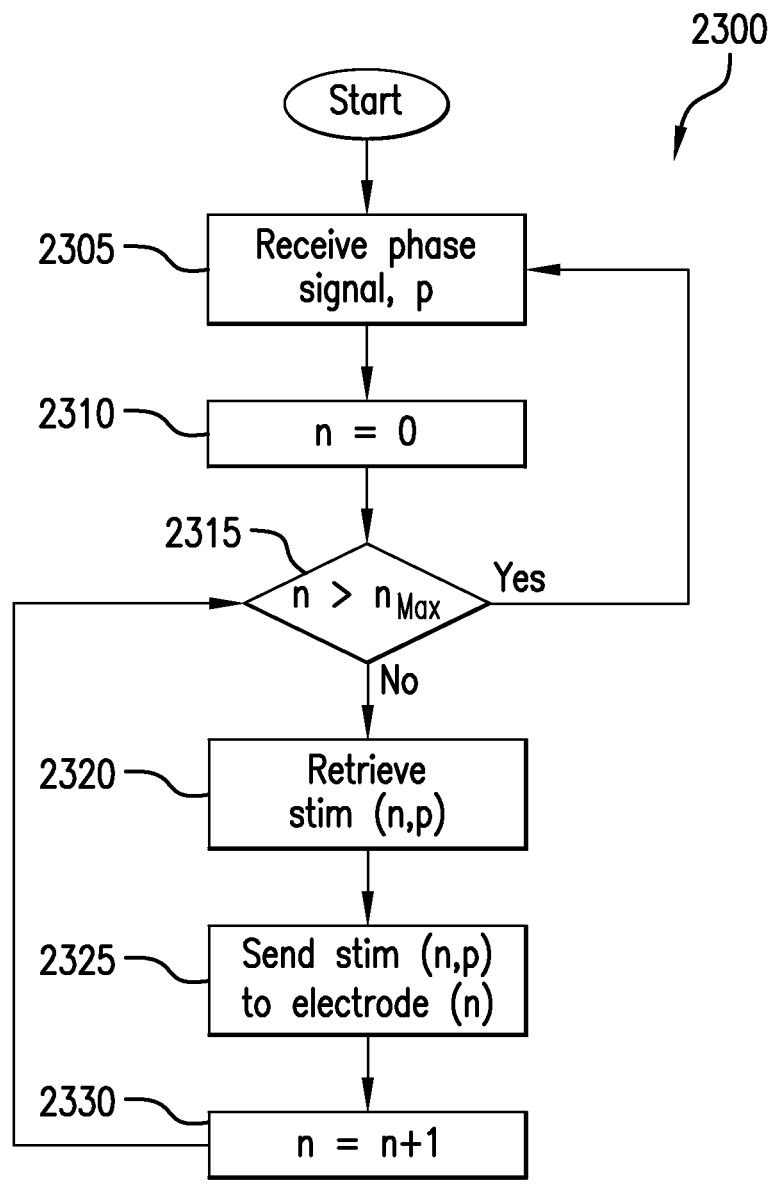
FIG. 23 depicts a flow chart of an exemplary method of providing coordinated muscle stimulation in response to a natural-gait position of a user's body.

FIG. 23 depicts a flow chart of an exemplary method of providing coordinated muscle stimulation in response to a natural-gait position of a user's body. In FIG. 23, an exemplary method 2300 of performing electric stimulation of a user's muscles is depicted from the perspective of the FES controller 2140 of FIG. 21A. The method 2200 begins with the FES controller 2140 receiving, from a phase detector 2145, a signal, p, indicative of a phase 2305. Then the FES controller 2140 initializes an index, n, indicative of one of a plurality of electric muscle stimulators, which may be associated with a particular muscle and/or muscle group 2310. Then the index, n, is compared with a maximum index, $n_{max}$ 2315. If the index, n, is less than the maximum index $n_{max}$, then the FES controller 2140 retrieves a stimulation signal, stim(n, p) 2320. The stimulation signal, stim(n, p), may relate an electrical stimulation strength with a phase for a particular muscle and/or muscle group associated with the index, n, for example. Then the FES controller send the retrieved stimulation signal, stim(n, p), to an electrode configured to contact a user's body in such a way to provide a signal to the associated muscle and/or muscle group 2325. Then the FES controller increments the index, n 2330 and returns to step 2315. If, at step 2315, the index, n, is greater than the maximum index, $n_{max}$, then the method returns to step 2305 and again receives a phase signal, p.

Figure 24A:
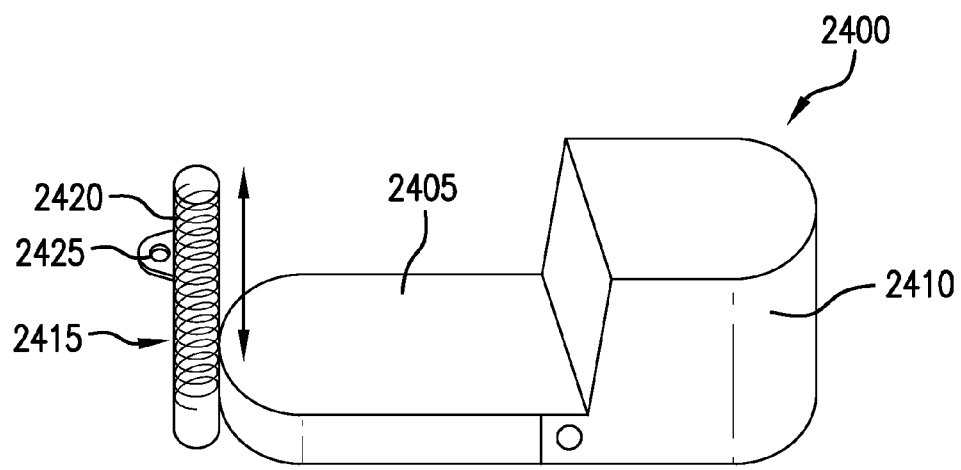
FIGS. 24A-B depict an exemplary foot rest for coordinated operation with a tread mill.
Figure 24B:
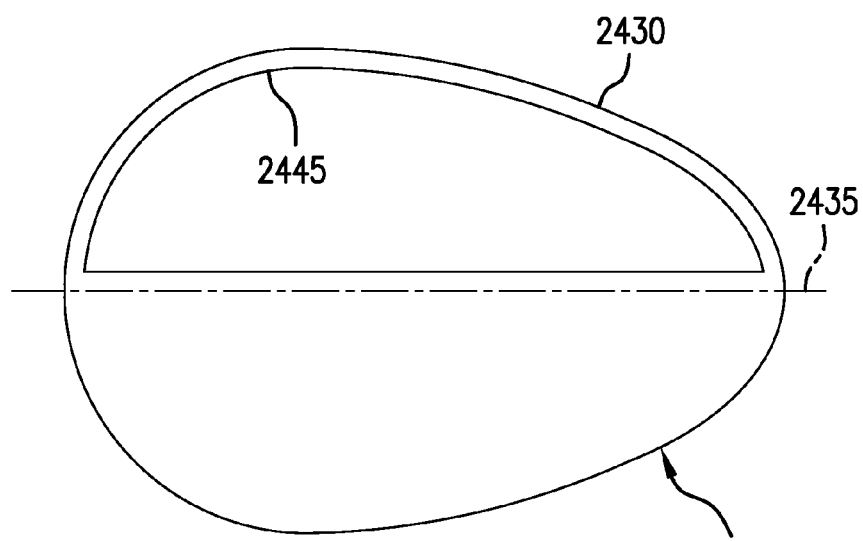

FIGS. 24A-B depict an exemplary foot rest for coordinated operation with a tread mill. In FIG. 24A, an exemplary foot-rest assembly 2400 includes a forefoot platform 2405 pivotably coupled to a heal platform 2410. The forefoot platform 2405 is slidably coupled to an exemplary vertical positioner 2415. A spring member 2420 provides a bias which encourages the forefoot platform 2405 in the direction of a preferred position where the forefoot platform 2405 is coupled to a bottom end of the vertical positioner 2415. When the forefoot platform 2405 engages a hard surface, such as a treadmill surface, for example, the forefoot platform 2405 may move against the spring bias toward a top end of the vertical positioner 2415. In some embodiments, a toe-position control system may engage the vertical positioner 2415 at a coupling point 2425.

In some embodiments, a forefoot strike detection module may detect when the forefoot platform engages a hard surface. For example, a micro switch may be closed when the forefoot platform moves against the spring bias. The forefoot strike detection module may send a signal to the FES controller and/or bio-feedback detection system. The FES controller may send a signal in response to the received forefoot strike detection signal. The FES response signal may be an electrical stimulation signal for a muscle or muscle groups that are associated with a forefoot push off movement during a natural-gait cycle.

FIG. 24B depicts an exemplary cycle of a natural gait 2330. The cycle of the natural gait 2430 may represent the position of an exemplary toe-position control point, for example. The dotted line 2435 may represent a top surface of a tread mill. A bottom portion 2440 of the cycle of the natural gait 2430 is below the top surface of the tread mill 2435. During the phases in which the toe-position control point is below the top surface of the tread mill, a vertical positioner may permit a foot rest to deviate from the position defined by the cycle of the natural gait 2430 and follow the top surface of the tread mill 2435. The resulting cycle 2445 may be that depicted in the figure. Such a resulting natural gait cycle may permit a user to engage the top surface of a treadmill when using a natural gait therapy system.

Figure 25:
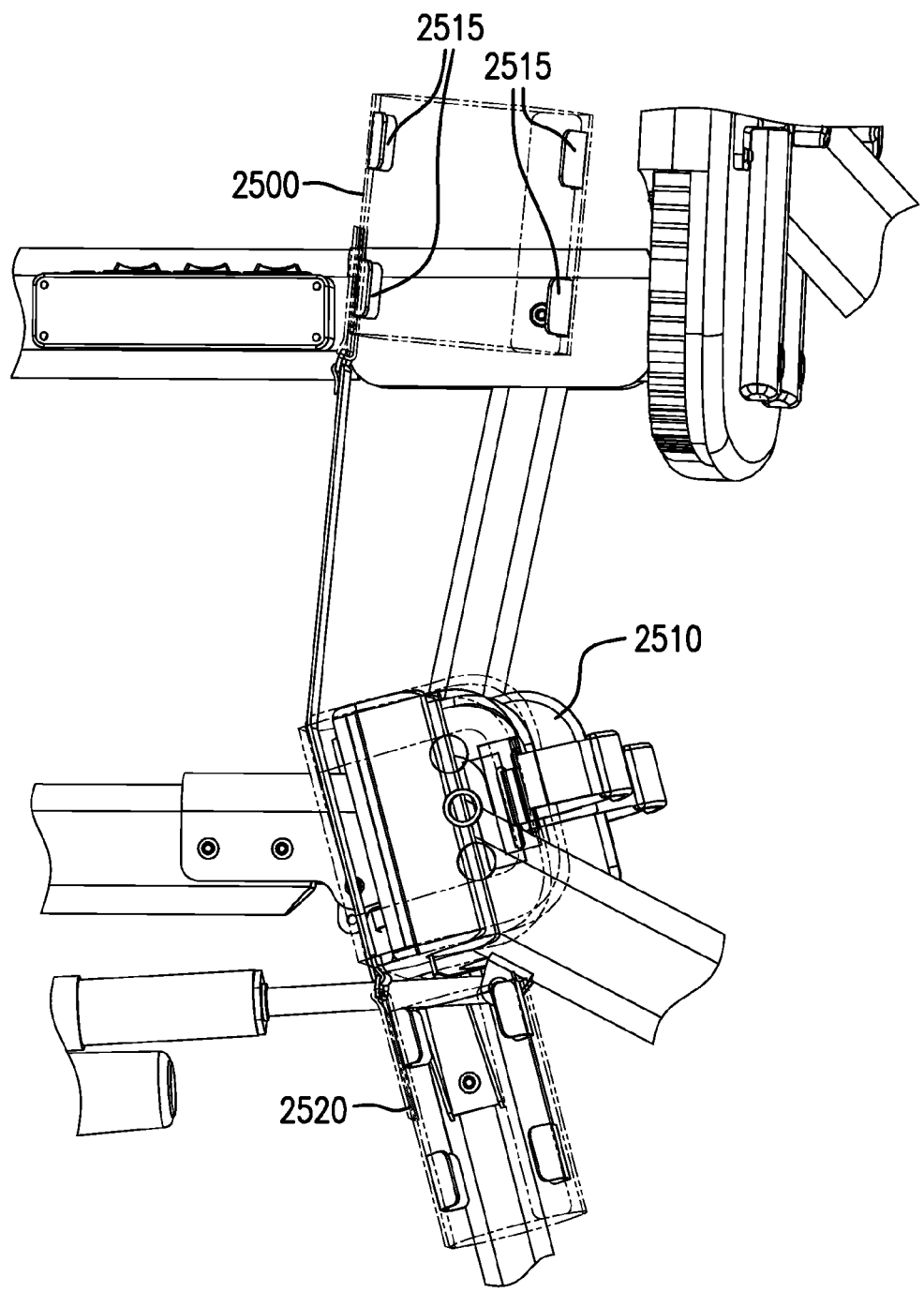
FIG. 25 depicts a closeup perspective view of exemplary FES stimulation and bio-feedback cuffs.

FIG. 25 depicts a closeup perspective view of exemplary FES stimulation and bio-feedback cuffs. In the FIG. 25 depiction, an upper leg FES stimulation and bio feedback cuff 2500 is tethered to a knee engagement system 2505 via a flexible webbing 2510. Electrical wires connect stimulation electrodes 2515 with an FES/biofeedback control module. The electrical wires may run within various structural members of a natural-gait therapy device. The electrical wires may be embedded within the flexible webbing 2510, for example. The cuff 2500 may be an annular elastic band that maintains a tight connection between the stimulation electrodes 2515 and a user's legs, for example. The cuff may be tightened with a belt or a securing device, in some embodiments. In the exemplary depiction, a lower leg FES stimulation and bio feedback cuff 2520 is also tethered to the knee engagement system 2505. In some embodiments, bio feedback electrodes may be coupled to the cuffs 2500, 2520. In an exemplary embodiment the stimulation electrodes 2515 may also provide biofeedback sensing of electrical activity in the users body.

Figure 26:
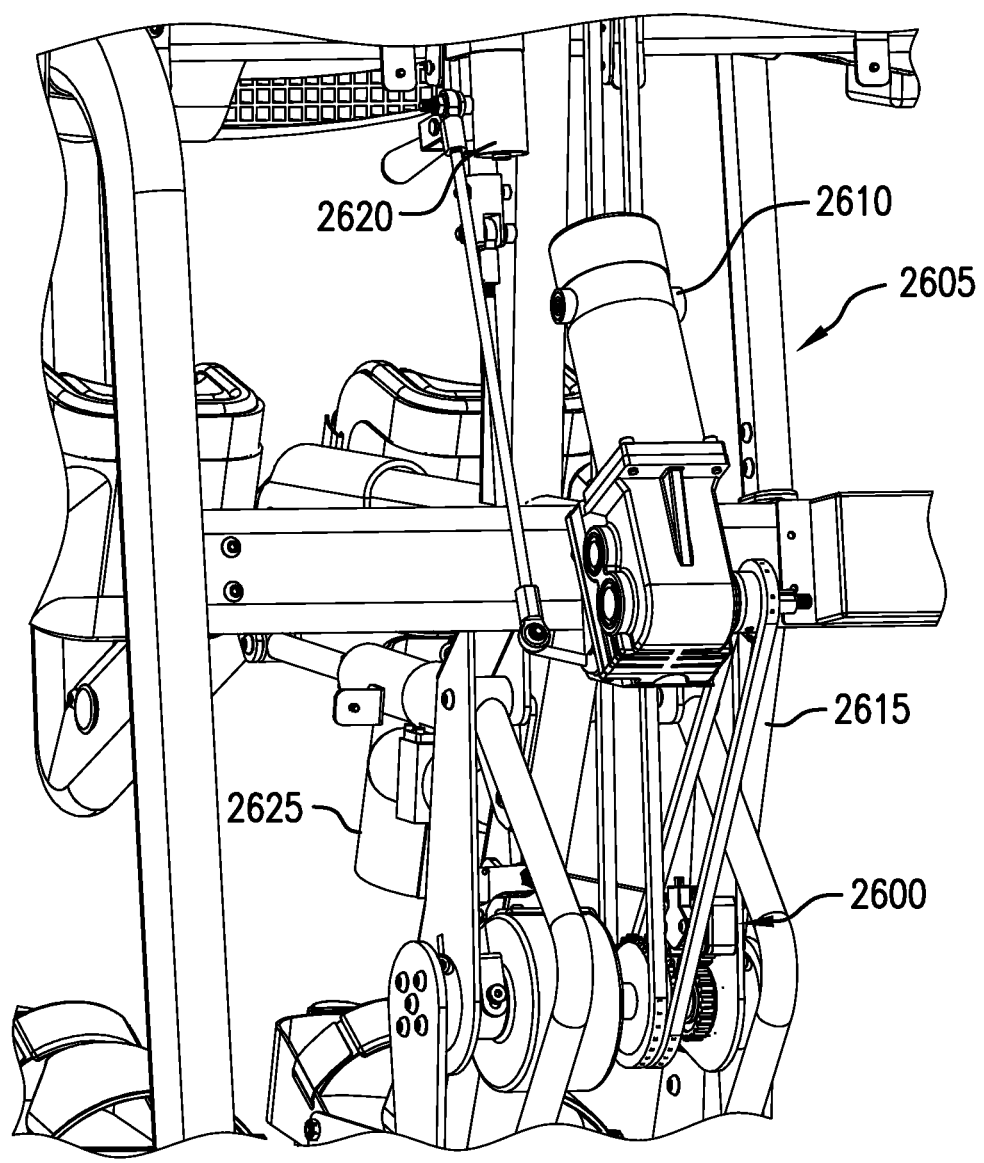
FIG. 26 depicts an exemplary natural-gait therapy system that is automated. Like reference symbols in the various drawings indicate like elements.

FIG. 26 depicts an exemplary natural-gait therapy system that is automated. In the FIG. 26 depiction, an exemplary phase detector 2600 is coupled to a main drive shaft. The phase detector 2600 may be configured to detect the angular phase of the main drive shaft and generate a signal corresponding to the detected angular phase. In the FIG. 26 depiction, the natural-gait therapy system 2605 includes a natural-gait locomotion motor 2610 that may provide locomoting power to the main drive shaft via belt 2615. The natural-gait therapy system 2605 includes an exemplary automatic transmission change module 2620 and a powered seat-lift motor 2625. Such an exemplary powered natural-gait therapy system may provide therapy to users who may require powered operation, for example.

In some embodiments, an upper-leg control member may be pivotably suspended from a support member. In some embodiments, the support member may be a fixed support member configured to provide pivotable suspension of the upper-leg control member on a pivot axis that intersects a user's hip. In some embodiments, the support member may be cyclically driven so as to simulate the motion of a human hip location when walking, for example. In some embodiments, left and right support members may be move in phase with each other. In some embodiments, left and right support members may move 180 degrees out of phase with each other, when in a walking mode.

Some aspects of embodiments may be implemented as a computer system. For example, various implementations may include digital and/or analog circuitry, computer hardware, other sensors (e.g. temperature sensors), firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer. For example, wearable devices, such as Google Glasses or other technologies may facilitate input and/or output operations between a user and a system.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g/n, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:
1. A natural-gait therapy device comprising:
   a support member;
   a knee-position control system comprising:
      an upper-leg control member pivotably suspended by the support member, the upper-leg control member configured to move parallel to an upper leg of a user throughout a cycle of a natural gait;
      a lower-leg control member pivotably suspended by the upper-leg control member, the lower-leg control member configured to move parallel to a lower leg of a user throughout the cycle of the natural gait; and a knee-engagement pad operatively coupled to at least one of the upper-leg control member or the lower-leg control member, the knee-engagement pad configured to maintain substantially static engagement with a user's knee throughout the cycle of the natural gait;

a natural-gait user support module pivotably suspended by the lower-leg control member, the natural-gait user support module configured to support a user throughout the cycle of the natural gait; and a stand-to-walk transmission system having a standing mode and a walking mode, wherein the natural-gait user support module has a forefoot-engagement surface and a heel-engagement surface, wherein an angle between a normal vector of the forefoot-engagement surface and a normal vector of a floor surface forms a forefoot angle, and wherein an angle between a normal vector of the heel-engagement surface and the normal vector to the floor surface forms a heel angle, wherein the heel angle is greater than the forefoot angle during a first portion of the cycle of the natural gait, and the heel angle is substantially equal to the forefoot angle during a second portion of the cycle of the natural gait.

2. The natural-gait therapy device of claim 1, wherein the natural-gait user support module is configured to move a user's foot along an elliptical natural-gait path.

3. The natural-gait therapy device of claim 1, wherein the natural-gait user support module includes a forefoot rest having a forefoot engagement surface configured to maintain substantially static engagement with a user's forefoot throughout the cycle of a natural gait.

4. The natural-gait therapy device of claim 1, wherein the natural-gait user support module includes a heel rest having a heel-engagement surface configured to maintain substantially static engagement of a user's heel throughout the cycle of the natural gait.

5. The natural-gait therapy device of claim 1, further comprising a powered natural-gait locomotion system operatively coupled to drive the natural gait therapy device through the cycle of the natural gait in a periodically repeating fashion, each cycle comprising 360 degrees per period.

6. The natural-gait therapy device of claim 5, wherein the powered natural-gait locomotion system comprises a drive power subsystem and a natural-gait control mechanism.

7. The natural-gait therapy device of claim 6, wherein the natural-gait control mechanism comprises a toe-position control subsystem configured to position a toe portion of the natural-gait user support module at a predetermined location for each phase of the cycle of the natural gait in response to the drive power subsystem.

8. The natural-gait therapy device of claim 7, wherein the powered natural-gait control mechanism comprises a forefoot-angle control system configured to coordinate an angle of a forefoot portion of the natural-gait user support module at each phase of the cycle of the natural gait in response to the position of the toe portion of the natural-gait user support module.

9. The natural-gait therapy device of claim 8, wherein the knee-position control system is configured to coordinate a positioning of the knee-engagement member at each phase of the natural-gait cycle in response to a coordinated movement of the toe-position control system and the forefoot-angle control system.

10. The natural-gait therapy device of claim 9, wherein the powered natural-gait control mechanism comprises a heel-lift control system configured to coordinate a lift of a heel portion of the natural-gait user support module at each phase of the cycle of the natural gait in response to a coordinated movement of the toe-position control system, the forefoot-angle control system, and the knee-position control system.

11. The natural-gait therapy device of claim 1, wherein a foot rest is adjustably disposed on the natural-gait user support module to substantially maintain alignment of a user's knee and an axis of a pivot point at which the lower-leg control member is pivotably suspended by the upper-leg control member.

12. The natural-gait therapy device of claim 6, wherein the drive power subsystem is a hand powered system.

13. The natural-gait therapy device of claim 6, wherein the drive power subsystem is a motor powered system.

14. The natural-gait therapy device of claim 1, wherein the knee-position control system is a left knee-position control system and the natural-gait user support module is a left natural-gait user support module, and the natural-gait therapy device further comprises a right knee-position control system and a right natural-gait user support module.

15. The natural-gait therapy device of claim 14, wherein, when in the standing mode, the left natural-gait user support module and the right natural-gait user support module are operatively coupled in the same phase of the cycle of the natural gait, and wherein, when in the walking mode, the left natural-gait user support module and the right natural-gait user support module are operatively coupled at 180 degrees phase difference in the cycle of the natural gait.

* * * * *